US008796016B2

(12) United States Patent
Tuschl et al.

(10) Patent No.: US 8,796,016 B2
(45) Date of Patent: Aug. 5, 2014

(54) RNA INTERFERENCE MEDIATING SMALL RNA MOLECULES

(75) Inventors: Thomas Tuschl, Brooklyn, NY (US); Sayda Mahgoub Elbashir, Cambridge, MA (US); Winfried Lendeckel, Hohengandern (DE)

(73) Assignees: Max-Planck-Gesellschaft zur Förderung der Wissenschaften E.V., Munich (DE); Massachusetts Institute of Technology, Cambridge, MA (US); Whitehead Institute for Biomedical Research, Cambridge, MA (US); University of Massachusetts, Boston, MA (US)

( * ) Notice: Subject to any disclaimer, the term of this patent is extended or adjusted under 35 U.S.C. 154(b) by 594 days.

(21) Appl. No.: 12/819,444

(22) Filed: Jun. 21, 2010

(65) Prior Publication Data

US 2011/0027883 A1 Feb. 3, 2011

Related U.S. Application Data

(60) Continuation of application No. 11/634,129, filed on Dec. 6, 2006, now abandoned, which is a division of application No. 10/433,050, filed as application No. PCT/EP01/13968 on Nov. 29, 2001, now abandoned.

(60) Provisional application No. 60/279,661, filed on Mar. 30, 2001.

(30) Foreign Application Priority Data

Dec. 1, 2000 (EP) ...................................... 00126325

(51) Int. Cl.
*C12N 15/85* (2006.01)
*C07H 21/02* (2006.01)
*C07H 21/04* (2006.01)

(52) U.S. Cl.
USPC .......................... 435/325; 536/23.1; 536/24.5

(58) Field of Classification Search
None
See application file for complete search history.

(56) References Cited

U.S. PATENT DOCUMENTS

| 4,469,863 | A | 9/1984 | Ts'o et al. |
| 5,208,149 | A | 5/1993 | Inouye et al. |
| 5,457,189 | A | 10/1995 | Crooke et al. |
| 5,514,577 | A | 5/1996 | Draper et al. |
| 5,576,208 | A | 11/1996 | Monia et al. |
| 5,578,716 | A | 11/1996 | Szyf et al. |
| 5,580,859 | A | 12/1996 | Felgner et al. |
| 5,594,122 | A | 1/1997 | Friesen |
| 5,624,803 | A | 4/1997 | Noonberg et al. |
| 5,624,808 | A | 4/1997 | Thompson et al. |
| 5,670,633 | A | 9/1997 | Cook et al. |
| 5,672,695 | A | 9/1997 | Eckstein et al. |
| 5,674,683 | A | 10/1997 | Kool |
| 5,712,257 | A | 1/1998 | Carter |
| 5,719,271 | A | 2/1998 | Cook et al. |
| 5,770,580 | A | 6/1998 | Ledley et al. |
| 5,795,715 | A | 8/1998 | Livache et al. |
| 5,801,154 | A | 9/1998 | Baracchini et al. |
| 5,814,500 | A | 9/1998 | Dietz |
| 5,898,031 | A | 4/1999 | Crooke et al. |
| 5,908,779 | A | 6/1999 | Carmichael et al. |
| 5,919,722 | A | 7/1999 | Szyf et al. |
| 5,919,772 | A | 7/1999 | Szyf et al. |
| 5,972,704 | A | 10/1999 | Draper et al. |
| 5,998,203 | A | 12/1999 | Matulic-Adamic et al. |
| 6,001,990 | A | 12/1999 | Wands et al. |
| 6,057,153 | A | 5/2000 | George et al. |
| 6,107,094 | A | 8/2000 | Crooke |
| 6,218,142 | B1 | 4/2001 | Wassenegger et al. |
| 6,225,290 | B1 | 5/2001 | German et al. |
| 9,889,802 | | 9/2001 | Kreutzer |
| 6,475,726 | B1 | 11/2002 | Tally et al. |
| 6,476,205 | B1 | 11/2002 | Buhr et al. |
| 6,506,559 | B1 | 1/2003 | Driver et al. |
| 6,531,647 | B1 | 3/2003 | Baulcombe et al. |
| 6,573,099 | B2 | 6/2003 | Graham |
| 6,635,805 | B1 | 10/2003 | Baulcombe et al. |
| 6,753,139 | B1 | 6/2004 | Baulcombe et al. |
| 6,939,712 | B1 | 9/2005 | Bahramian et al. |
| 7,056,704 | B2 | 6/2006 | Tuschl et al. |

(Continued)

FOREIGN PATENT DOCUMENTS

CA    2 359 180 A1    7/2001
CA    2432341         7/2002

(Continued)

OTHER PUBLICATIONS

Romaniuk et al., "The effect of acceptor oligoribonucleotide sequence on the T4 RNA ligase reaction", Eur. J. Biochem., 1982, vol. 125, pp. 639-643.

(Continued)

Primary Examiner — Amy Bowman
(74) Attorney, Agent, or Firm — Lando & Anastasi, LLP

(57) ABSTRACT

Double-stranded RNA (dsRNA) induces sequence-specific post-transcriptional gene silencing in many organisms by a process known as RNA interference (RNAi). Using a *Drosophila* in vitro system, we demonstrate that 19-23 nt short RNA fragments are the sequence-specific mediators of RNAi. The short interfering RNAs (siRNAs) are generated by an RNase III-like processing reaction from long dsRNA. Chemically synthesized siRNA duplexes with overhanging 3' ends mediate efficient target RNA cleavage in the lysate, and the cleavage site is located near the center of the region spanned by the guiding siRNA. Furthermore, we provide evidence that the direction of dsRNA processing determines whether sense or antisense target RNA can be cleaved by the produced siRNP complex.

59 Claims, 26 Drawing Sheets

(56) References Cited

U.S. PATENT DOCUMENTS

Figure 1A:
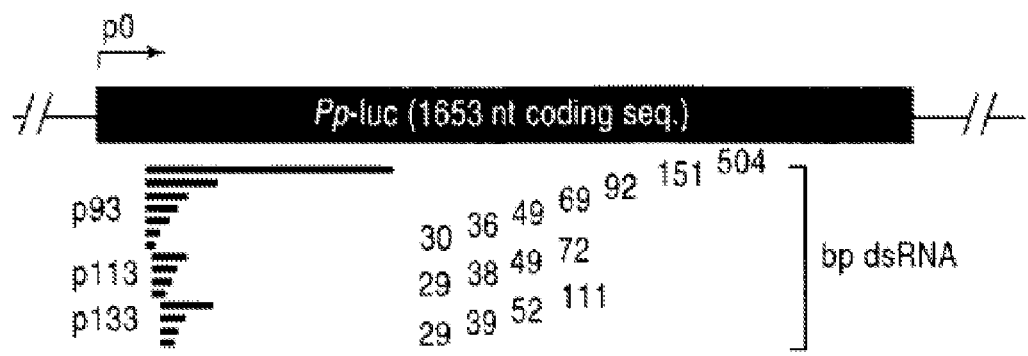

| | | |
|---|---|---|
| 7,078,196 B2 | 7/2006 | Tuschl et al. |
| 7,232,806 B2 | 6/2007 | Tuschl et al. |
| 8,097,710 B2 | 1/2012 | Baulcombe et al. |
| 8,101,584 B2 | 1/2012 | Kreutzer et al. |
| 2002/0086356 A1 | 7/2002 | Tuschl et al. |
| 2002/0114784 A1 | 8/2002 | Li et al. |
| 2002/0132257 A1 | 9/2002 | Giordano et al. |
| 2002/0137210 A1 | 9/2002 | Churikov |
| 2002/0160393 A1 | 10/2002 | Symonds et al. |
| 2002/0162126 A1 | 10/2002 | Beach et al. |
| 2003/0051263 A1 | 3/2003 | Fire et al. |
| 2003/0055020 A1 | 3/2003 | Fire et al. |
| 2003/0056235 A1 | 3/2003 | Fire et al. |
| 2003/0064945 A1 | 4/2003 | Akhtar et al. |
| 2003/0068301 A1 | 4/2003 | Draper et al. |
| 2003/0084471 A1 | 5/2003 | Beach et al. |
| 2003/0108923 A1 | 6/2003 | Tuschl et al. |
| 2003/0140362 A1 | 7/2003 | Macejak et al. |
| 2003/0148985 A1 | 8/2003 | Morrissey et al. |
| 2003/0153521 A1 | 8/2003 | McSwiggen |
| 2003/0171311 A1 | 9/2003 | Blatt et al. |
| 2003/0180756 A1 | 9/2003 | Shi et al. |
| 2003/0190654 A1 | 10/2003 | Heidenreich et al. |
| 2003/0206887 A1 | 11/2003 | Morrissey et al. |
| 2004/0001811 A1 | 1/2004 | Kreutzer et al. |
| 2004/0002153 A1 | 1/2004 | Monia et al. |
| 2004/0005593 A1 | 1/2004 | Lorens |
| 2004/0006035 A1 | 1/2004 | Macejak |
| 2004/0018999 A1 | 1/2004 | Beach et al. |
| 2004/0019001 A1 | 1/2004 | McSwiggen |
| 2004/0038921 A1 | 2/2004 | Kreutzer et al. |
| 2004/0053875 A1 | 3/2004 | Kreutzer et al. |
| 2004/0053876 A1 | 3/2004 | Turner et al. |
| 2004/0054156 A1 | 3/2004 | Draper et al. |
| 2004/0072779 A1 | 4/2004 | Kreutzer et al. |
| 2004/0086884 A1 | 5/2004 | Beach et al. |
| 2004/0096843 A1 | 5/2004 | Rossi et al. |
| 2004/0102408 A1 | 5/2004 | Kreutzer et al. |
| 2004/0121348 A1 | 6/2004 | Kreutzer et al. |
| 2004/0126791 A1 | 7/2004 | Wajant et al. |
| 2004/0137471 A1 | 7/2004 | Vickers et al. |
| 2004/0175703 A1 | 9/2004 | Kreutzer et al. |
| 2004/0191905 A1 | 9/2004 | Stevenson et al. |
| 2004/0192626 A1 | 9/2004 | McSwiggen et al. |
| 2004/0203145 A1 | 10/2004 | Zamore et al. |
| 2004/0214330 A1 | 10/2004 | Waterhouse et al. |
| 2004/0221337 A1 | 11/2004 | Baulcombe et al. |
| 2004/0224328 A1 | 11/2004 | Prydz et al. |
| 2004/0229266 A1 | 11/2004 | Tuschl et al. |
| 2004/0231016 A1 | 11/2004 | Wang et al. |
| 2004/0241854 A1 | 12/2004 | Davidson et al. |
| 2004/0248296 A1 | 12/2004 | Beresford et al. |
| 2004/0248835 A1 | 12/2004 | Krebs et al. |
| 2004/0259247 A1 | 12/2004 | Tuschl et al. |
| 2004/0259248 A1 | 12/2004 | Tuschl et al. |
| 2005/0026278 A1 | 2/2005 | Tuschl et al. |
| 2005/0100907 A1 | 5/2005 | Kreutzer et al. |
| 2005/0234006 A1 | 10/2005 | Tuschl et al. |
| 2005/0234007 A1 | 10/2005 | Tuschl et al. |
| 2005/0282764 A1 | 12/2005 | Bahramian et al. |
| 2006/0084621 A1 | 4/2006 | Vornlocher |
| 2006/0258608 A1 | 11/2006 | Meyers |
| 2007/0003960 A1 | 1/2007 | Tuschl et al. |
| 2007/0003961 A1 | 1/2007 | Tuschl et al. |
| 2007/0003962 A1 | 1/2007 | Tuschl et al. |
| 2007/0003963 A1 | 1/2007 | Tuschl et al. |
| 2007/0093445 A1 | 4/2007 | Tuschl et al. |
| 2008/0132461 A1 | 6/2008 | Tuschl et al. |
| 2008/0269147 A1 | 10/2008 | Tuschl et al. |
| 2009/0155174 A1 | 6/2009 | Tuschl et al. |
| 2009/0186843 A1 | 7/2009 | Tuschl et al. |
| 2010/0010207 A1 | 1/2010 | Tuschl et al. |
| 2010/0292456 A1 | 11/2010 | Tuschl et al. |
| 2010/0316703 A1 | 12/2010 | Tuschl et al. |
| 2011/0014123 A1 | 1/2011 | Tuschl et al. |
| 2011/0020234 A1 | 1/2011 | Tuschl et al. |
| 2011/0054159 A1 | 3/2011 | Tuschl et al. |
| 2011/0065109 A1 | 3/2011 | Tuschl et al. |
| 2011/0065773 A1 | 3/2011 | Tuschl et al. |
| 2011/0070162 A1 | 3/2011 | Tuschl et al. |
| 2011/0112283 A1 | 5/2011 | Tuschl et al. |
| 2011/0244446 A1 | 10/2011 | Tuschl et al. |
| 2011/0244568 A1 | 10/2011 | Tuschl et al. |
| 2011/0245318 A1 | 10/2011 | Tuschl et al. |
| 2011/0281931 A1 | 11/2011 | Tuschl et al. |
| 2011/0289611 A1 | 11/2011 | Tuschl et al. |
| 2011/0306651 A1 | 12/2011 | Tuschl et al. |
| 2012/0015042 A1 | 1/2012 | Tuschl et al. |
| 2012/0029061 A1 | 2/2012 | Tuschl et al. |
| 2012/0122111 A1 | 5/2012 | Tuschl et al. |
| 2013/0125259 A1 | 5/2013 | Tuschl et al. |

FOREIGN PATENT DOCUMENTS

| | | |
|---|---|---|
| CA | 2432350 | 7/2002 |
| DE | 199 56 568 A1 | 8/2000 |
| DE | 10155280.7 | 10/2001 |
| DE | 10158411.3 | 11/2001 |
| DE | 10160151.4 | 12/2001 |
| DE | 101 00 586 C1 | 4/2002 |
| DE | 10235620.3 | 8/2002 |
| DE | 200 23 125 U1 | 6/2003 |
| DE | 10160151 | 6/2003 |
| EP | 303516 B1 | 2/1989 |
| EP | 0649467 A1 | 4/1995 |
| EP | 0650493 A1 | 5/1995 |
| EP | 0 649 467 | 9/1998 |
| EP | 0126325.0 | 12/2000 |
| EP | 1 214 945 A2 | 6/2002 |
| EP | 1 144 623 | 8/2002 |
| EP | 1 144 623 B1 | 8/2002 |
| EP | 1 214 945 A3 | 9/2002 |
| EP | 1309726 B1 | 5/2003 |
| EP | 0 983 370 B1 | 9/2003 |
| EP | 1407044 B1 | 4/2004 |
| EP | 1230375 B1 | 7/2005 |
| EP | 1 352 061 | 5/2006 |
| EP | 2348133 A1 | 7/2011 |
| EP | 2348134 A1 | 7/2011 |
| EP | 2351852 A1 | 8/2011 |
| GB | 9827152.1 | 12/1998 |
| GB | 2 349 885 A | 11/2000 |
| GB | 2 362 885 A | 12/2001 |
| GB | 2 370 275 A | 6/2002 |
| GB | 2 353 282 | 4/2003 |
| RU | 2322500 C2 | 4/2008 |
| WO | 9110671 A1 | 7/1991 |
| WO | 9219732 A1 | 11/1992 |
| WO | 94/01550 A1 | 1/1994 |
| WO | WO9401550 | 1/1994 |
| WO | 94/15645 | 7/1994 |
| WO | 94/21767 | 9/1994 |
| WO | 9507981 A1 | 3/1995 |
| WO | 9640964 A2 | 12/1996 |
| WO | 97/11170 | 3/1997 |
| WO | 97/11170 A1 | 3/1997 |
| WO | 9743431 A1 | 11/1997 |
| WO | 9746570 A1 | 12/1997 |
| WO | 9805770 A2 | 2/1998 |
| WO | 98/53083 | 11/1998 |
| WO | 99/14226 | 3/1999 |
| WO | 99/15682 | 4/1999 |
| WO | 99/32619 A1 | 7/1999 |
| WO | 99/49029 A1 | 9/1999 |
| WO | 99/53050 A1 | 10/1999 |
| WO | 9954459 A2 | 10/1999 |
| WO | 99/61631 A1 | 12/1999 |
| WO | 00/01846 A2 | 1/2000 |
| WO | 00/31271 | 6/2000 |
| WO | 00/32619 A1 | 6/2000 |
| WO | 00/44895 A1 | 8/2000 |
| WO | 0044914 A1 | 8/2000 |
| WO | 00/63364 A2 | 10/2000 |
| WO | 00/63364 A3 | 10/2000 |

(56) References Cited

FOREIGN PATENT DOCUMENTS

| WO | 0136646 A1 | 5/2001 |
|---|---|---|
| WO | 01/68826 A2 | 9/2001 |
| WO | 0168836 A2 | 9/2001 |
| WO | 01/75164 A2 | 10/2001 |
| WO | 01/92513 A1 | 12/2001 |
| WO | 02/44321 A2 | 6/2002 |
| WO | 02/055692 A2 | 7/2002 |
| WO | 02/055692 A3 | 7/2002 |
| WO | 02/055693 | 7/2002 |
| WO | 02/059300 A2 | 8/2002 |
| WO | 02/059300 A3 | 8/2002 |
| WO | 02/061034 | 8/2002 |
| WO | 03/029459 A2 | 4/2003 |
| WO | 03/033700 A1 | 4/2003 |
| WO | 03/035869 | 5/2003 |
| WO | 03/062394 A2 | 7/2003 |
| WO | 03/064621 | 8/2003 |
| WO | 03/099298 A1 | 12/2003 |
| WO | 03/103600 | 12/2003 |
| WO | 03/106630 | 12/2003 |
| WO | 03/106631 | 12/2003 |
| WO | 2004/007718 | 1/2004 |
| WO | 2004/014933 | 2/2004 |
| WO | 2004015107 A2 | 2/2004 |
| WO | 2004/027030 | 4/2004 |
| WO | 2004/029212 | 4/2004 |
| WO | 2004/042029 | 5/2004 |
| WO | 2004/044131 | 5/2004 |
| WO | 2004/045543 | 6/2004 |
| WO | 2004/046324 | 6/2004 |
| WO | 2004/063375 | 7/2004 |
| WO | 2004/065600 | 8/2004 |
| WO | 2004/065613 | 8/2004 |
| WO | 2004/076622 | 9/2004 |
| WO | 2004/111191 | 12/2004 |

OTHER PUBLICATIONS

Sanchez-Alvarado et al., "Double-stranded RNA specifically disrupts gene expression during planarian regeneration", Proc. Natl. Acad. Sci. USA, 1999, vol. 96, pp. 5049-5054.
Schaefer, "Revolutions in rapid amplification of cDNA ends: new strategies for polymerase chain reaction cloning of full-length cDNA ends", Analytical Biochemistry, 1996, vol. 227, pp. 255-273.
Scherer et al., "Approaches for the sequence-specific knockdown of mRNA", Nat. Biotechnol., 2003, vol. 21, No. 12, pp. 1457-1465.
Schiebel et al., "Isolation of an RNA-directed RNA polymerase-specific cDNA clone from tomato", Plant Cell, 1998, vol. 10, pp. 2087-2101.
Shi Y. And C. Mello: "A CBP/p300 homolog specifies multiple different pathways in *Caenorhabditis elegans*", Genes & Development, vol. 12, No. 7, pp. 943-955, Apr. 1, 1998.
Sioud et al., "High-throughput analysis of microRNA gene espression using sensitive probes", RNA Silencing: Methods and Protocols, 2005, vol. 309, pp. 311-320, Humana Press.
Skripkin, E. et al.: "Psoralen crosslinking between human immunodeficiency virus type 1 RNA and primer tRNA3Lys", Nucleic Acids Research, 1996, vol. 24, No. 3, pp. 509-514.
Slack et al., "The lin-41 RBCC gene acts in the *C.elegans* heterochronic pathway between the let-7 regulatory RNA and the LIN-29 transcription factor", Mol. Cell, Apr. 2000, vol. 5, No. 4, pp. 659-669.
Sledz, C. A. et al.: "Activation of the interferon system by short-interfering RNAs", Nature Cell Biology, vol. 5, No. 9, pp. 834-839, Sep. 2003.
Smith et al., "Total silencing by intron-spliced hairpin RNAs", Nature, 2000, vol. 407, pp. 319-320.
Soutschek, J. et al.: "Therapeutic silencing of an endogenous gene by systemic administration of modified siRNAs", Nature, Nov. 11, 2004, vol. 432, pp. 173-178.
Tao et al., "Drug target validation: Lethal infection blocked by inducible peptide", PNAS, 2000, vol. 97, No. 2, pp. 783-786.
Tuschl et al., "Importance of exocyclic base functional groups of central core guanosines for hammerhead ribozyme activity", Biochemistry, 1993, vol. 32, pp. 11658-11668.
Tuschl et al., "Selection in vitro of novel ribozymes from a partially randomized U2 and U6 snRNA library", Embo. J., 1998, vol. 17, pp. 2637-2650.
Tuschl, "Mammalian RNA interference", RNAi: A Guide to Gene Silencing, 2003, Chapt. 13, pp. 265-295.
U.S. Appl. No. 60/130,377, filed Apr. 21, 1999.
U.S. Appl. No. 60/117,635 dated Jan. 28, 1999.
U.S. Appl. No. 60/193,594 dated Mar. 30, 2000.
U.S. Appl. No. 60/265,232 dated Jan. 31, 2001.
U.S. Appl. No. 60/189,739, dated Mar. 16, 2000.
U.S. Appl. No. 60/243,097, dated Oct. 24, 2000.
Ueda et al., "Phosphorothioate-containing RNAs show mRNA activity in the prokaryotic translation systems in vitro", Nucleic Acids Research, 1991, vol. 19, No. 3, pp. 547-552.
Uhlmann, E. et al.: "Antisense Oligonucleotides: A new therapeutic principle", Chemical Reviews, US, American Chemical Society, Easton, vol. 90, No. 4, Jun. 1, 1990, pp. 543-584, XP000141412, ISSN: 0009-2665.
Verma et al., "Modified oligonucleotides: synthesis and strategy for users", Annu. Rev. Biochem., 1998, vol. 67, pp. 99-134.
Vinayak et al., "Chemical synthesis of RNA using fast oligonucleotide deprotection chemistry", Nucleic Acids Research, 1992, vol. 20, No. 6, pp. 1265-1269.
Voinnet et al., "A viral movement protein prevents spread of the gene silencing signal in *Nicotiana benthamiana*", Cell, 2000, vol. 103, pp. 157-167.
Voinnet, O. and D. C. Baulcombe: "Systemic signalling in gene silencing", Nature, vol. 389, p. 553, Oct. 9, 1997.
Wahls, "RNA associated with a heterodimeric protein that activates a meiotic homologous recombination hot spot: RL/RT/PCR strategy for cloning any unknown RNA or DNA", PCR Methods and Applications, 1994, vol. 3, pp. 272-277.
Wang et al., "Relative stabilities of triple helices composed of combinations of DNA, RNA and 2'-O-methyl-RNA backbones: chimeric circular oligonucleotides as probes", Nuc. Acids Res., 1995, vol. 23, No. 7, pp. 1157-1164.
Wargelius et al., "Double-stranded RNA induces specific developmental defects in zebrafish embryos", Biochem. Biophys. Res. Commun., Sep. 16, 1999, vol. 263, No. 1, pp. 156-161.
Written Demand for Invalidation Trial against Japanese Patent No. 4095895, dated Jul. 8, 2011 (Complete English Translation).
Wu-Scharf et al., "Transgene and transposon silencing in Chlamydomonas reinhardtii by a DEAH-Box RNA helicase", Science, 2000, vol. 290, pp. 1159-1162.
Yang et al., "Evidence that processed small dsRNAs may mediate sequence-specific mRNA degradation during RNAi in *Drosophila* embryos", Curr. Biol., 2000, vol. 10, pp. 1191-1200.
Zamore et al., "The Pumilio-RNA interaction: a single NA-binding domain monomer recognizes a bipartite target sequence", Biochemistry, 1999, vol. 38, pp. 596-604.
Zeng, Yan and B. R. Cullen: "RNA interference in human cells is restricted to the cytoplasm", RNA, 2002, vol. 8, pp. 855-860.
Zhang et al., "Regulation of ribonuclease III processing by double-helical sequence antideterminants", Proc. Natl. Acad. Sci. USA, 1997, vol. 94, pp. 13437-13441.
Zhang et al., "Targeted gene silencing by small interfering RNA-based knock-down technology", Current Pharmaceutical Biotechnology, 2004, vol. 5, pp. 1-7.
Zhao et al., "Double-stranded RNA injection produces nonspecific defects in zebrafish", Dev. Biol., 2001, vol. 229, pp. 215-223.
Zheng, X. and P. C. Bevilacqua: "Activation of the protein kinase PKR by short double-stranded RNAs with single stranded tails", RNA (2004), vol. 10, pp. 1934-1945.
Confidential Settlement Agreement and Mutual Release dated Mar. 15, 2011 as provided in Exhibit 10.2 of Alnylam Pharmaceuticals Inc.'s 10-Q SEC Quarterly Report filed on May 5, 2011.
Interlocutory Decision Issued by Opposition Division in Opposition Proceedings to EP 1309726 dated Mar. 30, 2012.

(56) References Cited

OTHER PUBLICATIONS

Ho et al. "Mapping of RNA Accessible Sites for Antisense Experiments with Oligonucleotide Libraries". Nature Biotechnology, vol. 16, Jan. 1998, pp. 59-63.
Declaration of Wolfgang Weiss, Under 35 U.S.C. §1.132, dated Jan. 7, 2009.
Case 1:11-cv-10484-PBS. Document 60. Memorandum in Opposition to the Official Capacity Defendant's Motion to Dismiss University of Utah's Second Amended complaint. Filed Mar. 21, 2012.
Case 1:11-cv-10484-PBS. Document 61. Memorandum in Opposition to Defendant's Motion to Dismiss University of Utah's Second Amended Complaint. Filed Mar. 21, 2012.
Case 1:11-cv-10484-PBS. Document 62 and Associated Exhibits. Declaration of Steve W. Berman in Support of Memoranda in Opposition to All Defendant's Motions to Dismiss University of Utah's Second Amended Complaint. Filed Mar. 21, 2012.
Case 1:11-cv-10484-PBS. Document 64. Reply in Support of Defendant's Motion to Dismiss University of Utah's Second Amended Complaint. Filed Apr. 18, 2012.
Case 1:11-cv-10484-PBS. Document 65. Reply in Support of Official Capacity Defendant's Motion to Dismiss University of Utah's Second Amended Complaint. Filed Apr. 18, 2012.
Case 1:11-cv-10484-PBS. Document 66. Surreply in Opposition to Defendants' Motion to Dismiss University of Utah's Second Amended Complaint. Filed May 9, 2012.
Further arguments submitted by Sirna Therapeutics (Opponent 1) in opposition to EP1407044, dated Sep. 29, 2010.
Further submission by patentee in EP1407044, dated Nov. 12, 2010.
Further submission by Sirna Therapeutics (Opponent 1) in opposition to EP1407044, dated Nov. 10, 2010.
Further submission by Sirna Therapeutics (Opponent 1) in opposition to EP1407044, dated Nov. 3, 2010.
Grasby, J. A. et al.: "Purine Functional Groups in Essential Residues of the Hairpin Ribozyme Required for Catalytic Cleavage of RNA", Biochemistry, Mar. 28, 1995, vol. 34, No. 12, pp. 4068-4076.
Griffey, R. H. et al.: 2'-O-Aminopropyl Ribonucleotides: A Zwitterionic Modification That Enhances the Exonuclease Resistance and Biological Activity of Antisense Oligonucleotides, J Med Chem, Dec. 20, 1996, vol. 39, No. 26, pp. 5100-5109.
Grishok et al., VI. RNAi and Development References, Advances in Genetics, vol. 46: pp. 340-360 (2002).
Gryaznov S. M. and R. L. Letsinger: "Template controlled coupling and recombination of oligonucleotide blocks containing thiophosphoryl groups", Nucleic Acids Res, Mar. 25, 1993, vol. 21, No. 6, pp. 1403-1408.
Ha, I. et al.: "A bulged lin-4/lin-14 RNA duplex is sufficient for *Caenorhabditis elegans* lin-14 temporal gradient formation", Genes Development, Dec. 1, 1996; vol. 10, No. 23, pp. 3041-3050.
Hamilton et al., "A novel humanised antibody against Prostate Specific Membrane Antigen (PSMA) for in vivo targeting and therapy", Proceedings of the American Association for Cancer Research, 1998, Poster Presentation No. 2997.
Harada et al., "Absence of the Type I IFN System in EC Cells: Transcriptional Activator (IRF-1) and Repressor (IRF-2) Genes are Developmentally Regulated," Cell, vol. 83, pp. 303-312, 1990.
Harborth et al. "Identification of Essential Genes in Cultured Mammalian Cells Using Small Interfering RNAs". J. Cell Science 114: 4457-4565. (2001).
Hedges S. B., "The Origin and Evolution of Model Organisms", Nature, vol. 3; Nov. 2002.
Ho et al., "Potent antisense oligonucleotides to the human multidrug resistance-1 mRNA are rationally selected by mapping RNA-accessible sites with oligonucleotide libraries", Nucleic Acids Research, 1996, vol. 24, No. 10, pp. 1901-1907.
Hoke, G. D. et al.: Effects of phosphorothioate capping on antisense oligonucleotide stability, hybridization and antiviral efficacy versus herpes simplex virus infection, Nucleic Acids Res, Oct. 25, 1991, vol. 19, No. 20, pp. 5743-5748.

Horn, T. et al.: "Chemical synthesis and characterization of branched oligodesoxyribonucleotides (bDNA) for use as signal amplifiers in nucleic acid quantification assays", Nucleic Acids Research, 1997, vol. 25, No. 23, pp. 4842-4849.
Hornung, V. et al.: "Sequence-specific potent induction of IFN-Alfa by short interfering RNA in plasmacytoid dendritic cells trough TLR7", Nature Medicine, vol. 11, No. 3, pp. 263-270, Mar. 2005.
Hossbach et al., "Gene silencing with siRNA duplexes composed of target-mRNA-complementary and partially palindromic or partially complementary single-stranded siRNAs", RNA Biology, 2006, vol. 3, No. 2, pp. 82-89.
Hunter T. et al.: "The Characteristics of Inhibition of Protein Synthesis by Double-Stranded Ribonucleic Acid in Reticulocyte Lysates", The Journal of Biological Chemistry, vol. 250, No. 2, pp. 409-417, Jan. 25, 1975.
Interlocutory decision issued by Opposition Division in opposition proceedings to EP1407044, dated Feb. 15, 2011.
International Search Report for PCT/DE00/00244 dated Jun. 20, 2000.
International Search Report for PCT/EP01/13968, mailed Jul. 29, 2003.
Jacobsen et al., "Disruption of an RNA helicase/RNase III gene in *Arabidopsis* causes unregulated cell division in floral meristems", Development, 1999, vol. 126, pp. 5231-5243.
Jensen et al., "Taming of transposable elements by homology-dependent gene silencing", Nat. Genet., 1999, vol. 21, pp. 209-212.
JI, "The mechanism of RNase III action: how dicer dices", Current Topics in Microbiology and Immunology, 2008, vol. 320, pp. 99-116.
Judge, A. D. et al.: "Sequence-dependent stimulation of the mammalian innate immune response by synthetic siRNA", Nature Biotechnology, vol. 23, No. 4, pp. 457-462, Apr. 2005.
Kabanov et al., "DNA complexes with polycations for the delivery of genetic material into cells", Bioconjugate Chem., 1995, vol. 6, pp. 7-20.
Kaufman, R. J., PNAS, Oct. 12, 1999, vol. 96, No. 21, pp. 11693-11695.
Kitabwalla M., Ruprecht R.: "RNA Interference—A New Weapon Against HIV and Beyond", N. Engl. J. Med., vol. 347, No. 17, pp. 1364-1367 (2002).
Krinke and Wulff, "The cleavage specificity of RNase III," Nucleic Acids Research, vol. 18, pp. 4809-4815 (1990).
Kuwabara et al., "RNAi—prospects for a general technique for determining gene function", Parasitology Today, 2000, vol. 16, pp. 347-349.
Lee et al., "Distinct roles for *Drosophila* dicer-1 and dicer-2 in the siRNA/miRNA silencing pathways", Cell, 2004, vol. 117, pp. 69-81.
Lehmann et al., "The Importance of Internal Loops within RNA Substrates of ADAR1," Journal of Molecular Biology, 291: 1-13 (1999).
Li et al., "Double-stranded RNA injection produces null phenotypes in zebrafish", Dev. Biol., 2000, vol. 217, No. 2, pp. 394-405.
Li et al.: "Double-stranded RNA injection produces null phenotypes in zebrafish," Dev. Biology Volume, vol. 210, p. 238, Jun. 1, 1999.
Libonati et al., "Revisiting the action of bovine ribonuclease A and pancreatic-type ribonucleases on double-stranded RNA", Mol. Cell. Biochem., 1992, vol. 117, No. 2, pp. 139-151.
Lingel et al. "Nucleic acid 3'-end recognition by the Argonaute2 PAZ domain". Nature Structural & Molecular Biology. vol. 11. No. 6. pp. 576-577. Jun. 2004.
Lipinski, C. A. et al.: "Experimental and computational approaches to estimate solubility and permeability in drug discovery and development settings", Adv. Drug Delivery Reviews 23, pp. 3-25, 1997.
Liu et al., "Mapping the 5' and 3' ends of Tetrahymena thermophila mRNAs using RNA ligase mediated amplification of cDNA ends (RLM-RACE)", Nucleic Acids Research, 1993, vol. 21, No. 21, pp. 4954-4960.
Lu et al. (2008) Methods in Molecular Biology, vol. 437: Drug Delivery Systems—Chapter 3: Delivering Small Interfering RNA for Novel Therapeutics.
Lu et al., "Delivering small interfering RNA for novel therapeutics", Methods in Molecular Biology, vol. 437, Drug Delivery Systems, Chapter 3, pp. 93-107 (2008).

(56) References Cited

OTHER PUBLICATIONS

Lucy et al., "Suppression of post-transcriptional gene silencing by a plant viral protein localized in the nucleus", EMBO J., 2000, vol. 19, pp. 1672-1680.
Ma et al., "Structural basis for overhang-specific small interfering RNA recognition by the PAZ domain," Nature, May 20, 2004, vol. 429, pp. 318-322.
Ma, M. Y-X. et al.: "Design and Synthesis of RNA Miniduplexes via a Synthetic Linker Approach", Biochemistry, Feb. 23, 1993; vol. 32, No. 7, pp. 1751-1758.
Mahato et al., "Modulation of gene expression by antisense and antigene oligodeoxynucleotides and small interfering RNA", Expert Opinion on Drug Delivery, 2005, vol. 2, No. 1, pp. 3-28.
Main request for dismissal of appeals in the opposition proceeding against European Patent No. 1 407 044 (Application No. 01985833.1), submitted by patentee, dated Nov. 10, 2011, 61 pages.
Majumdar, A. et al.: "Targeted gene knockout mediated by triple helix forming oligonucleotides", Nat Genet Oct. 1998; vol. 20, No. 2, pp. 212-214.
Martinez, J. and T. Tuschl: "RISC is a 5' phosphomonoester-producing RNA endonuclease", Genes & Dev., vol. 18, No. 9, pp. 975-980, 2004.
Matsuda et al., "Molecular cloning and characterization of a novel human gene (HERNA) which encodes a putative RNA-helicase", Biochimica et Biophysica Acta, 2000, vol. 1490, pp. 163-169.
Meister, G., "RNA Interference in the Nucleus," Science, vol. 321, Jul. 25, 2008, pp. 496-541.
Mello, "Return to the RNAi World: Rethinking Gene Expression and Evolution," Nobel Lecture, Dec. 8, 2006.
Milhaud, P. G. et al.: "Free and Liposome-Encapsulated Double-Stranded RNAs as Inducers of Interferon, Interleukin-6 and Cellular Toxicity", Journal of Interferon Research, 1991, vol. 11, pp. 261-265.
Milligan et al., "Synthesis of small RNAs using T7 RNA polymerase", Methods in Enzymology, 1989, vol. 180, pp. 51-62.
Minks, M. A.: "Structural Requirements of Double-stranded RNA for the Activation of 2',5'-Oligo(A) Polymerase and Protein Kinase of Interferon-treated HeLa Cells", The Journal of Biological Chemistry, vol. 254, No. 20, issue of Oct. 25, pp. 10180-10183, 1979.
Misquitta et al., "Targeted disruption of gene function in *Drosophila* by RNA interference (RNA-i): a role for nautilus in embryonic somatic muscle formation", Proc. Natl. Acad. Sci. USA, 1999, vol. 96, pp. 1451-1456.
Montgomery et al., "RNA as a target of double-stranded RNA-mediated genetic interferece in Caenorhabditis elegans", Proc. Natl. Acad. Sci. USA, 1998, vol. 95, pp. 15502-15507.
Moss, E. G. et al., "The Cold Shock Domain Protein LIN-28 Controls Developmental Timing in *C. elegans* and is Regulated by the LIN-4 RNA", Cell, vol. 88, Mar. 7, 1997, 637-646.
Mourrain et al., "*Arabidopsis* SGS2 and SGS3 genes required for posttranscriptional gene silencing and natural virus resistance", Cell, 2000, vol. 101, pp. 533-542.
Nakamura, H. et al.: "How does RNase H recognize a DNA-RNA hybrid", Proc. Natl. Acad. (1991), vol. 88, pp. 11535-11539.
Nakano et al., "RNA interference for the organizer-specific gene Xlim-1 in *Xenopus* embryos", Biochem. Biophys. Res. Commun., 2000, vol. 274, pp. 434-439.
Nanduri, S. et al.: "Structure of the double-stranded RNA-binding domain of the protein kinase PKR reveals the molecular basis of its dsRNA-mediated activation", The EMBO Journal, vol. 17, No. 18, pp. 5458-5465 (1998).
Napoli, C. et al.: "Introduction of a Chimeric Chalcone Synthase Gene into Petunia Results in Reversible Co-Suppression of Homologous Genes in trans", The Plant Cell, vol. 2, Apr. 1990, pp. 279-289.
Nielsen P. et al.: "A novel class of conformationally restricted oligonucleotide analogues: synthesis of 2',3'40 -bridged monomers and RNA-selective hybridisation", J. Chem. Commun. 1997; pp. 825-826.
Nikiforov, T. T. and B. A. Connolly: "Oligodeoxynucleotides containing 4-thiothymidine and 6-thiodeoxyguanosine as affinity labels for the Eco RV restriction endonuclease and modification methylase", Nucleic Acids Res, Mar. 25, 1992, vol. 20, No. 6, pp. 1209-1214.
Oates, A. C. et al.: Too Much Interference: Injection of Double-Stranded RNA has Nonspecific Effects in the Zebrafish Embryo, Developmental Biology, vol. 224, 2000, pp. 20-28.
Oelgeschlager et al., "The evolutionarily conserved BMP-binding protein twisted gastrulation promotes BMP signalling", Nature, 2000, vol. 405, pp. 757-763.
Opposition paper submitted by BASF (Opponent 3) in EP1309726, dated Sep. 2, 2010.
Opposition Paper Submitted by BASF (Opponent 3) in Response to the Summons to Attend Oral Proceedings in EP 1309726, dated Jan. 27, 2012.
Opposition paper submitted by BASF SE (Opponent 4) in EP 1407044 dated Jun. 19, 2008.
Opposition paper submitted by Pfizer (Opponent 2) in EP 1407044, dated Jun. 19, 2008.
Opposition paper submitted by Sanofi-Aventis (Opponent 1) in EP1309726, Sep. 2, 2010.
Opposition Paper Submitted by Sanofi-Aventis (Opponent 1) in Response to the Summons to Attend Oral Proceedings in EP 1309726 dated Jan. 25, 2012.
Opposition paper submitted by Sarah E. Rogues (Opponent 3) in EP1407044 dated Jun. 18, 2008.
Opposition paper submitted by Silence Therapeutics (Opponent 2) in EP1309726, dated Sep. 2, 2010.
Opposition Paper Submitted by Silence Therapeutics (Opponent 2) in Response to the Summons to Attend Oral Proceedings in EP 1309726 dated Jan. 27, 2012.
Opposition paper submitted by Silence Therapeutics (Opponent 5) in EP1407044 dated Jun. 19, 2008.
Opposition paper submitted by Sirna Therapeutics (Opponent 1) in EP 1407044, dated Jun. 10, 2008.
Pan et al., "In vitro selection of RNAs that undergo autolytic cleavage with Pb2+", Biochemistry, 1992, vol. 31, No. 16, pp. 3887-3895.
Papers filed in EPO in opposition to European Patent No. EP 1 144 623 by Aventis Pharma Deustschland GmbH on May 28, 2003.
Papers filed in EPO in opposition to European Patent No. EP 1 144 623 by Dr. Martin Grund on May 28, 2003.
Papers filed in EPO in opposition to European Patent No. EP 1 144 623 by SiRNA Therapeutics Inc. on May 19, 2003.
Parrish et al., "Functional anatomy of a dsRNA trigger: differential requirement for the two trigger strands in RNA interference", Mol. Cell, 2000, vol. 6, pp. 1077-1087.
Partial European Search Report mailed Sep. 27, 2007 for Application No. 07014533.
Patentee's main request and counterargument to the opponents objections in EP1407044, dated Mar. 26, 2009.
Patentee's Submission in Response to the Summons to Attend Oral Proceedings in EP 1309726 dated Jan. 27, 2012.
Pegram, M. D. et al.: "Phase II Study of Receptor-Enhanced Chemosensitivity Using Recombinant Humanized Anti-p185HER2/neu Monoclonal Antibody Plus Cisplatin in Patients With HER2-neu Overexpressing Metastasic Breast Cancer Refractory to Chemotherapy Treatment", J. Clin. Oncol. Aug. 1998, vol. 16, No. 8, pp. 2659-2671.
Pei, Y. and T. Tuschl: "On the art of identifying effective and specific siRNAs", Nature Methods, vol. 3, No. 9, Sep. 2006, pp. 670-676.
Pelissier et al., "A DNA target of 30 by is sufficient for RNA-directed methylation", RNA, 2000, vol. 6, pp. 55-65.
Perler, F. B.: "InBase: the Intein Database", New England Biolabs Inc., Nucleic Acids Research 2002, vol. 30, No. 1, 383-384.
Plasterk et al., "The silences of the genes", Curr. Opin. Genet., Dev., 2000, vol. 10, pp. 562-567.
Preliminary and non-binding opinion issued by Opposition Division regarding EP1407044, dated May 6, 2010.
Ratcliff et al., "Gene silencing without DNA. RNA-mediated cross-protection between viruses", Plant Cell, 1999, vol. 11, pp. 1207-1216.
Register extract for WO 01/75164 (printed Feb. 18, 2008).
Reply Brief filed by the patentee to dismiss the Appeals in the opposition proceedings in EP1407044, dated Nov. 10, 2011.

(56) References Cited

OTHER PUBLICATIONS

Reprint of Thomas Tuschl's email dated Apr. 5, 2000 (printed Jan. 11, 2010).
Response to Notice of Opposition against EP1309726, filed by patentee, dated Jul. 4, 2011.
Robertson, "*Escherichia coli* ribonuclease III cleavage sites", Cell, 1982, vol. 30, pp. 669-672.
Robertson, "*Escherichia coli* ribonuclease III", Methods Enzymol., 1990, vol. 181, pp. 189-202.
Roitt et al., Immunology, Third Edition, 1993, p. 15.8.
Case 1:09-cv-11116-PBS. Deposition Testimony of Anne Collins; Oct. 30, 2009.
Case 1:09-cv-11116-PBS. Deposition Testimony of Anne Collins; Oct. 30, 2009; associated Exhibits previously marked 2 through 4 and 530 through 545.
Case 1:09-cv-11116-PBS. Deposition Testimony of David Bartel; Nov. 23, 2009.
Case 1:09-cv-11116-PBS. Deposition Testimony of David Bartel; Nov. 23, 2009; associated Exhibits 771 through 775.
Case 1:09-cv-11116-PBS. Deposition Testimony of Helen Lockhart; day 1; Nov. 24, 2009.
Case 1:09-cv-11116-PBS. Deposition Testimony of Helen Lockhart; day 1; Nov. 24, 2009; associated Exhibits 850 through 877.
Case 1:09-cv-11116-PBS. Deposition Testimony of Helen Lockhart; day 2; Dec. 15, 2009.
Case 1:09-cv-11116-PBS. Deposition Testimony of Helen Lockhart; day 2; Dec. 15, 2009; associated Exhibits 902 through 914.
Case 1:09-cv-11116-PBS. Deposition Testimony of Monica Chin Kitts; Dec. 9, 2009.
Case 1:09-cv-11116-PBS. Deposition Testimony of Monica Chin Kitts; Dec. 9, 2009; associated Exhibits 231 through 248.
Case 1:09-cv-11116-PBS. Deposition Testimony of Patricia Granahan; Nov. 17, 2009.
Case 1:09-cv-11116-PBS. Deposition Testimony of Patricia Granahan; Dec. 9, 2009; associated Exhibits 637 through 645.
Case 1:09-cv-11116-PBS. Deposition Testimony of Phillip Sharp; Nov. 30, 2009.
Case 1:09-cv-11116-PBS. Deposition Testimony of Phillip Sharp; Nov. 30, 2009; associated Exhibits 785 through 789.
Case 1:09-cv-11116-PBS. Deposition Testimony of Phillip D. Zamore, PhD.; Nov. 25, 2009, associated Exhibits 781-784.
Case 1:09-cv-11116-PBS. Deposition Testimony of Phillip D. Zamore, PhD.; Nov. 24, 2009, associated Exhibits 776-780.
Case 1:09-cv-11116-PBS. Deposition Testimony of Robert Murray; Oct. 26, 2009.
Case 1:09-cv-11116-PBS. Deposition Testimony of Robert Murray; Oct. 26, 2009; associated Exhibits 18 through 26.
Case 1:09-cv-11116-PBS. Deposition Testimony of Sayda Elbashir; Nov. 20, 2009.
Case 1:09-cv-11116-PBS. Deposition Testimony of Sayda Elbashir; Nov. 20, 2009; associated Exhibits 163 through 168.
Case 1:09-cv-11116-PBS. Deposition Testimony of Thomas Tuschl; Day 1; Nov. 6, 2009.
Case 1:09-cv-11116-PBS. Deposition Testimony of Thomas Tuschl; Day 1; Nov. 6, 2009; associated Exhibits 27 through 58.
Case 1:09-cv-11116-PBS. Deposition Testimony of Thomas Tuschl; Day 2; Nov. 19, 2009.
Case 1:09-cv-11116-PBS. Deposition Testimony of Thomas Tuschl; Day 2; Nov. 19, 2009; associated Exhibits 150 through 162.
Case 1:09-cv-11116-PBS. Deposition Testimony of Winfried Lendeckel; Nov. 14, 2009.
Case 1:09-cv-11116-PBS. Deposition Testimony of Winfried Lendeckel; Nov. 14, 2009; associated Exhibits 108 through 114.
Case1:11-cv-10484-PBS—Document 1-4—Exhibit 4 associated with plaintiffs complaint, filed Mar. 22, 2011.
Case1:11-cv-10484-PBS—Document 1-5—Exhibit 5 associated with plaintiffs complaint, filed Mar. 22, 2011.
Case1:11-cv-10484-PBS—Document 1-6—Exhibit 6 associated with plaintiffs complaint, filed Mar. 22, 2011.
Case1:11-cv-10484-PBS—Document 1-7—Exhibit 7 associated with plaintiffs complaint, filed Mar. 22, 2011.
Case1:11-cv-10484-PBS—Document 1-8—Exhibit 8 associated with plaintiffs complaint, filed Mar. 22, 2011.
Case1:11-cv-10484-PBS—Document 1-9—Exhibit 9 associated with plaintiffs complaint, filed Mar. 22, 2011.
Case1:11-cv-10484-PBS—Document 30. Defendants' Motion to Dismiss the University of Utah's First Amended Complaint. Filed Oct. 31, 2011.
Case1:11-cv-10484-PBS—Document 31. Memorandum in Support of Defendants' Motion to Dismiss the University of Utah's First Amended Complaint. Filed Oct. 31, 2011.
Case1:11-cv-10484-PBS—Document 32. Declaration of Alan J. Heinrich with Exhibits 1-3. Filed Oct. 31, 2011.
Case1:11-cv-10484-PBS—Document 33. University of Massachusetts' Motion to Dismiss University of Utah's First Amended Complaint. Filed Oct. 31, 2011.
Case1:11-cv-10484-PBS—Document 34. Memorandum in Support of University of Massachusetts' Motion to Dismiss University of Utah's First Amended Complaint. Filed Oct. 31, 2011.
Case1:11-cv-10484-PBS—Document 41. Plaintiff's Unopposed Motion for Leave to Amend Complaint. Filed Dec. 22, 2011.
Case1:11-cv-10484-PBS—Document 42. Second Amended Complaint. Filed Dec. 27, 2011.
Case1:11-cv-10484-PBS—Document 54. Defendants' Motion to Dismiss the University of Utah's Second Amended Complaint. Filed Feb. 10, 2012.
Case1:11-cv-10484-PBS—Document 55. Memorandum in Support of Defendants' Motion to Dismiss the University of Utah's Second Amended Complaint. Filed Feb. 10, 2012.
Case1:11-cv-10484-PBS—Document 56. Declaration of Alan J. Heinrich with Exhibits 1-3. Filed Feb. 10, 2012.
Case1:11-cv-10484-PBS—Document 8. First Amended Complaint. Filed Jul. 6, 2011.
Chanfreau et al., "Recognition of a conserved class of RNA tetraloops by *Saccharomyces cerevisiae* RNase III", Proc. Natl. Acad. Sci. USA, 1997, vol. 97, pp. 3143-3147.
Chen, M. et al.: "A universal plasmid library encoding all permutations of small interfering RNA", PNAS, 2005, vol. 102, pp. 2356-2361.
Chien P. Y. et al.: "Novel cationic cardiolipin analogue-based liposome for efficient DNA and small interfering RNA delivery in vitro and in vivo", Cancer Gene Therapy, 12:321-328 (2005).
Clemens, "PKR—a protein kinase regulated by double-stranded RNA", Int. J. Biochem., Cell Biol., 1997, vol. 29, No. 7, pp. 945-949.
Cogoni et al., "Homology-dependent gene silencing in plants and fungi: a number of variations on the same theme", Curr. Opin. Microbiol., 1999, vol. 2, pp. 657-662.
Couzin, J., "Breakthrough: Small RNAs Make Big Splash", Science, vol. 298, pp. 2296-2297, Dec. 2002.
Czauderna et al., "Structural variations and stabilising modifications of synthetic siRNAs in mammalian cells", Nucleic Acids Research, 2003, vol. 31, No. 11, pp. 2705-2716.
Dalmay et al., "An RNA-dependent RNA polymerase gene in *Arabidopsis* in required for posttranscriptional gene silencing mediated by a transgene but not by a virus", Cell, 2000, vol. 101, pp. 543-553.
De Fougerolles et al., "siRNA and the lung: research tool or therapeutic drug?", Current Opinion in Pharmacology, 2008, vol. 8, pp. 280-285.
Declaration of Rachel Meyers, Ph.D. Under 35 U.S.C. §1.132, dated Jul. 24, 2009.
Declaration of Thomas Tuschl Under 35 U.S.C. §1.132, dated Jan. 21, 2009.
Declaration of Witold Filipowicz, M.D., Ph.D., Under 35 U.S.C. §1.132, dated Jan. 12, 2009.
Definitions of "in vitro" and "in vivo" from "Compact Oxford English Dictionary" (printed Jan. 28, 2008).
Dernburg et al., "Transgene-mediated cosuppression in the *C. elegans* germ line", Genes & Dev., 2000, vol. 14, pp. 1578-1583.
Dunn, "Ribonuclease III", The Enzymes, 1982, Chapt. 15, vol. 15, pp. 485-499.

(56) References Cited

OTHER PUBLICATIONS

Dykxhoorn et al. "Killing the Messenger: Short RNAs that Silence Gene Expression". Nature Reviews Molecular Cell Biology, vol. 4, (2003) p. 457-467.
Elmen et al., "Locked nucleic acids (LNA) mediated improvements in siRNA stability and functionality", Nucleic Acids Research, 2005, vol. 33, No. 1, pp. 439-447.
English translation of International Preliminary Examination Report for PCT/DE2000/00244 dated May 9, 2001.
English Translation of Written Reply to the Written Demand for Invalidation Trial against Japanese Patent No. 4095895 dated Dec. 22, 2011.
European Patent Application No. 126325.0, filed Dec. 1, 2000.
European Search Report issued Jul. 22, 2011 in EP 10184660.8.
Extended European Search Report dated Jul. 22, 2011 for application No. 10184520.4.
Extended European Search Report dated May 26, 2011 for Application No. 10179947.6.
Extended European Search Report dated May 27, 2011 for Application No. 10179952.6.
Extended European Search Report dated May 27, 2011 for Application No. 10180025.8.
Extended European Search Report dated May 27, 2011 for application No. 10184711.9.
Fire, "Gene Silencing by Double Stranded RNA," Nobel Lecture, Dec. 8, 2006.
Fraser et al., "Functional genomic analysis of *C. elegans* chromosome I by systematic RNA interference", Nature, 2000, vol. 408, pp. 325-330.
Further arguments submitted by BASF SE (Opponent 4) in opposition to EP1407044, dated Sep. 10, 2009.
Further arguments submitted by BASF SE (Opponent 4) in Opposition to EP1407044, dated Sep. 30, 2010.
Further arguments submitted by patentee in EP1407044, dated Oct. 1, 2010.
Further arguments submitted by Sarah E. Rogues (Opponent 3) in opposition to EP1407044, dated Oct. 1, 2010.
Further arguments submitted by Silence Therapeutics (Opponent 5) in opposition to EP1407044, dated Oct. 1, 2010.
Abu_Shakra et al., "Cancer and autoimmunity: autoimmune and rheumatic features in patients with malignancies", Annals of the Rheumatic Diseases, 2001, vol. 60, pp. 433-440.
Allerson et al., "Fully 2'-modified oligonucleotide duplexes with improved in vitro potency and stability compared to unmodified small interfering RNA", J. Med. Chem., 2005, vol. 48, pp. 901-904.
Appeal brief submitted by BASF SE (Opponent 4) in opposition to EP1407044, dated Jun. 15, 2011.
Appeal brief submitted by Pfizer (Opponent 2) in opposition to EP1407044, dated Jun. 24, 2011.
Appeal brief submitted by Sarah E. Rogues (Opponent 3) in opposition to EP1407044, dated Jun. 23, 2011.
Appeal brief submitted by Silence Therapeutics (Opponent 5) in opposition by EP1407044, dated Jun. 27, 2011.
Appeal brief submitted by Sirna Therapeutics (Opponent 1) in opposition to EP1407044, dated Jun. 20, 2011.
Applicant's EPO Letter Cited in Opposition to EP 1309726 dated Oct. 28, 2008.
Applicant's EPO letter cited in opposition to EP1309726, dated Aug. 24, 2006.
Auxiliary request for dismissal of appeals in the opposition proceeding against European Patent No. 1 407 044 (Application No. 01 985 833.1), submitted by patentee, dated Nov. 10, 2011, 12 pages.
Barawkar D. A. and T. C. Bruice: "Synthesis, biophysical properties, and nuclease resistance properties of mixed backbone oligonucleotides containing cationic internucleoside guanidinium linkages: Desoxynucleic guanidine/DNA chimeras", Proc. Natl. Acad. Sci. Chemistry, Biochemistry, USA, Sep. 1998, vol. 95, pp. 11047-11052.
Barber G. N. et al.: "Mutants of the RNA-Dependent Protein Kinase (PKR) Lacking Double-Stranded RNA Binding Domain I Can Act as Transdominant Inhibitors and Induce Malignant Transformation", Mol. and Cell. Biol., vol. 15, No. 6, pp. 3138-3146, Jun. 1995.
Bardwell et al., "Autoregulation of RNase III operon by mRNA processing," The EMBO Journal, vol. 8, pp. 3401-3407 (1989).
Barlow et al., "Interferon synthesis in the early post-implantation mouse embryo," Differentiation, vol. 27, pp. 229-235, 1984.
Bhan, P. et al.: "2',5'-linked oligo-3'-desoxyribonucleoside phosphorothioate chimeras: thermal stability and antisense inhibition of gene expression", Nucleic Acid Research, vol. 25, 1997, pp. 3310-3317.
Braasch et al., "RNA interference in mammalian cells by chemically-modified RNA", Biochemistry, 2003, vol. 42, pp. 7967-7975.
Braich, R. S. And M. 1. Damha: "Regiospecific Solid-Phase Synthesis of Branched Oligonucleotides. Effect of Vicinal 2',5'- (or 2',3'-) and 3',5'-Phosphodiester Linkages on the Formation of Hairpin DNA", Bioconjugate Chem.; May-Jun. 1997; vol. 8, No. 3, pp. 370-377.
Brennicke, A. et al.: "RNA editing", FEMS Microbiology Reviews 23, pp. 297-316 (1999).
Bridge et al., "Induction of an inteferon response by RNAi vectors in mammalian cells", Nature Genetics, 2003, vol. 34, No. 3, pp. 263-264.
Bumcrot et al., "RNAi therapeutics: a potential new class of pharmaceutical drugs," Nature Chemical Biology, vol. 2, No. 12: 711-719 (2006).
Burke et al., "Appearance of Interferon Inducibility and Sensitivity during Differentiation of Murine Teratocarcinoma Cells in Vitro," Cell, vol. 13, pp. 243-248, 1978.
Byrom et al., "Inducing RNAi with siRNA cocktails generated by RNase III", TechNotes, vol. 10, pp. 1, Ambion (2004).
Caplen, "RNAi as a gene therapy approach", Expert Opin. Biol. Ther., 2003, vol. 3, No. 4, pp. 575-586.
Case 1:09-cv-11116-PBS Document 500-20. Exhibit 20 Filed Oct. 18, 2010, 5 pages.
Case 1:11-cv-10484-PBS *The University of Utah v. Max-Planck-Gesellschaft zur Forderung der Wissenschaften E.V.*—Document 1—Plaintiff's complaint filed Mar. 22, 2011.
Case1:11-cv-10484-PBS—Document 1-1—Exhibit 1 associated with plaintiff's complaint, filed Mar. 22, 2011.
Case1:11-cv-10484-PBS—Document 1-10—Exhibit 10 associated with plaintiff's complaint, filed Mar. 22, 2011.
Case1:11-cv-10484-PBS—Document 1-11—Exhibit 11 associated with plaintiff's complaint, filed Mar. 22, 2011.
Case1:11-cv-10484-PBS—Document 1-12—Exhibit 12 associated with plaintiff's complaint, filed Mar. 22, 2011.
Case1:11-cv-10484-PBS—Document 1-13—Exhibit 13 associated with plaintiff's complaint, filed Mar. 22, 2011.
Case1:11-cv-10484-PBS—Document 1-14—Exhibit 14 associated with plaintiff's complaint, filed Mar. 22, 2011.
Case1:11-cv-10484-PBS—Document 1-15—Exhibit 15 associated with plaintiff's complaint, filed Mar. 22, 2011.
Case1:11-cv-10484-PBS—Document 1-16—Exhibit 16 associated with plaintiff's complaint, filed Mar. 22, 2011.
Case1:11-cv-10484-PBS—Document 1-17—Exhibit 17 associated with plaintiff's complaint, filed Mar. 22, 2011.
Case1:11-cv-10484-PBS—Document 1-18—Exhibit 18 associated with plaintiff's complaint, filed Mar. 22, 2011.
Case1:11-cv-10484-PBS—Document 1-19—Exhibit 19 associated with plaintiff's complaint, filed Mar. 22, 2011.
Case1:11-cv-10484-PBS—Document 1-2—Exhibit 2 associated with plaintiff's complaint, filed Mar. 22, 2011.
Case1:11-cv-10484-PBS—Document 1-20—Exhibit 20 associated with plaintiff's complaint, filed Mar. 22, 2011.
Case1:11-cv-10484-PBS—Document 1-21—Exhibit 21 associated with plaintiff's complaint, filed Mar. 22, 2011.
Case1:11-cv-10484-PBS—Document 1-22—Exhibit 22 associated with plaintiff's complaint, filed Mar. 22, 2011.
Case1:11-cv-10484-PBS—Document 1-23—Exhibit 23 associated with plaintiff's complaint, filed Mar. 22, 2011.
Case1:11-cv-10484-PBS—Document 1-24—Exhibit 24 associated with plaintiff's complaint, filed Mar. 22, 2011.
Case1:11-cv-10484-PBS—Document 1-25—Exhibit 25 associated with plaintiff's complaint, filed Mar. 22, 2011.

(56) References Cited

OTHER PUBLICATIONS

Case1:11-cv-10484-PBS—Document 1-26—Exhibit 26 associated with plaintiff's complaint, filed Mar. 22, 2011.
Case1:11-cv-10484-PBS—Document 1-27—Exhibit 27 associated with plaintiff's complaint, filed Mar. 22, 2011.
Case1:11-cv-10484-PBS—Document 1-28—Exhibit 28 associated with plaintiff's complaint, filed Mar. 22, 2011.
Case1:11-cv-10484-PBS—Document 1-29—Exhibit 29 associated with plaintiff's complaint, filed Mar. 22, 2011.
Case1:11-cv-10484-PBS—Document 1-3—Exhibit 3 associated with plaintiff's complaint, filed Mar. 22, 2011.
Case1:11-cv-10484-PBS—Document 1-30—Exhibit 30 associated with plaintiff's complaint, filed Mar. 22, 2011.
Case1:11-cv-10484-PBS—Document 1-31—Exhibit 31 associated with plaintiff's complaint, filed Mar. 22, 2011.
Case 1:11-cv-10484-PBS. Document 67. Surreply in Opposition to the Official Capacity Defendants' Motion to Dismiss University of Utah's Second Amended Complaint. Filed May 9, 2012.
Case 1:11-cv-10484-PBS. Document 68. Notice of Voluntary Dismissal of Counts VI (Conversion) and VII (Replevin) and Request to Strike Certain Matter from Paragaphs G and H of Prayer for Relief (Assignment) of the Second Amended Complaint. Filed May 21, 2012.
Case 1:11-cv-10484-PBS. Document 69. Defendant's Response to Plaintiff's Notice of Voluntary Dismissal of Counts VI (Conversion) and VII (Replevin) and Request to Strike Certain Matter from Paragraphs G and H of Prayer for Relief (Assignment) of the Second Amended Complaint. Filed May 25, 2012.
Case 1:11-cv-10484-PBS. Document 70. Memorandum and Order Denying Motions to Dismiss. Filed Jun. 11, 2012.
Dykxhoorn, D.M. and Lieberman, J., "The Silent Revolution: RNA Interference as Basic Biology, Research Tool, and Therapeutic," Annu. Rev. Med., 56:401-423 (2005).
Zhou, M-Yi, et al., "In Vivo Expression of Neutorphil Inhibitory Factor via Gene Transfer Prevents Lipopolysaccaride-Induced Lung Neutrophil Infiltration and Injury by a Beta2 Integrin-Dependent Mechanism," J. Clin. Invest., 101 (11):2427-2437 (1998).
Nogawa, M., et al., "Intravesical Administration of Small Interfering RNA Targeting PLK-1 Successfully Prevents the Growth of Bladder Cancer," The Journal of Clinical Investigation, 115(4):978 (2005).
Sato, A., et al., "Small Interfering RNA Delivery to the Liver by Intravenous Administration of Galactosylated Cationic Liposomes in Mice," Biomaterials, 28:1434-1442 (2007).
U.S. Appl. No. 60/279,661, filed Mar. 30, 2001.
U.S. Appl. No. 09/889,802, filed Sep. 17, 2001.
U.S. Appl. No. 60/117,635, filed Jan. 28, 1999.
Appeal Brief submitted by Sanofi-Aventis dated Aug. 9, 2012 against the Interlocutory Decision dated Mar. 30, 2012 in the opposition proceedings in EP 1309726.
Appeal Brief submitted by Silence Therapeutics dated Aug. 9, 2012 against the Interlocutory Decision dated Mar. 30, 2012 in the opposition proceedings in EP 1309726.
Kennerdell and Carthew, "Heritable gene silencing in *Drosophila* using double-stranded RNA," 2000, Nature Biotechnology, 17:896-898.
Ketting et al., Dicer functions in RNA interference and in synthesis of small RNA involved in developmental timing in *C. elegans*. Genes Dev. Oct. 15, 2001;15(20):2654-9.
Khvorova, Anastasia et al., "Functional siRNAs and miRNAs Exhibit Strand Bias," Cell, vol. 115:209-216 (2003).
Kidner et al., Macro effects of microRNAs in plants. Trends Genet. Jan. 2003;19(1):13-6.
Klahre, Ulrich et al., "High molecular weight RNAs and small interfering RNAs induce systemic posttranscriptional gene silencing in plants," PNAS, vol. 99(18):11981-11986 (2002).
Knight, Scott W. et al., "A Role for the RNase III Enzyme DCR-1 in RNA Interference and Germ Line Development in *Caenorhabditis elegans*," Science, vol. 293:2269-2271 (2001).
Lai, microRNAs: runts of the genome assert themselves. Curr Biol. Dec. 2, 2003;13(23):R925-36. Review.

Lau et al., An abundant class of tiny RNAs with probable regulatory roles in *Caenorhabditis elegans*. Science. Oct. 26, 2001;294(5543):858-62.
Lee et al., "The *C. elegans* Heterochroic Gene lin-4 encodes Small RNAs with Antisense Complementariity to lin-14," Cell 75:843-854 (1993).
Lee, Rosalind C. et al, "An Extensive Class of Small RNAs in *Caenorhabditis elegans*," Science, vol. 294:862-864 (2001).
Lewis, David L. et al., "Efficient delivery of siRNA for inhibition of gene expression in postnatal mice," Nature Genetics, vol. 32:107-108 (2002).
Li, Bao-jian et al., "Using siRNA in pophylactic and therapeutic regimens against SARS coronavirus in Rhesus macaque," Nature Medicine, vol. 11(9):944-951 (2005).
Lima et al., Cleavage of single strand RNA adjacent to RNA-DNA duplex regions by *Escherichia coli* RNase HI. J Biol Chem. Oct. 31, 1997;272(44):27513-6.
Lima, Walt F. et al., "Human RNase HI Uses NOe Tryptophan and Two Lysines to Position the Enzyme at the 3'-DNA/5' RNA Terminus of the Heteroduplex Substrate," The Journal of Biological Chemistry, vol. 278(50):49860-49867 (2003).
Lingor et al., Targeting neurological disease with RNAi. Mol Biosyst. Nov. 2007;3(11):773-80. Epub Aug. 29, 2007. Review.
Lipardi et al., RNAi as random degradative PCR: siRNA primers convert mRNA into dsRNAs that are degraded to generate new siRNAs. Cell. Nov. 2, 2001;107(3):297-307.
Lutz et al., Differential discrimination of DNA polymerase for variants of the non-standard nucleobase pair between xanthosine and 2,4-diaminopyrimidine, two components of an expanded genetic alphabet. Nucleic Acids Res. Apr. 1, 1996;24(7):1308-13.
Ma et al., Structural basis for 5'-end-specific recognition of guide RNA by the *A. fulgidus* Piwi protein. Nature. Mar. 31, 2005;434(7033):666-70.
Maine et al., A conserved mechanism for post-transcriptional gene silencing. Genome Biology. 2000;1 (3):1018.1-1018.4.
Majlessi, Mahrdad et al., "Advantages of 2'-0-methyl oligoribonucleotide probes for detecting RNA targets," Nucleic Acids Research, vol. 26(9):2224-2229 (1998).
Mallory et al., MicroRNAs: something important between the genes. Curr Opin Plant Biol. Apr. 2004;7(2):120-5.
Manche et al., "Interactions between Double-Stranded RNA Regulators and the Protein Kinase DAI" (1992) Molecular and Cellular Biology 12(11):5238-5248.
Marcus et al., Defective interfering particles with covalently linked [+/] RNA induce interferon. Nature. Apr. 28, 1977;266(5605):815-9.
Martinez, Javier et al, "Single-Stranded Antisense siRNAs Guide Target RNA Cleavage in RNAi," Cell, vol. 110:563-574 (2002).
Martinez, Luis Alfonso et al., "Synthetic small inhibiting RNAs: Efficient tools to inactivate oncogenic mutations and restore p53 pathways," PNAS, vol. 99(23):14849-14854 (2002).
Mathews et al., Adenovirus virus-associated RNA and translation control. J Virol. 1991;6(11):5657-62.
Matzke et al., RNA-based silencing strategies in plants. Curr Opin Genet Dev. Apr. 2001;11(2):221-7.
Matzke et al., RNAi extends its reach. Science. Aug. 22, 2003;301(5636):1060-1.
Matzke et al., RNAi-mediated pathways in the nucleus. Nat Rev Genet. Jan. 2005;6(1):24-35.
McManus, Michael T. et al., "Small Interfering RNA-Mediated Gene Silencing in T Lymphocytes," The Journal of Immunology, vol. 169:5754-5760 (2002).
Mello et al., Revealing the world of RNA interference. Nature. Sep. 16, 2004;431(7006):338-42.
Miyagishi, Makoto et al., "U6 promoter-drive siRNAs with four uridine 3' overhangs efficiently suppress targeted gene expression in mammalian cells," Nature Biotechnology, vol. 19:497-500 (2002).
Molenaar, C. et al., "Linear 2'0-Methyl RNA probes for the visualization of RNA in living cells," Nucleic Acids Research, vol. 29(17):1-9 (2001).
Monia et al., Evaluation of 2'-modified oligonucleotides containing 2'-deoxy gaps as antisense inhibitors of gene expression. J Biol Chem. Jul. 5, 1993;268(19):14514-22.

(56) References Cited

OTHER PUBLICATIONS

Monia et al., Selective inhibition of mutant Ha-ras mRNA expression by antisense oligonucleotides. J Biol Chem. Oct. 5, 1992;267(28):19954-62.

Monia et al., Sequence-specific antitumor activity of a phosphorothioate oligodeoxyribonucleotide targeted to human C-raf kinase supports an antisense mechanism of action in vivo. Proc Natl Acad Sci U S A. Dec. 24, 1996;93 (26):15481-4.

Monia, Brett P. et al., "Sequence-specific antitumor activity of a phosphorothioate oligodeoxyribonucleotide targeted to human C-raf kinase supports an antisense mechanism of action in vivo," Proc. Natl. Acad. Sci. USA, vol. 93:15481-15484 (1996).

Morita et al., "Antisense oligonucleotides targeting c-fos mRNA inhibit rheumatoid synovial fibroblast proliferation," 1998, Ann Rheum Dis, vol. 57, pp. 122-124.

Moss et al., MicroRNAs: something new under the sun. Current Biology. 2002;12:R688-90.

Mourelatos, Zissimos et al., "miRNPs: a novel class of ribmucleoproteins containing numerous microRNAs," Genes & Development, vol. 16:720-728 (2002).

Myers, Jason W. et al., "Recombinant Dicer efficiently converts large dsRNAs into siRNAs suitable for gene silencing," Nature Biotechnology, vol. 21:324-328 (2003).

Nguyen et al., RNAi therapeutics: an update on delivery. Curr Opin Mol Ther. Apr. 2008;10(2):158-67. Review.

Nishikura, Kazuko, "A Short Primer on RNAi: RNA-Directed RNA Polymerase Acts as a Key Catalyst," Cell, Vd. 107:415 418 (2001).

Nishina et al., Efficient in vivo delivery of siRNA to the liver by conjugation of alpha-tocopherol. Mol Ther. Apr. 2008;16(4):734-40. Epub Feb. 12, 2008.

Novina et al., The RNAi revolution. Nature. Jul. 8, 2004;430(6996):161-4.

Nykanen et al., ATP requirements and small interfering RNA structure in the RNA interference pathway. Cell. Nov. 2, 2001;107(3):309-21.

Paddison, Patrick J. et al., "Stable suppression of gene expression by RNAi inmammalian cells," PNAS:. vol. 99 (3):1443-1448 (2002).

Park et al., Double-stranded siRNA targeted to the huntingtin gene does not induce DNA methylation, 2004, Biochemical and Biophysical Research Communications, vol. 323, pp. 275-280.

Parker et al., Structural insights into mRNA recognition from a PIWI domain-siRNA guide complex. Nature. Mar. 31, 2005;434(7033):663-6.

Pellino et al., "ATP modulates siRNA interactions with an endogenous human Dicer comples" RNA 2005 11:1719-1724 (2005).

Persengiev, Stephen P. et al., "Nonspecific, concentration-dependent stimulation and repression of mammalian gene expression by small interfering RNAs (siRNAs)," RNA, vol. 10:12-18 (2004).

Pfeffer et al., "RNA silencing," B.I.F. Fugura, 2005, vol. 20, pp. 83-91.

Pillai et al., "Repression of protein synthesis by miRNAs: how many mechanisms?" Trends in Cell Biology 17 (3):118-126.

Reich, Samuel J. et al., "Small interfering RNA (siRNA) targeting VEGF effectively inhibits ocular neovascularization in a mouse model," Molecular Vision, vol. 9:210-216 (2003).

Roshak, A.K. et al 1996, "Manipulation of Distinct NFKB Proteins Alters Interleukin-113-induced Human Rheumatoid Synovial Fibroblast Prostaglandin E2 Formation," J Biological Chemistry, 271:49; 31496-31501.

Rossi et al., RNAi and the P-body connection. Nat Cell Biol. Jul. 2005;7(7):643-4.

Ruvkun, Gary, "Glimpses of a Tiny RNA World," Science, vol. 294:797-799 (2001).

Schmidt, Negotiating the RNAi patent thicket. Nat Biotechnol. Mar. 2007;25(3):273-5. Epub Mar. 1, 2007.

Schmitter et al., "Effects of Dicer and Argonaute down-regulation on mRNA levels in human HEK293 Cells", Nucleic Acids Research, 34(17):4801-4815 (2006).

Schmitz, John C. et al., "Effect of 2'-0-methyl antisense ORNs on expression of thymidylate synthase in human colon cancer RKO cells," Nucleic Acids Research, vol. 29(2):415-422 (2001).

Schramke et al., Those interfering little RNAs! Silencing and eliminating chromatin. Curr Opin Genet Dev. Apr. 2004;14(2):174-80.

Schwartz et al., Why do miRNAs live in the miRNP? Genes Dev. May 1, 2002;16(9):1025-31.

Schwarz, Dianne S. et al, "Evidence that siRNAs Function as Guides, Not Primers, in the *Drosophila* and Human RNAi Pathways," Molecular Cell, vol. 10:537-548 (2002).

Schwarz, Dianne S. et al., "Asymmetry in the Assembly of the RNAi Enzyme Complex," Cell, Vd. 115:199-208 (2003).

Shi, Yang, "Mammalian RNAi for the masses," Trends in Genetics, vol. 19(1):9-12 (2003).

Silencer TM Express Kit Instruction Manual, Version 0305, Ambion, Inc., May 2003.

Simeoni et al. also in RNA Silencing, Methods and Protocols, (Humana Press, 2005).

Siomi et al., RNA interference: a new mechanism by which FMRP acts in the normal brain? What can *Drosophila* teach us? Ment Retard Dev Disabil Res Rev. 2004;10(1):68-74.

Sioud et al., Therapeutic siRNAs. Trends Pharmacol Sci. Jan. 2004;25(1):22-8.

Sioud in RNA Silencing, Methods and Protocols, (Humana Press, 2005).

Skipper et al., Elegant tour de force. Nature Reviews Genetics. 2003;4:79-80.

Skipper et al., Have our dreams been shattered? Nature Reviews Genetics. 2003;4:671.

Skyba, Danny M. et al., "Direct In Vivo Visualization of Intravascular Destruction of Microbubbles by Ultrasound and its Local Effects on Tissue," Circulation, vol. 98:290-293 (1998).

Smyth et al., Gene silencing: cosuppression at a distance. Curr Biol. Dec. 1, 1997;7(12):R793-5.

Song, Erwei et al., "RNA interference targeting Fas protects mice from fulminant hepatitis," Nature Medicine, vol. 9 (3):347 351 (2003).

Sontheimer et al., Assembly and function of RNA silencing complexes. Nat Rev Mol Cell Biol. Feb. 2005;6 (2):127-38.

Soutschek, Jurgen et al., "Therapeutic silencing of an endogenous gene by systemic administration of modified siRNAs," Nature, vol. 432:173-178 (2004).

Stark et al., "How Cells Respond to Interferons", Annu. Rev. Biochem. 1998, 67:227-264.

Stipp, David, "Biotech's Billion Dollar Breakthrough," Fortune, vol. 147(10):96-100 (2003).

Stratagene pBluescript II Phagemid Vectors Instruction Manual for Catalog # 212207, downloaded from the Stratagene, Inc. website on Jan. 11, 2007.

Svoboda, et al., "Lack of homologous sequence-specific DNA methylation in response to stable dsRNA expression in mouse oocytes," Nucleic Acid Research vol. 32(12):3601-3606 (2004).

Szweykowska-Kulihska, Zofiia et al., "RNA interference and its role in the regulation ofeucaryotic gene expression," Acta Biochimica Polonica, vol. 50(1):217-229 (2003).

Tabara, Hiroaki et al., "The dsRNA Binding Protein RDE-4 Interacts with RDe-1, DCR-1, and a DExH-Box Helicase to Direct RNAi in *C. elegans*," Cell, vol. 109:861-871 (2002).

Tahbaz et al., "Characterization of the interactions between mammalian PAZ PIWI domain proteins and Dicer" EMBO Reports, 5(2):189-194 (2004).

Takeshita et al., Increased gene expression after liposome-mediated arterial gene transfer associated with intimal smooth muscle cell proliferation. In vitro and in vivo fmdings in a rabbit model of vascular injury. J Clin Invest. Feb. 1994;93(2):652-61.

Tan, P. H. et al., "Gene knockdown with intrathecal siRNA of NMDA receptor NR2B subunit reduces formalin-induced nociception in the aat," Gene Therapy, vol. 12:59-66 (2005).

Tang, Guiliang et al., "A biochemical framework for RNA silencing in plants," Genes & Development, vol. 17:49-63 (2003).

(56) References Cited

OTHER PUBLICATIONS

Thakker, Deepak R. et al., "Neurochemical and behavioral consequences of widespred gene knockdown in the adult mouse brain by using nonviral interference," PNAS, vol. 101(49):17270-17275 (2004).
Tijsterman et al., The genetics of RNA silencing. Annu Rev Genet. 2002;36:489-519.
Tijsterman, Marcel et al, "RNA Helicase MUT-14-Dependent Gene Silencing Triggered in *C. elegans* by Short Antisense RNAs," Science, vol. 295:694-697 (2002).
Tijsterman, Marcel et al., "PPW-1, a PAZ/PIWI Protein Required for Efficient Germline RNAi, is Defective in a Natural Isolate of *C. elegans*," CurrentBiology, vol. 12:1535-1540 (2002).
Tracewell, et al., In Vivo Modulation of the Rat Cytochrome P450 1A1 by Double-Stranded Phosphorothioate Oligodeoxynucleotides, 1995, Toxicology and Applied Pharmacology, 135:179-184.
Tuschl et al., Functional genomics: RNA sets the standard. Nature. Jan. 16, 2003;421(6920):220-1.
Tuschl et al., RNA silencing: products and perspectives advancing cell discovery. Upstate Biosignals. 3:1-15, Dec. 2004.
Tuschl, "Small Interfering RNAs: A Revolutionary Tool for the Analysis of Gene Function and Gene Therapy," Molecular Interventions, 2002, vol. 2, No. 3, pp. 158-167.
Tuschl, Thomas, "Expanding small RNA interference," Nature Biotechnology, vol. 20:446-448 (2002).
Vaucheret et al., Transgene-induced gene silencing in plants. Plant J. Dec. 1998;16(6):651-9.
Vickers, Timothy A. et al., "Efficient Reduction of Target RNAs by Small Interfering RNA and RNase H-dependent Antisense Agents," The Journal of Biological Chemistry, vol. 278(9):7108-7118 (2003).
Wall, Nathan R. et al., "Small RNA: can RNA interference be exploited for therapy?" TheLancet, vol. 362:1401-1403 (2003).
Wang et al., Replicating satellite RNA induces sequence-specific DNA methylation and truncated transcripts in plants. RNA. Jan. 2001;7(1):16-28.
Wang et al., "Inhibition of *Trypanosoma brucei* Gene Expression by RNA Interference Using an Integratable Vector with Opposing T7 Promoters", The Journal of Biological Chemistry, 275(51):40174-40179 (2000).
Waterhouse et al., Exploring plant genomes by RNA-induced gene silencing. Nature Reviews Genetics. 2002;4:29-38.
Weitzer et al., The human RNA kinase hClp1 is active on 3' transfer RNA exons and short interfering RNAs. Nature. May 10, 2007;447(7141):222-6.
Wess, Ludger et al., "Managing Complexity: Early Days for RNAi," Compugen, retrieved online athttp://www.cgen.com/news.articles/article031703.html (2003).
Whalen et al., DNA-mediated immunization to the hepatitis B surface antigen. DNA Vaccines: A new era in vaccinology. 1995:64-76.
Woo et al., G/C-modified oligodeoxynucleotides with selective complementarity: synthesis and hybridization properties. Nucleic Acids Res. Jul. 1, 1996;24(13):2470-5.
Wu et al., Human RNase III is a 160-kDa protein involved in preribosomal RNA processing. J Biol Chem. Nov. 24, 2000;275(47):36957-65.
Wu et al., Properties of cloned and expressed human RNase HI. J Biol Chem. Oct. 1, 1999;274(40):28270-8.
Xia, Haibin et al., "siRNA-mediated gene silencing in vitro and in vivo," Nature Biotechnology, vol. 20:1006-1010 (2002).
Yang, Dun et al., "Short RNA duplexes produced by hydrolysis with *Escherichia coli* RNase III mediate effective RNA interference in mammalian cells," PNAS, vol. 99(15):9942-9947 (2002).
Zamore et al., Ribo-gnome: the big world of small RNAs. Science. Sep. 2, 2005;309(5740):1519 24.
Zamore et al., RNA interference: listening to the sound of silence. Nat Struct Biol. Sep. 2001;8(9):746-50.
Zamore, Phillip D. et al., "siRNAs knock down hepatitis," Nature Medicine, vol. 9(3):266-267 (2003).
Zamore et al., "Target dependent accumulation of small RNAs during RNAi in *C. elegans*", International *C. elegans* Meeting 2001, 307.
Zeng, Yan et al., "Both Natural and Designed Micro RNAs Can Inhibit the Expression of Cognate mRNAs When Expressed in Human Cells," Molecular Cell, vol. 9:1327-1333 (2002).
Zhang, Haidi et al., "Human Dicer preferentially cleaves dsRNAs at their termini without a requirement for ATP," The EMBO Journal, vol. 21(21):5875-5885 (2002).
Zhang, Yingjie et al., "Engineering Mucosal RNA Interference in Vivo," Molecular Therapy, Vd. 14(3):336-342 (2006).
Zimmermann, Tracy S. et al., "RNAi-mediated gene silencing in non-human primates," Nature, vol. 441:111-114 (2006).
Plaintiffs' Complaint. Civil Action No. Sep. 2654. *Max-Planck-Gesellschaft zur Forderung der Wissenschaften e.V.* v. *Wolf Greenfield & Sacks, PC*. Dated Jun. 26, 2009.
Plaintiffs' Ex Parte Motion for a Short Order of Notice. Civil Action No. 09-2674-BLS. *Max Planck-Gesellschaft zur Forderung der Wissenschaften e.V.* v. *Whitehead Institute for Biomedical Research*, et al. Dated Jun. 30, 2009.
Plaintiffs' Motion for Preliminary Injunction. Civil Action No. 09-2674-BLS. *Max-Planck Gesellschaft zur Forderung der Wissenschaften e.V.* v. *Whitehead Institute for Biomedical Research, et al*. Dated Jun. 30, 2009.
Plantiffs' Ex Parte Motion for Temporary Restraining Order. Civil Action No. 09-2674-BLS. *Max Planck-Gesellschaft zur Forderung der Wissenschaften e.V.* v. *Whitehead Institute for Biomedical Research, et al*. Dated Jun. 30, 2009.
Proceedings: 1:09-cv-11116-PBS, *Max-Planck-Gesellschaft zur Forderung der Wissenschaften e.V.* v. *Whitehead Institute for Biomedical Research, et al.* Transcript. Jul. 1, 2009.
Agrawal, Neema et al., "RNA Interference: Biology, Mechanism, and Applications," Microbiology and Molecular Biology Reviews, vol. 67(4):657-685 (2003).
Agy Therapeutics announces study demonstrating utility of RNA interference in mammalian cells for CNS drug discovery. Press release, Nov. 2001.
Alexeev et al., Localized in vivo genotypic and phenotypic correction of the albino mutation in skin by RNA-DNA oligonucleotide. Nat Biotechnol. Jan. 2000;18(1):43-7.
Alfonzo et al., The mechanism of U insertion/deletion RNA editing in kinetoplastid mitochondria, 1997, Nucleic Acids Research, vol. 25, No. 19, pgs. 3751-3759.
Ali et al., Who discovered (or invented 'The art' of double-stranded) RNA interference? Letter of Ali. May 6, 2005.
Ali, Commentary regarding Who discovered (or invented 'the art' of double-stranded) RNA interference? Dated Aug. 2005. 7 pages. (www.rnaiconception.com).
Ambros, V., "microRNAs: Tiny Regulators with Great Potential," Cell, vol. 107:823-826 (2001).
Ambros, V., "The evolution of our thinking about microRNAs", Nature Medicine, vol. 14, No. 10, Oct. 2008, pp. 1036-1040.
Aoki et al., "Inhibition of the p53 Tumor Suppressor Gene Results in Growth of Human Aortic Vascular Smooth Muscle Cells," 1999, Hypertension, vol. 34, No. 2, pp. 192-200.
Baev et al., "Stress-Induced Membrane Association of the *Streptococcus mutans* GTP-Binding Protein, an Essential G Protein, and Investigation of Its Physiological Role by Utilizing an Antisense RNA Strategy," 1999, Infection and Immunity, vol. 67, pp. 4510-4516.
Bartel et al., Micromanagers of gene expression: the potentially widespread influence of matazoan microRNAs. 2004; 5:369-400.
Bartel et al., MicroRNAs: genomics, biogenesis, mechanism, and function. Cell. Jan. 23, 2004;116(2):281-97.
Basic Local Alignment Search Tool (BLAST) analysis, available through NCBI, of nucleic acid sequence "cccggtacccagcttttgttccc" completed on Jan. 11, 2007.
Bass, Brenda L., "The short answer," Nature, vol. 411:428-429 (2001).
Baulcombe et al., Gene silencing: RNA makes RNA makes no protein. Curr Biol. Aug. 26, 1999;9(16):R599-601.
Bellon et al., 4'-Thio-oligo-beta-D-ribonucleotides: synthesis of beta-4'-thio-oligouridylates, nuclease resistance, base pairing properties, and interaction with HIV-1 reverse transcriptase. Nucleic Acids Res. Apr. 11, 1993;21 (7):1587-93.

(56) References Cited

OTHER PUBLICATIONS

Bernstein, Emily et al., "The rest is silence," RNA, vol. 7:1509-1521 (2001).
Bevilacqua et al. (1996) Biochemist 35:9983-9994.
Biotech Journal, "Small interfering RNAs," retrieved online atwww.biotechjournal.com (2002).
Borst et al., Replication of viral RNA, 8. Studies on the enzymatic mechanism of replication of MS2 RNA. Proc Natl Acad Sci U S A. Sep. 1965;54(3):982-7.
Bosher et al., RNA interference can target pre-mRNA: consequences for gene expression in a Caenorhabditis elegans operon. Genetics. Nov. 1999;153(3):1245-56.
Boutla, Alexandra et al., "Developmental defects by antisense-mediated inactivation of micro-RNAs 2 and 13 in Drosophila and the identification of putative target genes," Nucleic Mils Research, vol. 31(17):4973-4980 (2003).
Boutla, Alexandra et al., "Short 5'-phosphorylated double-stranded RNAs induce RNA interference in Drosophila," Current Biology, vol. 11:1776-1780 (2001).
Brantl, Sabine, "Antisense-RNA regulation and RNA interference," Biochimica et Biophysica Acta, vol. 1575:15-25 (2002).
Brummelkamp et al., New tools for functional mammalian cancer genetics. Nat Rev Cancer. Oct. 2003;3(10):781-9.
Cameron et al., Inhibition of gene expression by a short sense fragment. Nucleic Acids Res. Feb. 11, 1991;19 (3):469-75.
Carrington et al., Role of microRNAs in plant and animal development. Science. Jul. 18, 2003;301(5631):336-8.
Carthew et al., Gene silencing by double-stranded RNA. Curr Opin Cell Biol. Apr. 2001;13(2):244-8.
Celotto, Alicia M. et al., "Exon-specific RNAi: A tool for dissecting the functional relevance of alternative spleing," RNA, vol. 8:718-724 (2002).
Check et al., Gene regulation: RNA to the rescue? Nature. Sep. 4, 2003;425(6953):10-2.
Cheng et al., RNA interference and human disease. Mol Genet Metab. Sep.-Oct. 2003;80(1-2):121-8.
Chi, Jen-Tsan et al., "Genomewide view of gene silencing by small interfering RNAs," PNAS, vol. 100(11):6343-6346 (2003).
Conte, Darryl Jr. et al., "RAN Interference in Caenorhabditis elegans," Current Protocols in Molecular Biology, Unit 26.3, Supplement 62, pp. 26.3.1-26.3.20 (2003).
Couzin et al., Molecular biology. RNAi shows cracks in its armor. Science. Nov. 12, 2004;306(5699):1124-5.
Crooke et al., Kinetic characteristics of Escherichia coli RNase HI: cleavage of various antisense oligonucleotide-RNA duplexes. Biochem J. Dec. 1, 1995;312 ( Pt 2):599-608.
Cullen, Bryan R., "Derivation and function of small interfering RNAs and microRNAs," Virus Research, vol. 102:3-9 (2004).
Cullen, Bryan R., "RNA interference: antiviral defense and genetic tool," Nature Immunology, vol. 3(7):597-599 (2002).
Cullen, "RNAi the natural way," Nature Genetics, 37(11):1163-1165 (2005).
Cummins et al., Characterization of fully 2'-modified oligoribonucleotide hetero- and homoduplex hybridization and nuclease sensitivity. Nucleic Acids Res. Jun. 11, 1995;23(11):2019-24.
De Mesmaeker et al., Backbone modifications in oligonucleotides and peptide nucleic acid systems. Curr Opin Struct Biol. Jun. 1995;5(3):343-55. C.
DePalma, Angelo et al., "Making Sense of RNA Interference Methods," retrieved online http://www.adepalmacom/genomics/0303/Genomics%20and%20Proteomics%20-%20Making%20Sense-%20ofY02ORNA%20Interference%20Methods.htm (2003).
Devroe et al., Therapeutic potential of retroviral RNAi vectors. Expert Opin Biol Ther. Mar. 2004;4(3):319-27.
Doench, John G. et al, "siRNAs can function as miRNAs," Genes & Development, vol. 17:438-442 (2003).

Doi, Noboru et al., "Short-Interfering-RNA-Mediated Gene Silencing in Mammalian Cells Requires Dicer and d1F2C Translation Initiation Factors," Current Biology, vol. 13:41-46 (2003).
Donze, Olivier et al, "RNA interference in mammalian cells using siRNAs synthesized with T7 RNA polymerase," Nucleic Acids Research, vol. 30(10):1-4 (2002).
Dostie, J. et al, "Numerous mcroRNPs in neuronal cells containing novel microRNAs," RNA, vol. 9:180-186 (2003).
Elbashir et al., "Analysis of gene function in somatic mammalian cells using small interfering RNAs," 2002, Methods 26, pp. 199-213.
Essner, Jeffrey J. et al, "Conserved fraction for embryonic nodal cilia," Nature, vol. 418:37-38 (2002).
Etemad-Moghadam et al., Asymmetrically distributed PAR-3 protein contributes to cell polarity and spindle alignment in early C. elegans embryos. Cell. Dec. 1, 1995;83(5):743-52.
Feix et al., Replication of viral RNA. 13. The early product of phage RNA synthesis in vitro. Proc Natl Acad Sci U S A. May 1967;57(5):1401-8.
Filipowicz et al., RNAi: the nuts and bolts of the RISC machine. Cell. Jul. 15, 2005;122(1):17-20.
Filipowicz, "Imprinted expression of small nucleolar RNAs in brain: Time for Rnomics", PNAS, Dec. 19, 2000, 97 (26):14035-14037.
Filipowicz et al., "Post-transcriptional gene silencing by siRNAs and miRNAs", Current Opinion in Structural Biology 15:331-341 (2005).
Filipowicz et al., "Biogenesis of small nucleolar ribonucleoproteins", Current Opinion in Cell Biology 14:319-327 (2002).
Flintoft et al., Virus alert. Nature Reviews Drug Discovery. 2003;2:512.
Freitag et al., Controlling DNA methylation: many roads to one modification. Curr Opin Genet Dev. Apr. 2005;15 (2):191-9.
Garber, Ken, "Prescription RNA," Technology Review, retrieved online at:http://www.technologyreview.com/BioTech/wtr_020,259,pl.html (2002).
Gitlin et al., Nucleic acid-based immune system: the antiviral potential of mammalian RNA silencing. J Virol. Jul. 2003;77(13):7159-65.
Gitlin, Leonid et al., "Short interfering RNA confers intracellular antiviral immunity in human cells," Nature, vol. 418:430 434 (2002).
Gokhale et al., Antisense raf oligodeoxyribonucleotide is protected by liposomal encapsulation and inhibits Raf-1 protein expression in vitro and in vivo: implication for gene therapy of radioresistant cancer. Gene Ther. Dec. 1997;4 (12):1289-99.
Greenwood et al., Ever-decreasing effects. Nature Reviews Cancer. 2003;3:236.
Grishok et al., "Target dependent accumulation of small RNAs during RNAi in C. elegans," retrieved online a http://www.wormbase.org/db/misc/paper?name=° /05Bwm2001p307%5D;class=Paper, (2001).
Grishok A. et al., RNAi (Nematodes:Caenorhabditis elegans) Advances in Genetics, 46:339-360, 2002.
Grzelinski, Marius et al., "RNA Interference-Mediated Gene Silencing of Pleiotrophin Through Polyethylenimine Complexed Small Interfering RNAs In Vivo Exerts Antitumoral Effects in Glioblastoma Xenografts," Human Gene Therapy, vol. 17:751-766 (2006).
Guo, Su et al., "par-1, a Gene Required for Establishing Polarity in C. elegans Embryos, Encodes a Putative Ser/Thr Kinase That is Asymmetrically Distributed," Cell, vol. 81:611-620 (1995).
Haase et al., "TRBP, a regulator of cellular PKR and HIV-1 virus expression, interacts with Dicer and functions in RNA silencing," EMBO Reports, 6(10):961-967 (2005).
Haley, Benjamin et al., "In vitro analysis of RNA interference in Drosophila melanogaster," Methods, vol. 30:330-336 (2003).
Hamada, Makiko et al., "Effects of RNA Interference in Gene Expression (RNAi) inCultured Mammalian Cells of Mismatches and the Introduction of Chemical Modifications at the 3'-Ends of siRNAs," Antisense and Nucleic Acid and Drug Development, vol. 12:301-309 (2002).
Hamilton, Andrew et al., "Two classes of short interfering RNA in RNA silencing," The EMBO Journal, vol. 21(17):4671 4679 (2002).
Hannon, Gregory J., "RNA interference," Nature, vol. 418:244-251 (2002).
Heinrichs et al., Chop, chop. Nature Reviews Molecular Cell Biology. 2003;4:829.

(56) References Cited

OTHER PUBLICATIONS

Heinrichs et al., Down a hairpin. Nature Reviews Molecular Cell Biology. 2003;4:173.
Heinrichs et al., Spreading silence. Nature Reviews Molecular Cell Biology. 2003;4:823.
Hohjoh, Hirohiko, "RNA interference (RNAi) induction with various types of synthetic oligoructeotide duplexes in cultured human cells," FEBS Letters, vol. 521:195-199 (2002).
Holen, Torgeir et al., "Positional effects of short interfering RNAs targeting the human coagulation trigger Tissue Factor," Nucleic Acids Research, vol. 30(8):1757-1766 (2002).
Holen, Torgeir et al., "Similar behaviour of single-strand and double-strand siRNAs suggests they act through a common RNAi pathway," Nucleic Acids Research, vol. 31(9):2401-2407 (2003).
Hope, RNAi surges on: application to cultured mammalian cells. Trends Genet. Aug. 2001;17(8):440.
Hough, Shelley R. et al., "Why RNAi makes sense," Nature Biotechnology, vol. 21(7):731-732 (2003).
Hu-Lieskovan, Siwen et al., "Sequence-Specific Knockdown of EWS-FLI1 by Targeted, Nonviral Delivery of Small Interfering RNA Inhibits Tumor Growth in a Murine Model of Metastatic Ewing's Sarcoma," Cancer Research, vol. 65 (19):8984-8992 (2005).
Hunter et al., Missing Links: miRNAs and plant development. Current Opinion in Genetics & Development. 2002;13:372-8.
Hutvagner et al., RNAi: nature abhors a double-strand. Curr Opin Genet Dev. Apr. 2002; I2(2):225-32.
Jackson, Aimee L. et al., "Expression profiling reveals off-target gene regulation by RNAi," Nature Biotechnology, vol. 21:635-637 (2003).
Jacobs et al., When two strands are better than one: the mediators and modulators of the cellular responses to double-stranded RNA. Virology. May 15, 1996;219(2):339-49. Review.
Staeuber et al., "Bluetongue Virus VP6 Protein Binds ATP and Exhibits an RNA-Dependent ATPase Function and a Helicase Activity that Catalyze the Unwinding of Double-Stranded RNA Substates", Journal of Virology, Oct. 1997, p. 7220-7226.
U.S. Appl. No. 60/130,337, filed Apr. 21, 1999, Pachuk et al.
U.S. Appl. No. 60/279,661, filed Mar. 30, 2001, Tuschl.
The Nobel Prize in Physiology or Medicine 2006, pp. 1-13.
Fire, A., et al., "Potent and Specific Genetic Interference by Double-Stranded RNA in *Caenorhabditis elegans*." Nature 391:806-811 (Feb. 16, 1998).
Tuschl, T., et al., "Targeted mRNA Degradation by Double-Stranded RNA In Vitro," Genes & Development 13:3191-3197 (1999).
Kennerdell, J.R. and Carthew, R.W., "Use of dsRNA-Mediated Genetic Interference to Demonstrate that frizzled and frizzled 2 Act in the Wingless Pathway," Cell 95:1017-1026 (Dec. 23, 1998).
Montgomery, M.K. and Fire, A., "Double-Stranded RNA as a Mediator in Sequence-Specific Genetic Silencing and Co-suppression," TIG 14(7):255-258 (Jul. 1998).
Ngo, H., et al., "Double-Stranded RNA Induces mRNA Degradation in *Trypanosoma brucei*," Proc. Natl. Acad. Sci. USA 95:14687-14692 (Dec. 1998).
Lohmann, J.U., et al., "Silencing of Developmental Genes in Hydra," Developmental Biology 214:211-214 (1999).
Clemens, M.J. and Williams, B.R.G., "Inhibition of Cell-Free Protein Synthesis by pppA2'p5'A2'p5' A: a Novel Oligonucleotide Synthesized by Interferon Treated L Cell Extracts," Cell 13:565-572 (Mar. 1978).
Zhou, A., et al., "Expression Cloning of 2-5A-Dependent RnAase: A Uniquely Regulated Mediator of Interferon Action," Cell 72:753-765 (Mar. 12, 1993).
Zhou, A., et al., "Interferon Action in Triply Deficient Mice Reveals the Existence of Alternative Antiviral Pathways," Virology 258:435-440 (1999).
Wianny, F. and Zernicka-Goetz, M., "Specific Interference with Gene Function by Double-Stranded RNA in Early Mouse Development," Nature Cell Biol. 2:70-75 (Feb. 2000).
Gebauer, F., et al. "Translation Control of Dosage Compensation in *Drosophila* by Sex-lethal: Cooperative Silencing via the 5' and 3' UTRs of msl-2 mRNA is Independent of the Poly(A) Tail," The EMBO Journal 18(21):6146-6154 (1999).
Hamilton, A.J. and Baulcombe, D.C., "A Species of Small Antisense RNA in Posttranscriptional Gene Silencing in Plants," Science 286:950-952 (Oct. 1999).
Wagner, R.W. and Sun, L., "Double-stranded RNA Poses Puzzle," Nature 391:744-745 (Feb. 1998).
Sharp. P.A., "RNAi and Double-strand RNA," Genes & Development 13(2): 139-140 (Jan. 15, 1999).
Bass; B.L., "RNA Editing and Hypermutation by Adenosine Deamination." TIBS 22:157-162 (1997).
Cogoni, C. and Macino, G., "Gene Silencing in Neurospora crassa Requires a Protein Homologous to RNA-Dependent RNA polymerase," Nature 399:166-169 (May 1999).
Grishok, A., et al., "Genetic Requirements for Inheritance of RNAi in *C. elegans*," Science 287:2494-2497 (Mar. 2000).
Ketting, R.F., et al., "mut-7 of *C. elegans*, Required for Transposon Silencing and RNA Interference, is a Homolog of Werner Syndrome Helicase and RNaseD," Cell 99:133-141 (Oct. 1999).
Tabara, H., et al., "The rde-1 Gene, RNA Interference, and Transposon Silencing in *C. elegans*," Cell 99:123-132 (Oct. 1999).
Smardon, A., et al., "EGO-1 is Related to RNA-directed RNA Polymerase and Functions in Germ-line Development and RNA Interference in *C. elegans*," Current Biology 10(4):169-178 (Feb. 2000).
Pal-Bhadra, M., et al., "Cosuppression of Nonhomologous Transfenes in *Drosophila* Involves Mutually Related Endogenous Sequences," Cell 99:35-46 (Oct. 1999).
Fire, A., "RNA-triggered Gene Silencing," Trends in Genetics 15:358-363 (1999).
Sharp, P.A: and Zamore, P.D., "RNA Interference," Science 287:2431-2433 (Mar. 2000).
Sijen, T. and Kooter, J.M., "Post-transcriptional Gene-silencing: RNAs on the Attack or on the Defense," BioEssays 22:520-531 (2000).
Bass, B.L., "Double-Stranded RNA as a Template for Gene Silencing," Cell 101:235-238 (Apr. 2000).
Hammond, S.M., et al., "Post-Transcriptional Gene Silencing by Double-Stranded RNA," Nature Reviews/Genetics 2:110-119 (Feb. 2001).
Hammond, S.M., et al., "An RNA-Directed Nuclease Mediates Post-Transcriptional Gene Silencing in *Drosphila* Cells," Nature 404:293-296 (Mar. 16, 2000).
Zamore, P.D., et al., "RNAi: Double-Stranded RNA Directs the ATP-Dependent Cleavage of mRNA at 21 to 23 Nucleotide Intervals," Cell 101:25-33 (Mar. 31, 2000).
Bernstein, E., et al., "Role for a Bidentate Ribonuclease in the Initiation Step of RNA Interference," Nature 409:363-366 (Jan. 18, 2001).
Elbashir, S.M., et al., "RNA Interference is Mediated by 21- and 22-Nucleotide RNAs," Genes & Development 15:188-200 (2001).
Caplen, n. J., et al., "dsRNA-Mediated Gene Silencing in Cultured Drosophila cells: A Tissue Culture Model for the Analysis of RNA Interference," Gene 252:95-105 (2000).
Kehlenbach, R.H., et al., "Nucleocytoplasmic Shuttling Factors Including Ran and CRM1 Mediate Nuclear Export of NFAT In Vitro," J. Cell Biol. 141(4):863-874 (May 18, 1998).
Kumar, M. and Carmichael, G.G., "Antisense RNA: Function and Fate of Duplex Rna in Cells of Higher Eukaryotes," Microbiol. and Molec. Biol. Reviews 62(4):1415-1434 (Dec. 1998).
Wassebegger, M., "RNA-Directed DNA Methylation," Plant Molec. Biol. 43:203-220 (2000).
Finnegan, E.J., et al., "Gene Silencing: Fleshing out the Bones," Current Biol. 11(3):R99-R102 (2001).
Kass, S.U., et al., "How Does RNA Methylation Repress Transcription?" TIG 13(11):444-449 (Nov. 1997).
Razin, A., "CpG Methylation, Chromatin Structure and Gene Silencing—A Three-Way Connection," EMBO Journal 17 (17):4905-4908 (1998).
Timmons, L. and Fire, A., "Specific Interference by Ingested dsRNA," Nature 395:854 (Oct. 29, 1998).
Cogoni, C. and Macino, G., "Posttranscriptional Gene Silencing in *Neurospora* by a RecQ DNA Helicase," Science 286:2342-2344 (Dec. 17, 1999).

(56) References Cited

OTHER PUBLICATIONS

Grant, S.R., "Dissecting the Mechanisms of Posttranscriptional Gene Silencing: Divide and Conquer," Cell 96:303-306 (Feb. 5, 1999).
Catalanotto, C., et al., "Gene Silencing in Worms and Fungi," Nature 404:245 (Mar. 16, 2000).
Hunter, C.P., "Gene Silencing: Shrinking the Black Box of RNAi," Current Biol. 10(4):R137-R140 (2000).
Hunter, C.P., "Genetics: A Touch of Elegance with RNAi," Current Biol. 9(12):R440-R442 (1999).
Grishok, A., et al., "Genes and Mechanisms Related to RNA Interference Regulate Expression of the Small Temporal RNAs that Control elegans Development Timing," Cell 106:23-34 (Jul. 13, 2001).
Tabara, H., et al., "RNAi in *C. elegans*: Soaking in the Genome Sequence," Science 282:430-431 (Oct. 16, 1998).
Ketting, R.F. and Plasterk, R.H.A., "A Genetic Link Between Co-Suppression and RNA Interference in *C. elegans*," Nature 404:296-298 (Mar. 16, 2000).
Ui-Tei, K., et al., "Sensitive Assay of RNA Interference in Drosophila and Chinese Hamster Cultured Cells Using Firefly Luciferase Gene as Target," FEBS Letters 479:79-82 (2000).
Lam, G. and Thummel, C.S., "Inducible expression of double-stranded RNA directs specific genetic interference in *Drosophila*," Curr. Biol. 10:957-963 (2000).
Williams, B.R.G., et al., "The Respective Roles of the Protein Kinase and pppA2'p5'A2'p5' A-activated Endonuclease in the Inhibition of Protein Synthesis by Double-Stranded RNA in Rabbit Reticulocyte Lysates," Nucleic Acids Research 6 (4):1335-1350 (Apr. 1979).
Braun, et al., "Oligonucleotide and plasmid DNA packaging into polyoma. VPI virus-like particles expressed in *Escherichia coli*," Biotechnol. App. Biochem. 29:31-34 (1999).
Diagram indicating the melting curve of two 23 base pair double stranded molecules submitted by Appellant II in the appeal proceedings against EP 1 144 523 on Feb. 5, 2007 (2 sheets).
Diagram indicating the melting curve of a 19 base pair double stranded molecule submitted by Appellant II in the appeal proceedings against EP 1 144 523 on Feb. 5, 2007.
Gewirtz, et al., "Nucleic Acid Therapeutics: State of the Art and Future Prospects," Blood 92(3):712-736 (Aug. 1, 1998).
Jeffrey, et al., "Nuclear Localization of the Interferon-Inducible Protein Kinase PKR in Human Cells and Transfected Mouse Cells," Experimental Cell Research 218:17-27 (1995).
Kim, et al., "Conversion of pre-RISC to holo-RISC by Ago2 during assembly of RNAi complexes," RNA 13:22-29 (2007).
Koshkin, et al., "LNA (Locked Nucleic Acid): An RNA Mimic Forming Exceedingly Stable LNA:LNA Duplexes," J. Am. Chem. Soc. 120:13252-13253 (1998).
Letter from Vossius & Partner dated Jun. 25, 2007 (Patentee's response).
Liu, et al., "R2D2, A Bridge Between the Initiation and Effector Steps of the *Drosophila* RNAi Pathway," Science 301:1921-1925 (Sep. 26, 2003).
Marques, et al., "Activation of the mammalian immune system by SiRNAs," Nature Biotechnology 23(11):1399-1405 (Nov. 2005).
Matranga, et al., "Passenger-Stranded Cleavage Facilitates Assembly of siRNA into Ago2-Containing RNAi Enzyme Complexes," Cell 123:607-620 (Nov. 18, 2005).
Phillips, "Antisense Inhibition and Adeno-Associated Viral Vector Delivery for Reducing Hypertension," Hypertension 29(1, Part 2):177-187 (Jan. 1997).
Wang, et al., "Delivery of antisense oligodeoxyribonucleotides against the human epidermal growth factor receptor into cultured KB cells with liposomes conjugated to folate via polyethylene glycol," Proc. Natl. Acad. Sci. 92:3318-3322 (Apr. 1995).
Zelphati, et al., "Antisense oligonucleotides in solution or encapsulated in immunoliposomes inhibit replication of HIV-1 by several different mechanisms," Nucleic Acids Research 22(20):4307-4314 (1994).
Lima, et al., "The influence of antisense oligonucleotide-induced RNA structure on *Escherichia coli* RNase HI activity," J. Biol. Chem. 272(29):18191-18199 (Jul. 18, 1997).

Case 1:09-cv-11116-PBS. Document 80. Defendant Whitehead Answer and Counterclaims to the Complaint. Filed Aug. 25, 2009.
Case 1:09-cv-11116-PBS. Document 81. Defendant Massachusetts Institute of Technology's Answer to the Complaint. Filed Aug. 25, 2009.
Case 1:09-cv-11116-PBS. Document 82. Defendant University of Massachusetts Answer to the Complaint and Counterclaims. Filed Aug. 25, 2009.
Case 1:09-cv-11116-PBS. Document 83. Order on Motion for Preliminary Injunction. Filed Sep. 1, 2009.
Case 1:09-cv-11116-PBS. Document 84. Joint Motion for Extension of Time. Filed Sep. 2, 2009.
Case 1:09-cv-11116-PBS. Document 85. Letter/request (non-motion) filed by David Gindler. Filed Sep. 9, 2009.
Case 1:09-cv-11116-PBS. Document 86. Plaintiffs' Reply to Whitehead's Counterclaims. Filed Sep. 17, 2009.
Case 1:09-cv-11116-PBS. Document 87. Plaintiffs' Reply to University of Massachusetts' Counterclaims. Filed Sep. 17, 2009.
Case 1:09-cv-11116-PBS. Document 88. Plaintiffs' Reply to Massachusetts Institute of Technology's Counterclaims. Filed Sep. 17, 2009.
Case 1:09-cv-11116-PBS. Document 89. Joint Motion for Entry of Stipulated Protective Order. Filed Sep. 21, 2009.
Case 1:09-cv-11116-PBS. Document 90. Stipulated Protective Order. Filed Sep. 24, 2009.
Case 1:09-cv-11116-PBS. Document 91. Motion for Leave to Appear Pro Hac Vice (Michael J. Shuster, Ph.D.). Filed Oct. 12, 2009.
Case 1:09-cv-11116-PBS. Document 92. Motion for Leave to Appear Pro Hac Vice (James L. Tuxbury). Filed Oct. 13, 2009.
Case 1:09-cv-11116-PBS. Document 93. Motion for Leave to Appear Pro Hac Vice (Brett R. Tobin). Filed Oct. 13, 2009.
Case 1:09-cv-11116-PBS. Document 94. Motion for Leave to Appear Pro Hac Vice (Marco J. Quina). Filed Oct. 16, 2009.
Case 1:09-cv-11116-PBS. Document 95. Motion for Leave to Appear Pro Hac Vice (Jeremiah S. Helm). Filed Nov. 3, 2009.
Case 1:09-cv-11116-PBS. Document 96. Motion for Leave to Appear Pro Hac Vice (Alan J. Heinrich). Filed Nov. 3, 2009.
Case 1:09-cv-11116-PBS. Document 97. Non-Party Unopposed Motion for Extension of Time to Complete Fact Discovery. Filed Nov. 5, 2009.
Case 1:09-cv-11116-PBS. Document 98. Stipulation re: Expert Discovery. Filed Nov. 9, 2009.
Case 1:09-cv-11116-PBS. Document 99. Certificate of Service. Filed Nov. 10, 2009.
Case 1:09-cv-11116-PBS. Document 100. Joint Motion for Amendments to the Stipulated Protective Orders. Filed Nov. 17, 2009.
Case 1:09-cv-11116-PBS. Document 101. Amendments to Stipulated Protective Orders. Filed Nov. 18, 2009.
Case 1:09-cv-11116-PBS. Document 102. Emergency Motion for Relief from Defendants' Misuse of the Protective Order to block Plaintiffs' In-House Counsel from Attending Inventor Depositions. Filed Nov. 23, 2009.
Case 1:09-cv-11116-PBS. Document 103. Memorandum of Law in Support of Plaintiffs' Emergency Motion for Relief from Defendants' Misuse of the Protective Order to block Plaintiffs' In-House Counsel from Attending Inventor Depositions. Filed Nov. 23, 2009.
Case 1:09-cv-11116-PBS. Document 104. Declaration of Michael J. Strub, Jr. Filed Nov. 23, 2009.
Case 1:09-cv-11116-PBS. Document 105. Motion for Protective Order Respecting Documents Produced by Dr. Brenda Bass. Filed Dec. 7, 2009.
Case 1:09-cv-11116-PBS. Document 106. Protective Order. Filed Dec. 8, 2009.
Case 1:09-cv-11116-PBS. Document 107. Motion for Reconsideration of Order that Documents Produced by Dr. Brenda Bass be Governed by an Amended Protective Order that Would Deprive Plaintiffs' Counsel of the Ability to Effectively Analyze the Documents. Filed Dec. 10, 2009.
Case 1:09-cv-11116-PBS. Document 108. Declaration of Michael H. Strub, Jr. Filed Dec. 10, 2009.
Case 1:09-cv-11116-PBS. Document 109. Defendants' Motion to Strike Plaintiffs' Jury Demand. Filed Dec. 14, 2009.

(56) References Cited

OTHER PUBLICATIONS

Case 1:09-cv-11116-PBS. Document 110. Defendants' Assented to Motion to Impound. Filed Dec. 14, 2009.
Case 1:09-cv-11116-PBS. Document 111. Opposition to Motion for Reconsideration. Filed Dec. 17, 2009.
Case 1:09-cv-11116-PBS. Document 112. Reply to Motion for Reconsideration. Filed Dec. 18, 2009.
Case 1:09-cv-11116-PBS. Document 113. Joint Motion to Modify Certain Pretrial Dates in Scheduling Order. Filed Dec. 21, 2009.
Case 1:09-cv-11116-PBS. Document 114. Defendants' Second Assented to Motion to Seal. Filed Dec. 21, 2009.
Case 1:09-cv-11116-PBS. Document 115. Memorandum in Support of Defendants' Motion to Strike Plaintiffs' Jury Demand. Filed Dec. 22, 2009.
Case 1:09-cv-11116-PBS. Document 117. Plaintiffs' Motion to Seal. Filed Dec. 28, 2009.
Case 1:09-cv-11116-PBS. Document 118. Opposition of Plaintiffs to Defendants' Motion to Strike Jury Demand. Filed Dec. 28, 2009.
Case 1:09-cv-11116-PBS. Document 121. Letter/request (non-motion) by Thomas F. Maffei, P.C. Filed Dec. 30, 2009.
Case 1:09-cv-11116-PBS. Document 122. Plaintiffs' Motion for Leave to File First Amended Complaint. Filed Jan. 4, 2010.
Case 1:09-cv-11116-PBS. Document 123. Plaintiffs' Assented to Motion to Seal. Filed Jan. 4, 2010.
Case 1:09-cv-11116-PBS. Document 124. Defendants' Motion for Leave to File Reply Brief in Support of Motion to Strike Jury Demand. Filed Jan. 4, 2010.
Case 1:09-cv-11116-PBS. Document 125. Defendants' Assented to Motion to Seal. Filed Jan. 5, 2010.
Case 1:09-cv-11116-PBS. Document 126. Reply Brief in Support of Defendants' Motion to Strike Plaintiffs' Jury Demand. Filed Jan. 6, 2010.
Case 1:09-cv-11116-PBS. Document 129. Defendants' Joint Preliminary Exhibit List. Filed Jan. 8, 2010.
Case 1:09-cv-11116-PBS. Document 130. Defendants' Joint Preliminary Exhibit List. Filed Jan. 8, 2010.
Case 1:09-cv-11116-PBS. Document 131. Plaintiffs' Rule 26(a)(3) Disclosures. Filed Jan. 8, 2010.
Case 1:09-cv-11116-PBS. Document 132. Defendants' Joint Preliminary Witness List. Filed Jan. 8, 2010.
Case 1:09-cv-11116-PBS. Document 133. Plaintiffs' Motion to Seal Document. Filed Jan. 12, 2010.
Affidavit of David I. Gindler. Civil Action No. 09-2674-BLS. *Max-Planck-Gesellschaft zur Forderung der Wissenschaften e.V. v. Whitehead Institute for Biomedical Research, et al.* Dated Jun. 29, 2009.
Affidavit of Joern Erselius. Civil Action No. 09-2674-BLS. *Max-Planck-Gesellschaft zur Forderung der Wissenschaften e.V. v. Whitehead Institute for Biomedical Research, et al.* Dated Jun. 30, 2009.
Affidavit of Nancy J. Linck, Ph.D. Civil Action No. 09-2674-BLS. *Max-Planck-Gesellschaft zur Forderung der Wissenschaften e.V. v. Whitehead Institute for Biomedical Research, et al.* Dated Jun. 30, 2009.
Affidavit of Sandra L. Haberny. Civil Action No. 09-2674-BLS. *Max-Planck-Gesellschaft zur Forderung der Wissenschaften e.V. v. Whitehead Institute for Biomedical Research, et al.* Dated Jun. 30, 2009.
Affidavit of Wolfgang Weiss. Civil Action No. 09-2674-BLS. *Max-Planck-Gesellschaft zur Forderung der Wissenschaften e.V. v. Whitehead Institute for Biomedical Research, et al.* Dated Jun. 30, 2009.
Case 1:09-cv-11116-PBS. Declaration of Helen Lockhart and Exhibits. Filed Jul. 14, 2009.
Case 1:09-cv-11116-PBS. Declaration of Kendra P. Robins. Dated Jul. 27, 2009. Filed Jul. 28, 2009.
Case 1:09-cv-11116-PBS. Declaration of Kenneth J. Burchfiel and Exhibits. Filed Jul. 14, 2009.
Case 1:09-cv-11116-PBS. Declaration of Martin Mullins and Exhibits. Filed Jul. 14, 2009.
Case 1:09-cv-11116-PBS. Declaration of Patricia Granahan and Exhibits. Filed Jul. 14, 2009.
Case 1:09-cv-11116-PBS. Declaration of Timothy W. Nilsen and Exhibits. Dated Jul. 24, 2009. Filed Jul. 28, 2009.
Case 1:09-cv-11116-PBS. Defendant Whitehead Institute for Biomedical Research's Answer and Counterclaims to the Complaint. Filed Aug. 25, 2009. (24 pages).
Case 1:09-cv-11116-PBS. Defendant Whitehead Institute for Biomedical Research's Sur-Reply to the Reply Memorandum of Plaintiffs in Support of Motion for Preliminary Injunction. Filed Jul. 28, 2009.
Case 1:09-cv-11116-PBS. Document 29. Opposition of Defendant Board of Trustees of the University of Massachesetts to Plaintiffs' Motion for Preliminary Judgment. Filed Jul. 14, 2009.
Case 1:09-cv-11116-PBS. Document 30. Defendant Whitehead Institute for Biomedical Research's Opposition to Max Planck's and Alnylam's Motion for Temporary Restraining Order and Preliminary Injunction. Filed Jul. 14, 2009.
Case 1:09-cv-11116-PBS. Document 33. Massachusetts Institute of Technology's Opposition to Plaintiffs' Motion for Preliminary Injunction. Filed Jul. 14, 2009.
Case 1:09-cv-11116-PBS. Document 46. Memorandum in Support of Plaintiffs' Motion to Strike Portions of the Affidavit of Kenneth J. Burchfiel. Filed Jul. 21, 2009.
Case 1:09-cv-11116-PBS. Document 47. Reply Memorandum of Plaintiffs in Support of Motion for Preliminary Injunction. Filed Jul. 21, 2009.
Case 1:09-cv-11116-PBS. Document 48. Supplemental Declaration of Wolfgang Weiss, Ph.D. Filed Jul. 21, 2009.
Case 1:09-cv-11116-PBS. Document 49. Supplemental Declaration of Nancy J. Linck. Filed Jul. 21, 2009.
Case 1:09-cv-11116-PBS. Document 50. Supplemental Declaration of Sandra L. Haberny and Exhibits. Filed Jul. 21, 2009.
Case 1:09-cv-11116-PBS. Document 51. Declaration of Thomas Tuschl and Exhibits. Filed Jul. 21, 2009.
Case 1:09-cv-11116-PBS. Document 81. MIT's Answer. Filed Aug. 25, 2009 (17 pages).
Case 1:09-cv-11116-PBS. Document 82. Answer to Complaint and Counterclaim of the University of Massachusetts. Filed Aug. 25, 2009 (21 pages).
Case 1:09-cv-11116-PBS. Document 83. Memorandum and Order by Judge Saris. Dated Sep. 1, 2009 (22 pages).
Case 1:09-cv-11116-PBS. Fourth Supplemental Declaration of Sandra L. Haberny and Exhibits. Filed Aug. 10, 2009 (20 pages).
Case 1:09-cv-11116-PBS. Letter to Judge Saris signed by David Gindler. Mailed Aug. 10, 2009 (4 pages).
Case 1:09-cv-11116-PBS. Plaintiffs' letter to Judge Saris signed by Morgan Chu. Mailed Aug. 3, 2009 (5 pages).
Case 1:09-cv-11116-PBS. Replacement Exhibit 10 to Declaration of Martin Mullins. Filed Jul. 28, 2009.
Case 1:09-cv-11116-PBS. Second Supplemental Declaration of Sandra L. Haberny and Exhibits. Filed Jul. 24, 2009 Li.
Case 1:09-cv-11116-PBS. Supplemental Declaration of Kenneteh J. Burchfiel. Dated Jul. 27, 2009. Filed Jul. 28, 2009.
Case 1:09-cv-11116-PBS. Supplemental Declaration of Patricia Granahan and Exhibits. Filed Jul. 28, 2009.
Case 1:09-cv-11116-PBS. Third Supplementary Declaration of Sandra L. Haberny and Exhibits. Filed Aug. 3, 2009 (36 pages).
Case 1:09-cv-11116-PBS. Whitehead's Opposition to Plaintiffs' Motion to Strike Portions of the Affidavit of Kenneth J. Burchfiel. Filed Jul. 28, 2009.
Case 1:09-cv-11116-PBS. Affidavit of Helen C. Lockhart, Esq. and Exhibits. Filed Jul. 13, 2009.
Case 1:09-cv-11116-PBS. Document 3. Plaintiffs' Motion for Remand and Request for Immediate Hearing. Filed Jul. 10, 2009.
Case 1:09-cv-11116-PBS. Document 9. Plaintiffs' Reply in Support of Motion to Remand. Filed Jul. 22, 2009.
Case 1:09-cv-11116-PBS. Opposition to Plaintiffs' Motion for Remand and Request for Immediate Hearing. Filed Jul. 13, 2009.
Case 1:09-cv-11116-PBS. Transcript of Jul. 30, 2009 motion hearing (30 pages).

(56) References Cited

OTHER PUBLICATIONS

Case 1:09-cv-11116-PBS. Wolf Greenfield & Sacks PC's Sur-Reply in Support of its Opposition to Plaintiffs' Motion for Remand. Filed Jul. 27, 2009.
Case 1-09-cv-11116-PBS. Wolf Greenfield & Sacks PC's Amended Answer to Plaintiffs' First Amended Complaint. Filed Aug. 11, 2009 (8 pages).
Civil Action No. 09-02654-BLS. Affidavit of Joern Erselius and Exhibits. Filed Jul. 9, 2009.
Civil Action No. 09-02654-BLS. Memorandum in Support of Plaintiff's Emergency Motion for a Temporary Restraining Order Against Wolf Greenfield & Sacks, PC. Filed Jul. 10, 2009.
Civil Action No. 09-02654-BLS. Plaintiff's Emergency Motion for a Temporary Restraining Order Against Wolf Greefield & Sacks, PC. Filed Jul. 10, 2009.
Complaint. Civil Action No. 09-2674. *Max-Planck-Gesellschaft zur Forderung der Wissenschaften e.V. v. Whitehead Institute for Biomedical Research, et al.* Dated Jun. 26, 2009.
Memorandum in Support of Max Planck's and Alnylam's Motions for Temporary Restraining Order and Preliminary Injunction. Civil Action No. 09-2674. *Max-Planck-Gesellschaft zur Forderung der Wissenschaften e.V. v. Whitehead Institute for Biomedical Research, et al.* Dated Jun. 30, 2009.
Notice of Opposition to European Patent No. EP 1 144 623 and Opposition papers filed in EPO by Atugen AG on May 28, 2003.
Notice of Opposition to European Patent No. EP 1 144 623 and Opposition papers filed in EPO by Janssen Pharmaceutica N.W. On May 28, 2003.
Plaintiffs' Complaint. Civil Action No. 09-2654. *Max-Planck-Gesellschaft zur Forderung der Wissenschaften e.V. v. Wolf Greenfield & Sacks, PC.* Dated Jun. 26, 2009.
Lu, et al., "Delivering siRNA in vivo for functional genomics and novel therapeutics," RNA Interference Technology, pp. 303-317 (2005).
Samarsky, et al., "RNAi in drug development: Practical considerations," RNA Interference Technology, pp. 384-395 (2005).
Sioud, "siRNA Delivery In Vivo," Methods in Molecular Biology, 309:237-249 (2005).
Wu, et al., "Identification and Partial Purification of Human Double Strand RNase Activity," The Journal of Biological Chemistry, 273(5):2532-2542 (Jan. 30, 1998).
Meister, et al., "Mechanisms of gene silencing by double-stranded RNA," Nature, 431:343-349 (Sep. 16, 2004).
Simeoni, et al., "Peptide-Based Strategy for siRNA Delivery into Mammalian Cells," Methods in Molecular Biology, 309:251-260 (2005).
Zhang, et al., "Single Processing Center Models for Human Dicer and Bacterial RNase III," Cell, 118:57-68 (Jul. 9, 2004).
Amarzguioui, et al., "Tolerance for mutations and chemical modifications in a siRNA," Nucleic Acids Research, 31(2):589-595 (2003).
Jen, et al., "Suppression of Gene Expression by Targeted Disruption of Messenger Rna: . . . ," Stem Cells, 18:307-319 (2000).
Gewirtz, et al., "Nucleic Acid Therapeutics: State of the Art and Future Prospects," Blood, 92(3):712-736 (Aug. 1, 1998).
Tuschl, et al., "Targeted mRNA degradation by double-stranded RNA in vitro," Genes & Development, 13:3191-3197 (1999).
Hammond, et al., "An TNA-directed nuclease mediates post-transcriptional gene silencing in *Drosophila* cells," Nature 404:293-296 (Mar. 16, 2000).
Manche, et al., "Interactions between Double-Stranded RNA Regulators and the Protein Kinase DAI," Molecular and Cellular Biology, 12(11):5238-5248 (Nov. 1992).
Wang, et al., "Inhibition of Trypanosoma brucei Gene Expression by RNA Interference Using an Integratable Vector with Opposing T7 Promoters," The Journal of Biological Chemistry, 275(51):40174-40179 (Dec. 22, 2000).
Case 1:09-cv-11116-PBS. Deposition testimony of Robert Murray; Oct. 26, 2009I associated Exhibits 18 through 26.
Case 1:09-cv-11116-PBS. Deposition testimony of Anne Collins; Oct. 30, 2009I associated Exhibits previously marked 2 through 4 and 530 through 545.
Case 1:09-cv-11116-PBS. Deposition testimony of Winfried Lendeckel; Nov. 19, 2009; associated Exhibits 108 through 114.
Case 1:09-cv-11116-PBS. Deposition testimony of Patricia Granahan; Nov. 17, 2009I associated Exhibits 637 through 645.
Case 1:09-cv-11116-PBS. Deposition testimony of Sayba Elbashir; Nov. 20, 2009; associated Exhibits 163 through 168.
Press Release, Nov. 15, 2001, "AGY Therapeutics Announces Study Demonstrating Utility of RNA Interference in Mammalian Cells for CNS Drug Discovery".
Reviews, "Antisense oligonucleotides: towards clinical trials," 4:376-387 (Oct. 1996).
Ahlquist, "RNA-Dependent RNA Polymerases, Viruses, and Rna Silencing," Science, 296:1270-1273 (May 17, 2002).
Anderson, "Human gene therapy," Nature, 394:25-31 (Apr. 30, 1996).
Bahramian, et al., "Transcriptional and Posttranscriptional Silencing of Rodent α1(I) Collagen by a Homologous . . . ," Molecular and Cellular Biology, pp. 274-283 (Jan. 1999).
Steinberg, "MicroRNA Shows Macro Potential," The Scientist, 17(12, 22):1-9 (Jun. 16, 2003).
Billy, et al., "Specific interference with gene expression induced by long, double-stranded RNA in mouse embryonal . . . ," PNAS, 98(5):14428-14433 (Dec. 4, 2001).
Bosher, et al., "RNA interference: genetic wand and genetic watchdog," Nature Cell Biology, 2:E31-E36 (Feb. 2000).
Branch, "A good antisense molecule is hard to find," TIBS 23:45-50 (Feb. 1998).
Brummelkamp, et al., "A System for Stable Expression of Short Interfering RNAs in Mammalian Cells," Science Express, pp. 1-6 (Mar. 21, 2002).
Caplen, et al., "Specific inhibition of gene expression by small double-stranded RNAs in invertebrate and vertebrate systems," PNAS 98(17):9742-9747 (Aug. 14, 2001).
Carmell, et al., "The Argonaute family: tentacles that reach into RNAi, developmental control, stem cell maintenance, and tumorigenesis," Genes & Development, 16:2733-2742.
Castanotto, et al., "Functional siRNA expression from transfected PCR products," RNA, 8:1454-1460 (2002).
Chiu, et al., "siRNA function in RNAi: A chemical modification analysis," RNA, 9:1034-1048 (2003).
Chiu, et al., "RNAi in Human Cells: Basic Structural and Functional Features of Small Interfering RNA," Molecular Cell, 10:549-561 (Sep. 2002).
Clemens, et al., "Use of double-stranded RNA interference in *Drosophila* cell lines to dissect signal transduction pathways," PNAS, 97(12):6499-6503 (Jun. 6, 2000).
Clemens, et al., "The Double-Stranded RNA-Dependent Protein Kinase PKR: Structure and Function," Journal of Inteferon and Cytokine Research, 17:503-524 (1997).
Corsi, et al., "*Caenorhabditis elegans* Twist plays an essential role in non-striated muscle development," Development, 127:2041-2051 (2000).
Devroe, et al., "Retrovirus-delivered siRNA," BMC Biotechnology, 2:1-5 (2002).
Dichoso, et al., "The MADS-Box Factor CeMEF2 is not Essential for *Caenorhabditis elegans* Myogenesis and Development," Developmental Biology, 223:431-440 (2000).
Elbashir, et al., "Functional anatomy of siRNAs for mediating efficient RNAi in *Drosophila melanogaster* embryo lysate," The EMBO Journal, 20(23):6877-6888 (2001).
Elbashir, et al., "Duplexes of 21-nucleotide RNAs mediate RNA interferences in cultured mammalian cells," Nature, vol. 411 (May 24, 2001).
Elela, et al., "Depletion of yeast Rnase III blocks correct U2 3' end formation and results in polydenylated but functional U2 snRNA," The EMBO Journal, 17(13):3738-3746 (1998).
Escobar, et al., RNAi-mediated oncogene silencing confers resistance to crown gall tumorigenesis, PNAS, 98 (23):13437-13442 (Nov. 6, 2001).

(56) References Cited

OTHER PUBLICATIONS

Filippov, et al., "A novel type of RNase III family proteins in eukaryotes," Gene 245:213-221 (2000).

Gonczy, et al., Functional genomic analysis of cell division in *C. elegans* using RNAi of genes on chromosome III, Nature 408:331-336 (Nov. 16, 2000).

Grishok, et al., "Target dependent accumulation of small RNAs during RNAi in *C. elegans*," International *C. elegans* Meeting, p. 307 (2001).

Grishok and Mello, VI. RNAi and Development References, Abstract, pp. 340-360.

Hammond, et al., "Argonaute2, a Link Between Genetic and Biochemical Analyses of RNAi," Science, 293:1146-1150 (Aug. 10, 2001).

Hsieh, et al., "The RING finger/B-Box factor TAM-1 and a retinoblastoma-like protein LIN-35 modulate context-dependent gene silencing in *Caenorhabditis elegans*," Genes & Development, 13:2958-2970 (1999).

Hsieh, et al., "Recognition and Silencing of Repeated DNA," Annu. Rev. Genet. 34:187-204 (2000).

Hutvagner, et al., "Detailed Characterization of the post-transcriptional gene-silencing-related small RNA in a GUS gene-silenced tobacco," RNA, 6:1445-1454 (2000).

Hutvagner, et al., "In vitro processing of pre-let-7 RNA," Department of Biochemistry & Molecular Pharmacology.

Hutvagner, et al., "A Cellular Function for the RNA-Interference Enzyme Dicer in the Maturation of the let-7 Small Temporal RNA," Science, 293:834-838 (Aug. 3, 2001).

Kostich, et al., "Identification and molecular-genetic characterization of a LAMP/CD68-like protein from *Caenorhabditis elegans*," Journal of Cell Science, 133:2595-2606 (2000).

Lee, et al., "Expression of small intefering RNAs targeted against HIV-1 rev transcripts in human cells," Nature Biotechnology, 19:500-505 (May 2002).

Levin, et al., "Methods of double-stranded RNA-mediated gene inactivation in *Arabidopsis* and their use to define an essential gene in methionine biosynthesis," Plant Molecular Biology, 44:759-775 (2000).

Li, et al., "Induction and Suppression of RNA Silencing by an Animal Virus," Science, 296:1319-1321 (May 17, 2002).

Lin, et al., :Policing rogue genes, Nature, 402:128-129 (Nov. 11, 1999).

Liu, et al., "Essential Roles for *Caenorhabditis elegans* Lamin Gene in Nuclear Organization, Cell Cycle Progression, and Spatial Organization of Nuclear Pore Complexes," Molecular Biology of the Cell, 11:3937-3947 (Nov. 2000).

Liu, et al., "Overlapping roles of two Hox genes and the exd orthology ceh-20 in diversification of the *C. elegans* postembryonic mesoderm," Development, 127:5179-5190 (2000).

McManus, et al., "Gene Silencing using micro-RNA designed hairpins," RNA, 8:842-850 (2002).

McCaffrey, et al., "RNA interference in adult mice," Nature, 418:38-39 (Jul. 4, 2002).

Mercola, et al., "Antisense approaches to cancer gene therapy," Cancer Gene Therapy, 2(1):47-59 (1995).

Moss, "Non-coding RNAs: Lightning strikes twice," Current Biology, 10:R436-R439 (2000).

Nicholson, "Function, mechanism and regulation of bacterial ribonucleases," FEMS Microbiology Reviews, 23:371-390 (1999).

Paddison, et al., "Short hairpin RNAs (shRNAs) induced sequence-specific silencing in mammalian cells," Genes & Development 16:948-958.

Parrish, et al., "Distinct roles for RDE-1 and RDE-4 during RNA interference in *Caenorhabditis elegans*," RNA, 7:1397-1402 (2001).

Pasquinelli, et al., "Conservation of the sequence and temporal expression of let-7 heterochronic regulatory RNA," Nature, 408:86-89 (Nov. 2, 2000).

Paul, et al., "Effective expression of small interfering RNA in human cells," Nature Biotechnology, 29:505-508 (May 2002).

Plasterk, "RNA Silencing: The Genome's Immune System," Science, vol. 296 (May 17, 2002).

Reinhart, et al., "The 21-nucleotide let-7 RNA regulates developmental timing in *Caenorhabditis elegans*," Nature, vol. 403 (Feb. 24, 2000).

Robinson, "RNAi Therapeutics: How Likely, How Soon?" Plas Biology 2(1):0018-0020 (Jan. 2004).

Rotondo, et al., "Substrate structure requirements of the PAC1 rebonuclease from *Schizosaccharomyces pombe*," RNA, 3:1183-1193 (1997).

Schweizer, et al., "Double-stranded RNA interferes with gene function at the single-cell level in cereals," The Plant Journal, 24(6):895-903 (2000).

Sharp, "RNA Interference-2001," Center for Cancer Research and Department of Biology.

Sijen, et al., "On the Role of RNA Amplification in dsRNA-Triggered Gene Silencing," Cell, 107:465-476 (Nov. 16, 2001).

TranSilent siRNA Vector Mix, Product User Manual, release Sep. 24, 2003.

Strauss, "Candidate 'Gene Silencers' Found," Science, 286:886 (Oct. 29, 1999).

Stroz, "An Expanding Universe of Noncoding RNAs," Science, 296:1260-1262 (May 17, 2002).

Sui, et al., "A DNA vector-based RNAi technology to suppress gene expression in mammalian cells," 99(8):5515-5520 (Apr. 16, 2002).

Svoboda, et al., "Selective reduction of dormant maternal mRNAs in mouse oocytes by RNA interference," Development, 127:4147-4156 (2000).

Tenllado, et al., "Double-Stranded RNA-Mediated Interference with Plant Virus Infection," Journal of Virology, 75 (24):12288-12297 (Dec. 2001).

Timmons, et al., "Ingestion of bacterially expressed dsRNAs can produce specific and potent genetic interference in *Caenorhabditis elegans*," Genem 263:103-112 (2001).

Tuschl, RNA Interference and Small Interfering RNAs, Chem Biochem, 2:239-245 (2001).

Verma, et al., "Gene Therapy promises, problems and prospects," Nature, 389:239-242 (Sep. 18, 1997).

Waterhouse, et al., "Virus resistance and gene silencing in plants can be induced by simultaneous expression of sense and antisense RNA," Proc. Nat'l. Acad. Sci., 95:13959-13964 (Nov. 1998).

Yang, et al., "Specific Double-Stranded RNA Interference in Undifferentiated Mouse Embryonic Stem Cells," Molecular and Cellular Biology, 21(22):7807-7816 (Nov. 2001).

Yu, et al., "RNA interference by expression of short-interfering RNAs and hairpin RNAs in mammalian cells," PNAS, 99 (9):6047-6052 (Apr. 30, 2002).

Zamore, "Ancient Pathways Programmed by Small RNAs," Science, 296:1265-1269 (May 17, 2000).

Shiota, et al., "I want to Know the RNAi Protocol of that Animal!— Effective RNAi in Mammal Cells," Cell Engineering, 22(3):310-315 (2003).

Morita, et al., "RNAi Provides a New Tool for Functional Analyses of Mammalian Genes," Proteins, Nucleic Acids and Enzymes, 47(14):1939-1945 (2002).

Kawasaki, et al., "VI. Manipulation of Gene Manifestation, In vitro Dicing and Optimized Express Vectors for siRNA in Mammalian Cells," Proteins, Nucleic Acids and Enzymes, 48(11):1638-1645 (2003).

Opposition Document Reason for Filing—Japanese Patent Application 2001-573036.

Cerutti et al., "Domains in gene silencing and cell differentiation proteins: the novel PAZ domain and redefinition of the Piwi domain", TIBS 25—Oct. 2000, pp. 481-482.

Opposition submission dated Nov. 10, 2010 regarding European Patent No. 1 407 044 (Application No. 01985833.1), opposed by Sirna Therapeutics, Inc. (Opponent 1), 7 pages.

Patentee's submission regarding opposition for EP 1407044 (01985833.1) dated Oct. 1, 2010, 85 pages Xinhua Ji, "The Mechanism of RNase III Action: Now Dicer Dices", Abstract, Macromolecular Crystallography Laboratory, National Cancer Institute, p. 99 (2008).

(56) References Cited

OTHER PUBLICATIONS

Lamontagne et al., "The RNase III Family: A conserved Structure and Expanding Functions in Eukaryotic dsRNA Metabolism", Curr. Issues Mol. Biol. (2001) 3(4), p. 71.

Rotondo et al., "Substrate Structure requirements of the Pac1 ribonuclease from *Schizosaccharomyces pombe*", RNA, (1997), 3: p. 1182.

Takeshita et al., "Homodimeric Structure and Double-stranded RNA Cleavage Activity of the C-terminal RNase III Domain of Human Dicer", J. Mol. Biol. (2007) 374, pp. 106-120.

Opposition submission dated Sep. 29, 2010 regarding European Patent No. 1 407 044 (Application No. 01985833.1), opposed by Pfizer Inc. (Opponent 2), 47 pages.

Hutvagner et al., "Intersection of the RNA interference and small temporal RNA pathways", Meeting Abstract for cold Spring Harbor Symposium on Aug. 22, 2001, Eukaryotic mRNA Processing.

International Search Report dated Oct. 18, 2002 for PCT/US01/10188.

Jarvis, "Optimize transfection of siRNAs for RNAi", TechNotes, 9:6, 2002.

McManus et al., "Gene silencing in mammals by small interfering RNAs", Reviews, vol. 3, pp. 737-747 (2002).

English translation of the Decision in the Patent Invalidation Trial of Japanese Patent No. 4095895, mailed Sep. 28, 2012.

Case 1:11-cv-10484-PBS. Document 71. Transcript of Motion Hearing on May 30, 2012. Release of Transcript Restiction Set for Sep. 10, 2012.

Case 1:11-cv-10484-PBS. Document 73. Defendent's Answer to the University of Utah's Second Amended Complaint filed Jun. 25, 2012.

Proprietor's Response to the Grounds of Appeal, Including the Main and Auxiliary Requests, filed Jan. 7, 2013, in the Opposition Proceedings in EP 1309726.

Wikipedia Entry for "RNaseH" Current as of Jan. 3, 2013, Cited in the Opposition Proceedings in EP 1309726 on Jan. 7, 2013.

a b

| siRNA duplex | | |
|---|---|---|
| uGL2 | 5' CGUACGCGGAAUACUUCGAUU<br>UUGCAUGCGCCUUAUGAAGCU 5' | [SEQ ID NO: 14]<br>[SEQ ID NO: 15] |
| GL2 | 5' CGUACGCGGAAUACUUCGATT<br>TTGCAUGCGCCUUAUGAAGCU 5' | [SEQ ID NO: 16]<br>[SEQ ID NO: 17] |
| GL3 | 5' CUUACGCUGAGUACUUCGATT<br>TTGAAUGCGACUCAUGAAGCU 5' | [SEQ ID NO: 18]<br>[SEQ ID NO: 19] |
| invGL2 | 5' AGCUUCAUAAGGCGCAUGCTT<br>TTUCGAAGUAUUCCGCGUACG 5' | [SEQ ID NO: 20]<br>[SEQ ID NO: 21] |
| RL | 5' AAACAUGCAGAAAAUGCUGTT<br>TTUUUGUACGUCUUUUACGAC 5' | [SEQ ID NO: 22]<br>[SEQ ID NO: 23] |

Fig. 8

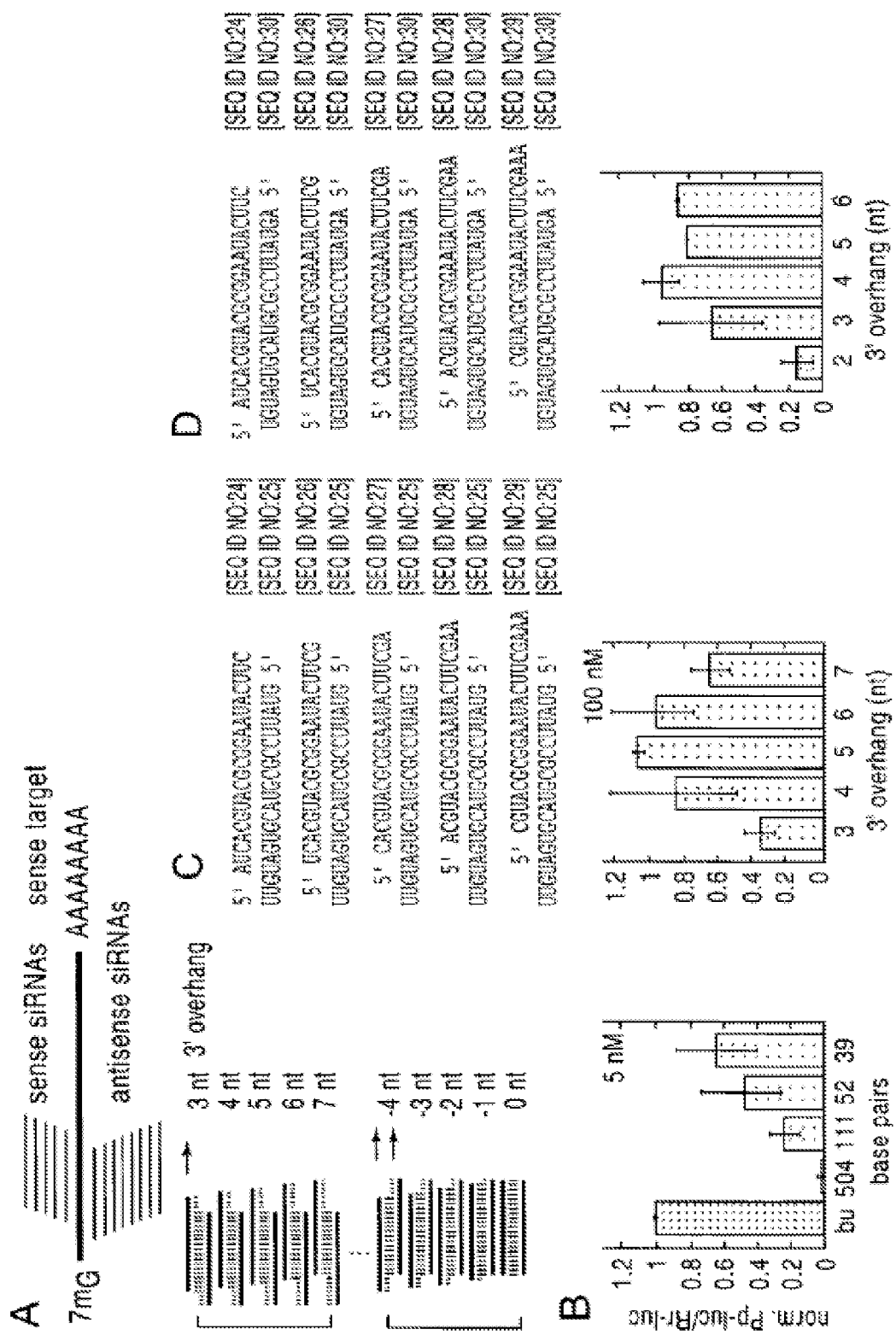
Fig. 11 Part I

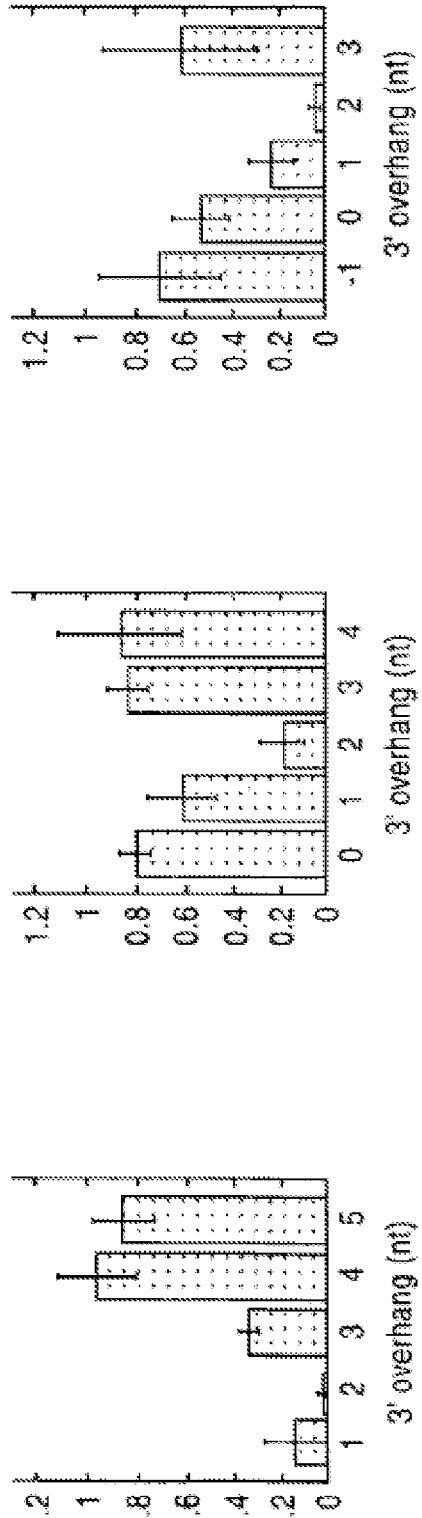
Fig. 11 Part II

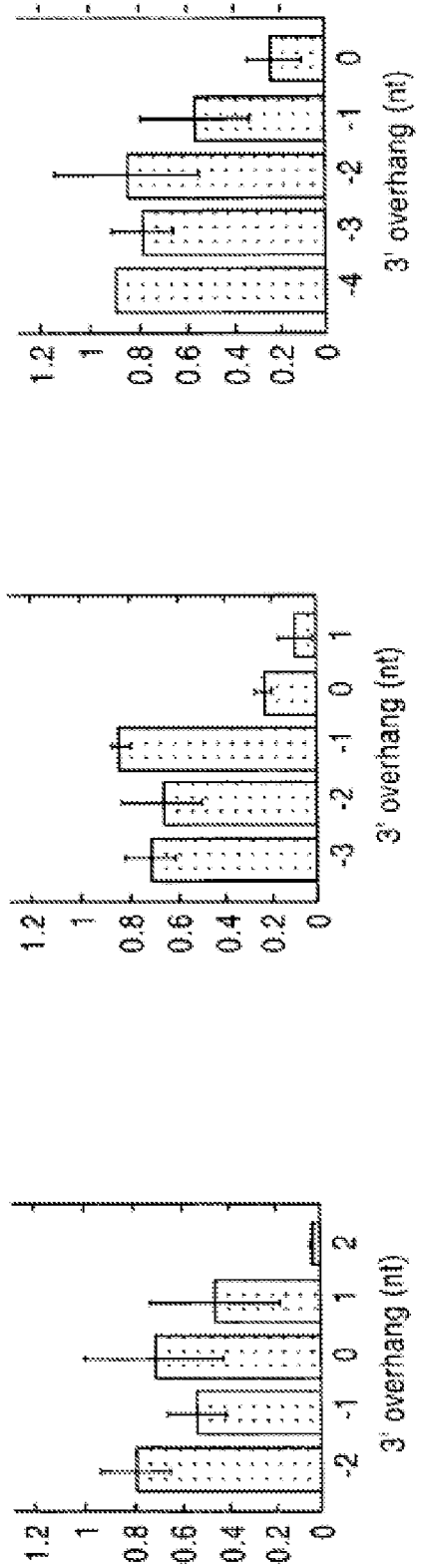
Fig. 11 Part III

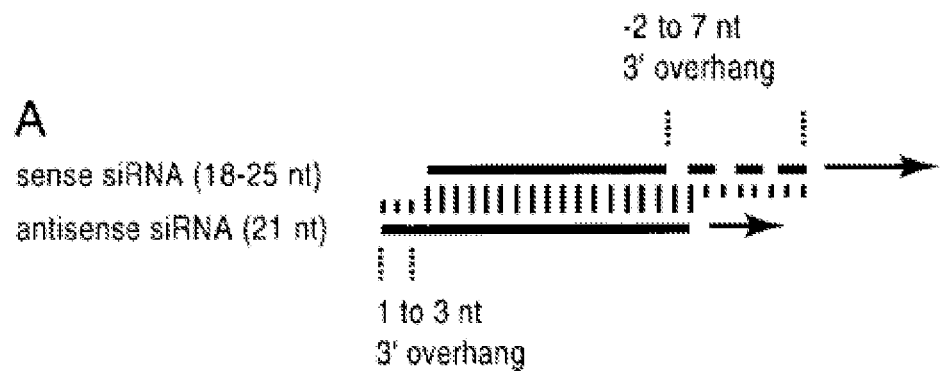

B
```
5' CGUACGCGGAAUACUUCG          [SEQ ID NO: 37]
   UGCAUGCGCCUUAUGAAGCUU 5'    [SEQ ID NO: 38]

5' CGUACGCGGAAUACUUCGA         [SEQ ID NO: 39]
   UGCAUGCGCCUUAUGAAGCUU 5'    [SEQ ID NO: 38]

5' CGUACGCGGAAUACUUCGAA        [SEQ ID NO: 40]
   UGCAUGCGCCUUAUGAAGCUU 5'    [SEQ ID NO: 38]

5' CGUACGCGGAAUACUUCGAAA       [SEQ ID NO: 41]
   UGCAUGCGCCUUAUGAAGCUU 5'    [SEQ ID NO: 38]

5' CGUACGCGGAAUACUUCGAAAU      [SEQ ID NO: 42]
   UGCAUGCGCCUUAUGAAGCUU 5'    [SEQ ID NO: 38]

5' CGUACGCGGAAUACUUCGAAAUG     [SEQ ID NO: 43]
   UGCAUGCGCCUUAUGAAGCUU 5'    [SEQ ID NO: 38]

5' CGUACGCGGAAUACUUCGAAAUGU    [SEQ ID NO: 44]
   UGCAUGCGCCUUAUGAAGCUU 5'    [SEQ ID NO: 38]

5' CGUACGCGGAAUACUUCGAAAUGUC   [SEQ ID NO: 45]
   UGCAUGCGCCUUAUGAAGCUU 5'    [SEQ ID NO: 38]
```

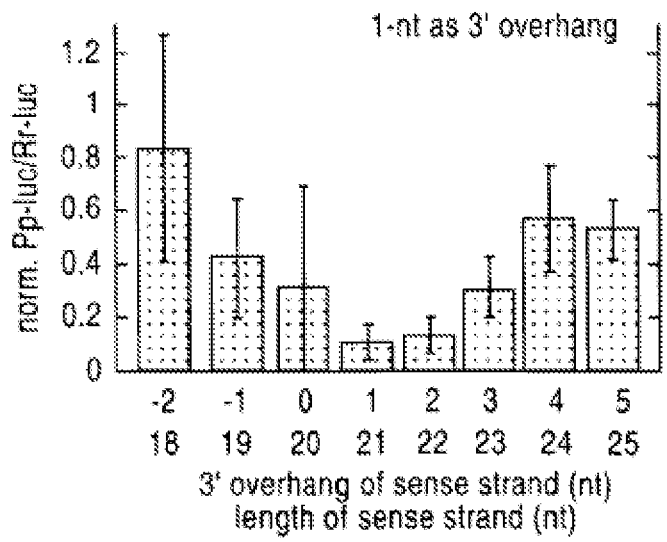

Fig. 12 Part I

C

5' CGUACGCGGAAUACUUCG       [SEQ ID NO: 37]
  GUGCAUGCGCCUUAUGAAGCU 5'  [SEQ ID NO: 46]

5' CGUACGCGGAAUACUUCGA      [SEQ ID NO: 38]
  GUGCAUGCGCCUUAUGAAGCU 5'  [SEQ ID NO: 46]

5' CGUACGCGGAAUACUUCGAA     [SEQ ID NO: 39]
  GUGCAUGCGCCUUAUGAAGCU 5'  [SEQ ID NO: 46]

5' CGUACGCGGAAUACUUCGAAA    [SEQ ID NO: 41]
  GUGCAUGCGCCUUAUGAAGCU 5'  [SEQ ID NO: 46]

5' CGUACGCGGAAUACUUCGAAAU   [SEQ ID NO: 42]
  GUGCAUGCGCCUUAUGAAGCU 5'  [SEQ ID NO: 46]

5' CGUACGCGGAAUACUUCGAAAUG  [SEQ ID NO: 43]
  GUGCAUGCGCCUUAUGAAGCU 5'  [SEQ ID NO: 46]

5' CGUACGCGGAAUACUUCGAAAUGU [SEQ ID NO: 44]
  GUGCAUGCGCCUUAUGAAGCU 5'  [SEQ ID NO: 46]

5' CGUACGCGGAAUACUUCGAAAUGUC [SEQ ID NO: 45]
  GUGCAUGCGCCUUAUGAAGCU 5'  [SEQ ID NO: 46]

D

5' CGUACGCGGAAUACUUCG       [SEQ ID NO: 37]
  AGUGCAUGCGCCUUAUGAAGC 3'  [SEQ ID NO: 47]

5' CGUACGCGGAAUACUUCGA      [SEQ ID NO: 38]
  AGUGCAUGCGCCUUAUGAAGC 3'  [SEQ ID NO: 47]

5' CGUACGCGGAAUACUUCGAA     [SEQ ID NO: 40]
  AGUGCAUGCGCCUUAUGAAGC 3'  [SEQ ID NO: 47]

5' CGUACGCGGAAUACUUCGAAA    [SEQ ID NO: 41]
  AGUGCAUGCGCCUUAUGAAGC 3'  [SEQ ID NO: 47]

5' CGUACGCGGAAUACUUCGAAAU   [SEQ ID NO: 42]
  AGUGCAUGCGCCUUAUGAAGC 3'  [SEQ ID NO: 47]

5' CGUACGCGGAAUACUUCGAAAUG  [SEQ ID NO: 43]
  AGUGCAUGCGCCUUAUGAAGC 3'  [SEQ ID NO: 47]

5' CGUACGCGGAAUACUUCGAAAUGU [SEQ ID NO: 44]
  AGUGCAUGCGCCUUAUGAAGC 3'  [SEQ ID NO: 47]

5' CGUACGCGGAAUACUUCGAAAUGUC [SEQ ID NO: 45]
  AGUGCAUGCGCCUUAUGAAGC 3'  [SEQ ID NO: 47]

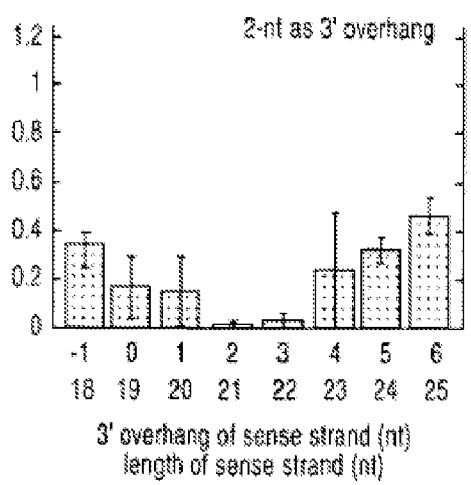
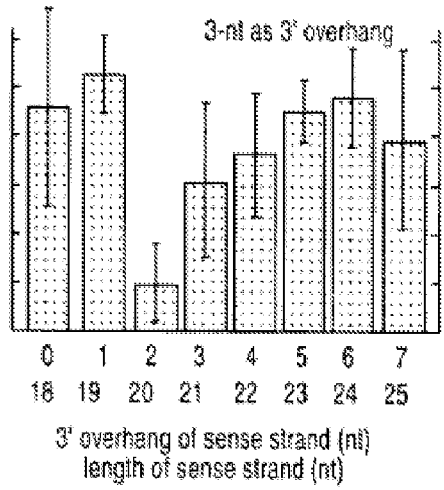

Fig. 12 Part II

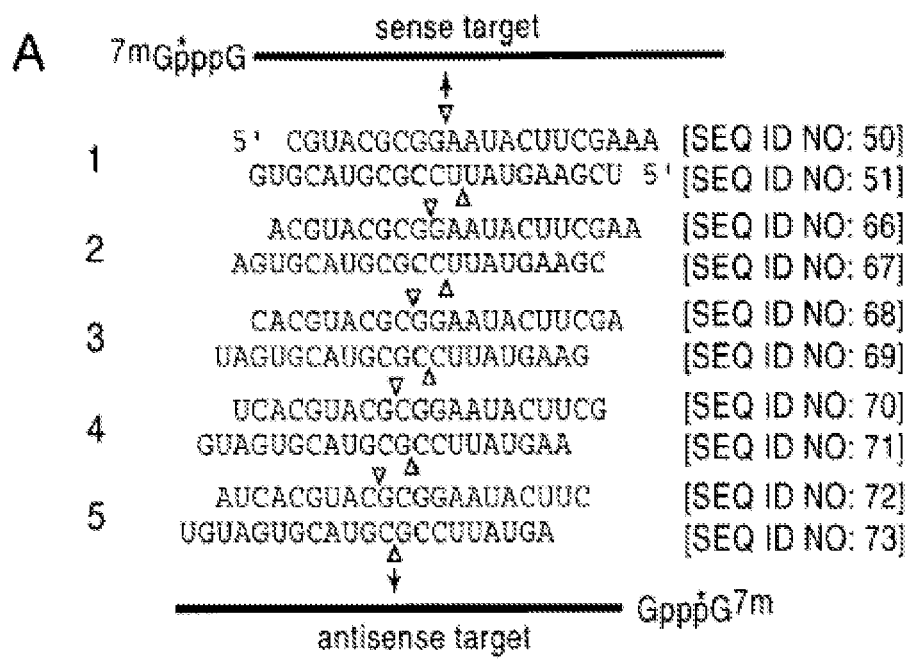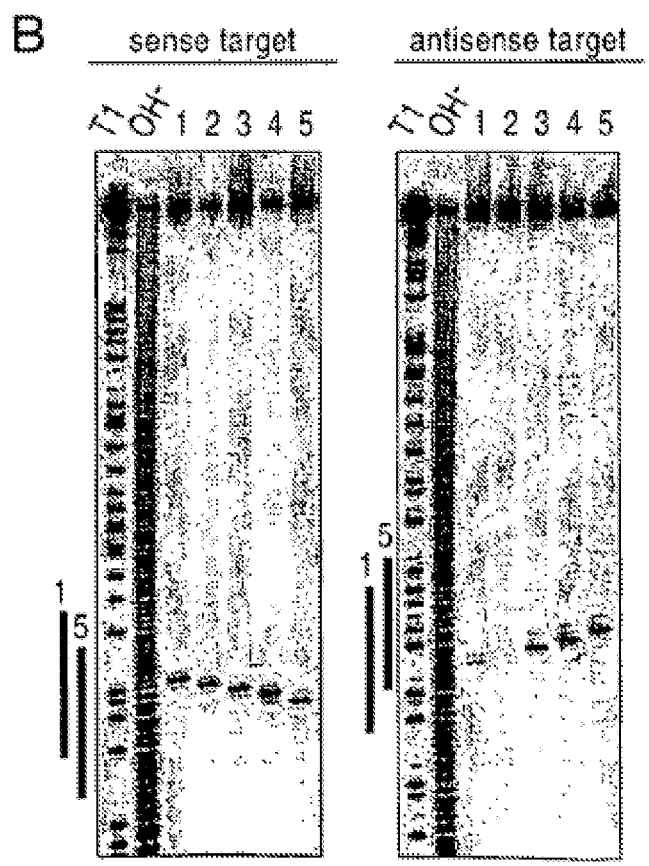
Fig. 15

RNA INTERFERENCE MEDIATING SMALL RNA MOLECULES

CROSS REFERENCE TO RELATED APPLICATION

This application is a continuation of Ser. No. 11/634,129 filed Dec. 6, 2006, which is a Divisional of Ser. No. 10/433,050 filed Jul. 26, 2004, which is a 35 USC §371 National Phase Entry from PCT/EP01/13968 filed Nov. 29, 2001, and designating the US., which claims the benefit of provisional application 60/279,661 filed Mar. 30, 2001 and European Application No. 00126325.0 filed Dec. 1, 2000. All of these applications are incorporated herewith by reference.

DESCRIPTION

The present invention relates to sequence and structural features of double-stranded (ds)RNA molecules required to mediate target-specific nucleic acid modifications such as RNA-interference and/or DNA methylation.

The term "RNA interference" (RNAi) was coined after the discovery that injection of dsRNA into the nematode *C. elegans* leads to specific silencing of genes highly homologous in sequence to the delivered dsRNA (Fire et al., 1998). RNAi was subsequently also observed in insects, frogs (Oelgeschlager et al., 2000), and other animals including mice (Svoboda et al., 2000; Wianny and Zernicka-Goetz, 2000) and is likely to also exist in human. RNAi is closely linked to the post-transcriptional gene-silencing (PTGS) mechanism of co-suppression in plants and quelling in fungi (Catalanotto et al., 2000; Cogoni and Macino, 1999; Dalmay et al., 2000; Ketting and Plasterk, 2000; Mourrain et al., 2000; Smardon et al., 2000) and some components of the RNAi machinery are also necessary for post-transcriptional silencing by co-suppression (Catalanotto et al., 2000; Dernburg et al., 2009; Ketting and Plasterk, 2000). The topic has also been reviewed recently (Bass, 2000; Bosher and Labouesse, 2000; Fire, 1999; Plasterk and Ketting, 2000; Sharp, 1999; Sijen and Kooter, 2000), see also the entire issue of Plant Molecular Biology, vol. 43, issue 2/3, (2000).

In plants, in addition to PTGS, introduced transgenes can also lead to transcriptional gene silencing via RNA-directed DNA methylation of cytosines (see references in Wassenegger, 2000). Genomic targets as short as 30 bp are methylated in plants in an RNA-directed manner (Pelissier, 2000). DNA methylation is also present in mammals.

The natural function of RNAi and co-suppression appears to be protection of the genome against invasion by mobile genetic elements such as retro-transposons and viruses which produce aberrant RNA or dsRNA in the host cell when they become active (Jensen et al., 1999; Ketting et al., 1999; Ratcliff et al., 1999; Tabara et al., 1999). Specific mRNA degradation prevents transposon and virus replication although some viruses are able to overcome or prevent this process by expressing proteins that suppress PTGS (Lucy et al.; 2000; Voinnet et al., 2000).

DsRNA triggers the specific degradation of homologous RNAs only within the region of identity with the dsRNA (Zamore et al., 2000). The dsRNA is processed to 21-23 nt RNA fragments and the target RNA cleavage sites are regularly spaced 21-23 nt apart. It has therefore been suggested that the 21-23 nt fragments are the guide RNAs for target recognition (Zamore et al., 2000). These short RNAs were also detected in extracts prepared from *D. melanogaster* Schneider 2 cells which were transfected with dsRNA prior to cell lysis (Hammond et al., 2000), however, the fractions that displayed sequence-specific nuclease activity also contained a large fraction of residual dsRNA. The role of the 21-23 nt fragments in guiding mRNA cleavage is further supported by the observation that 21-23 nt fragments isolated from processed dsRNA are able, to some extent, to mediate specific mRNA degradation (Zamore et al., 2000). RNA molecules of similar size also accumulate in plant tissue that exhibits PTGS (Hamilton and Baulcombe, 1999).

Here, we use the established *Drosophila* in vitro system (Tuschl et al., 1999; Zamore et al., 2000) to further explore the mechanism of RNAi. We demonstrate that short 21 and 22 nt RNAs, when base-paired with 3' overhanging ends, act as the guide RNAs for sequence-specific mRNA degradation. Short 30 bp dsRNAs are unable to mediate RNAi in this system because they are no longer processed to 21 and 22 nt RNAs. Furthermore, we defined the target RNA cleavage sites relative to the 21 and 22 nt short interfering RNAs (siRNAs) and provide evidence that the direction of dsRNA processing determines whether a sense or an antisense target RNA can be cleaved by the produced siRNP endonuclease complex. Further, the siRNAs may also be important tools for transcriptional modulating, e.g. silencing of mammalian genes by guiding DNA methylation.

Further experiments in human in vivo cell culture systems (HeLa cells) show that double-stranded RNA molecules having a length of preferably from 19-25 nucleotides have RNAi activity. Thus, in contrast to the results from *Drosophila* also 24 and 25 nt long double-stranded RNA molecules are efficient for RNAi.

The object underlying the present invention is to provide novel agents capable of mediating target-specific RNA interference or other target-specific nucleic acid modifications such as DNA methylation, said agents having an improved efficacy and safety compared to prior art agents.

The solution of this problem is provided by an isolated double-stranded RNA molecule, wherein each RNA strand has a length from 19-25, particularly from 19-23 nucleotides, wherein said RNA molecule is capable of mediating target-specific nucleic acid modifications, particularly RNA interference and/or DNA methylation. Preferably at least one strand has a 3'-overhang from 1-5 nucleotides, more preferably from 1-3 nucleotides and most preferably 2 nucleotides. The other strand may be blunt-ended or has up to 6 nucleotides 3' overhang. Also, if both strands of the dsRNA are exactly 21 or 22 nt, it is possible to observe some RNA interference when both ends are blunt (0 nt overhang). The RNA molecule is preferably a synthetic RNA molecule which is substantially free from contaminants occurring in cell extracts, e.g. from *Drosophila* embryos. Further, the RNA molecule is preferably substantially free from any non-target-specific contaminants, particularly non-target-specific RNA molecules e.g. from contaminants occurring in cell extracts.

Further, the invention relates to the use of isolated double-stranded RNA molecules, wherein each RNA strand has a length from 19-25 nucleotides, for mediating, target-specific nucleic acid modifications, particularly RNAi, in mammalian cells, particularly in human cells.

Surprisingly, it was found that synthetic short double-stranded RNA molecules particularly with overhanging 3'-ends are sequence-specific mediators of RNAi and mediate efficient target-RNA cleavage, wherein the cleavage site is located near the center of the region spanned by the guiding short RNA.

Preferably, each strand of the RNA molecule has a length from 20-22 nucleotides (or 20-25 nucleotides in mammalian cells), wherein the length of each strand may be the same or different. Preferably, the length of the 3'-overhang reaches from 1-3 nucleotides, wherein the length of the overhang may be the same or different for each strand. The RNA-strands preferably have 3'-hydroxyl groups. The 5'-terminus preferably comprises a phosphate, diphosphate, triphosphate or hydroxyl group. The most effective dsRNAs are composed of two 21 nt strands which are paired such that 1-3, particularly 2 nt 3' overhangs are present on both ends of the dsRNA.

The target RNA cleavage reaction guided by siRNAs is highly sequence-specific. However, not all positions of a siRNA contribute equally to target recognition. Mismatches in the center of the siRNA duplex are most critical and essentially abolish target RNA cleavage. In contrast, the 3' nucleotide of the siRNA strand (e.g. position 21) that is complementary to the single-stranded target RNA, does not contribute to specificity of the target recognition. Further, the sequence of the unpaired 2-nt 3' overhang of the siRNA strand with the same polarity as the target RNA is not critical for target RNA cleavage as only the antisense siRNA strand guides target recognition. Thus, from the single-stranded overhanging nucleotides only the penultimate position of the antisense siRNA (e.g. position 20) needs to match the targeted sense mRNA.

Surprisingly, the double-stranded RNA molecules of the present invention exhibit a high in vivo stability in serum or in growth medium for cell cultures. In order to further enhance the stability, the 3'-overhangs may be stabilized against degradation, e.g. they may be selected such that they consist of purine nucleotides, particularly adenosine or guanosine nucleotides. Alternatively, substitution of pyrimidine nucleotides by modified analogues, e.g. substitution of uridine 2 nt 3' overhangs by 2'-deoxythymidine is tolerated and does not affect the efficiency of RNA interference. The absence of a 2' hydroxyl significantly enhances the nuclease resistance of the overhang in tissue culture medium.

In an especially preferred embodiment of the present invention the RNA molecule may contain at least one modified nucleotide analogue. The nucleotide analogues may be located at positions where the target-specific activity, e.g. the RNAi mediating activity is not substantially effected, e.g. in a region at the 5'-end and/or the 3'-end of the double-stranded RNA molecule. Particularly, the overhangs may be stabilized by incorporating modified nucleotide analogues.

Preferred nucleotide analogues are selected from sugar- or backbone-modified ribonucleotides. It should be noted, however, that also nucleobase-modified ribonucleotides, i.e. ribonucieotides, containing a non-naturally occurring nucleobase instead of a naturally occurring nucleobase such as uridines or cytidines modified at the 5-position, e.g. 5-(2-amino) propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. In preferred sugar-modified ribonucleotides the 2' OH-group is replaced by a group selected from H, OR, R, halo, SH, SR, $NH_2$, NHR, $NR_2$, or CN, wherein R is $C_1$-$C_6$, alkyl, alkenyl or alkynyl and halo is F, Cl, Br or I. In preferred backbone-modified ribonucleotides the phosphoester group connecting to adjacent ribonucleotides is replaced by a modified group, e.g. of phosphothioate group. It should be noted that the above modifications may be combined.

The sequence of the double-stranded RNA molecule of the present invention has to have a sufficient identity to a nucleic acid target molecule in order to mediate target-specific RNAi and/or DNA methylation. Preferably, the sequence has an identity of at least 50%, particularly of at least 70% to the desired target molecule in the double-stranded portion of the RNA molecule. More preferably, the identity is at least 85% and most preferably 100% in the double-stranded portion of the RNA molecule. The identity of a double-stranded RNA molecule to a predetermined nucleic acid target molecule, e.g. an mRNA target molecule may be determined as follows:

$$I = \frac{n}{L} \times 100$$

wherein I is the identity in percent, n is the number of identical nucleotides in the double-stranded portion of the dsRNA and the target and L is the length of the sequence overlap of the double-stranded portion of the dsRNA and the target.

Alternatively, the identity of the double-stranded RNA molecule to the target sequence may also be defined including the 3' overhang, particularly an overhang having a length from 1-3 nucleotides. In this case the sequence identity is preferably at least 50%, more preferably at least 70% and most preferably at least 85% to the target sequence. For example, the nucleotides from the 3' overhang and up to 2 nucleotides from the 5' and/or 3' terminus of the double strand may be modified without significant loss of activity.

The double-stranded RNA molecule of the invention may be prepared by a method comprising the steps:
(a) synthesizing two RNA strands each having a length from 19-25, e.g. from 19-23 nucleotides, wherein said RNA strands are capable of forming a double-stranded RNA molecule, wherein preferably at least one strand has a 3'-overhang from 1-5 nucleotides,
(b) combining the synthesized RNA strands under conditions, wherein a double-stranded RNA molecule is formed, which is capable of mediating target-specific nucleic acid modifications, particularly RNA interference and/or DNA methylation.

Methods of synthesizing RNA molecules are known in the art. In this context, it is particularly referred to chemical synthesis methods as described in Verma and Eckstein (1998).

The single-stranded RNAs can also be prepared by enzymatic transcription from synthetic DNA templates or from DNA plasmids isolated from recombinant bacteria. Typically, phage RNA polymerases are used such as T7, T3 or SP6 RNA polymerase (Milligan and Uhlenbeck (1989)).

A further aspect of the present invention relates to a method of mediating target-specific nucleic acid modifications, particularly RNA interference and/or DNA methylation in a cell or an organism comprising the steps:
(a) contacting the cell or organism with the double-stranded RNA molecule of the invention under conditions wherein target-specific nucleic acid modifications may occur and,
(b) mediating a target-specific nucleic acid modification effected by the double-stranded RNA towards a target nucleic acid having a sequence portion substantially corresponding to the double-stranded RNA.

Preferably the contacting step (a) comprises introducing the double-stranded RNA molecule into a target cell, e.g. an isolated target cell, e.g. in cell culture, a unicellular microorganism or a target cell or a plurality of target cells within a multicellular organism. More preferably, the introducing step comprises a carrier-mediated delivery, e.g. by liposomal carriers or by injection.

The method of the invention may be used for determining the function of a gene in a cell or an organism or even for modulating the function of a gene in a cell or an organism, being capable of mediating RNA interference. The cell is preferably a eukaryotic cell or a cell line, e.g. a plant cell or an animal cell, such as a mammalian cell, e.g. an embryonic cell; a pluripotent stem cell, a tumor cell, e.g. a teratocarcinoma cell or a virus-infected cell. The organism is preferably a eukaryotic organism, e.g. a plant or an animal, such as a mammal, particularly a human.

The target gene to which the RNA molecule of the invention is directed may be associated with a pathological condition. For example, the gene may be a pathogen-associated gene, e.g. a viral gene, a tumor-associated gene or an autoimmune disease-associated gene. The target gene may also be a heterologous gene expressed in a recombinant cell or a genetically altered organism. By determining or modulating, particularly, inhibiting the function of such a gene valuable information and therapeutic benefits in the agricultural field or in the medicine or veterinary medicine field may be obtained.

The dsRNA is usually administered as a pharmaceutical composition. The administration may be carried out by known methods, wherein a nucleic acid is introduced into a desired target cell in vitro or in vivo. Commonly used gene transfer techniques include calcium phosphate, DEAE-dextran, electroporation and microinjection and viral methods (Graham, F. L. and van der Eb, A. J. (1973), Virol. 52, 456; McCutchan, J. H. and Pagano, J. S. (1968), J. Natl. Cancer Inst. 41, 351; Chu, G. et al (1987), Nucl. Acids Res. 15, 1311; Fraley, R. et al. (1980), J. Biol. Chem. 255, 10431; Capecchi, M. R. (1980), Cell 22, 479). A recent addition to this arsenal of techniques for the introduction of DNA into cells is the use of cationic liposomes (Feigner, P. L. et al. (1987), Proc. Natl. Acad. Sci. USA 84, 7413). Commercially available cationic lipid formulations are e.g. Tfx 50 (Promega) or Lipofectamin 2000 (Life Technologies).

Thus, the invention also relates to a pharmaceutical composition containing as an active agent at least one double-stranded RNA molecule as described above and a pharmaceutical carrier. The composition may be used for diagnostic and for therapeutic applications in human medicine or in veterinary medicine.

For diagnostic or therapeutic applications, the composition may be in form of a solution, e.g. an injectable solution, a cream, ointment, tablet, suspension or the like. The composition may be administered in any suitable way, e.g. by injection, by oral, topical, nasal, rectal application etc. The carrier may be any suitable pharmaceutical carrier. Preferably, a carrier is used, which is capable of increasing the efficacy of the RNA molecules to enter the target-cells. Suitable examples of such carriers are liposomes, particularly, cationic liposomes. A further preferred administration method is injection.

A further preferred application of the RNAi method is a functional analysis of eukaryotic cells, or eukaryotic non-human organisms, preferably mammalian cells or organisms and most preferably human cells, e.g. cell lines such as HeLa or 293 or rodents, e.g. rats and mice. By transfection with suitable double-stranded RNA molecules which are homologous to a predetermined target gene or DNA molecules encoding a suitable double-stranded RNA molecule a specific knockout phenotype can be obtained in a target cell, e.g. in cell culture or in a target organism. Surprisingly it was found that the presence of short double-stranded RNA molecules does not result in an interferon response from the host cell or host organism.

Thus, a further subject matter of the invention is a eukaryotic cell or a eukaryotic non-human organism exhibiting a target gene-specific knockout phenotype comprising an at least partially deficient expression of at least one endogeneous target gene wherein said cell or organism is transfected with at least one double-stranded RNA molecule capable of inhibiting the expression of at least one endogeneous target or with a DNA encoding at least one double stranded RNA molecule capable of inhibiting the expression of at least one endogeneous target gene. It should be noted that the present invention allows a target-specific knockout of several different endogeneous genes due to the specificity of RNAi.

Gene-specific knockout phenotypes of cells or non-human organisms, particularly of human cells or non-human mammals may be used in analytic procedures, e.g. in the functional and/or phenotypical analysis of complex physiological processes such as analysis of gene expression profiles and/or proteomes. For example, one may prepare the knock-out phenotypes of human genes in cultured cells which are assumed to be regulators of alternative splicing processes. Among these genes are particularly the members of the SR splicing factor family, e.g. ASF/SF2, SC35, SRp20, SRp40 or SRp55. Further, the effect of SR proteins on the mRNA profiles of predetermined alternatively spliced genes such as CD44 may be analyzed. Preferably the analysis is carried out by high-throughput methods using oligonucleotide based chips.

Using RNAi based knockout technologies, the expression of an endogeneous target gene may be inhibited in a target cell or a target organism. The endogeneous gene may be complemented by an exogeneous target nucleic acid coding for the target protein or a variant or mutated form of the target protein, e.g. a gene or a cDNA, which may optionally be fused to a further nucleic acid sequence encoding a detectable peptide or polypeptide, e.g. an affinity tag, particularly a multiple affinity tag. Variants or mutated forms of the target gene differ from the endogeneous target gene in that they encode a gene product which differs from the endogeneous gene product on the amino acid level by substitutions, insertions and/or deletions of single or multiple amino acids. The variants or mutated forms may have the same biological activity as the endogeneous target gene. On the other hand, the variant or mutated target gene may also have a biological activity, which differs from the biological activity of the endogeneous target gene, e.g. a partially deleted activity, a completely deleted activity, an enhanced activity etc.

The complementation may be accomplished by coexpressing the polypeptide encoded by the exogeneous nucleic acid, e.g. a fusion protein comprising the target protein and the affinity tag and the double stranded RNA molecule for knocking out the endogeneous gene in the target cell. This coexpression may be accomplished by using a suitable expression vector expressing both the polypeptide encoded by the exogeneous nucleic acid, e.g. the tag-modified target protein and the double stranded RNA molecule or alternatively by using a combination of expression vectors. Proteins and protein complexes which are synthesized de novo in the target cell will contain the exogeneous gene product, e.g. the modified fusion protein. In order to avoid suppression of the exogeneous gene product expression by the RNAi duplex molecule, the nucleotide sequence encoding the exogeneous nucleic acid may be altered on the DNA level (with or without causing mutations on the amino acid level) in the part of the sequence which is homologous to the double stranded RNA molecule. Alternatively, the endogeneous target gene may be complemented by corresponding nucleotide sequences from other species, e.g. from mouse.

Preferred applications for the cell or organism of the invention is the analysis of gene expression profiles and/or proteomes. In an especially preferred embodiment an analysis of a variant or mutant form of one or several target proteins is carried out, wherein said variant or mutant forms are reintroduced into the cell or organism by an exogenous target nucleic acid as described above. The combination of knockout of an endogenous gene and rescue by using mutated, e.g. partially deleted exogenous target has advantages compared to the use of a knockout cell. Further, this method is particularly suitable for identifying functional domains of the target protein. In a further preferred embodiment a comparison, e.g. of gene expression profiles and/or proteomes and/or phenotypic characteristics of at least two cells or organisms is carried out.

These organisms are selected from:
(i) a control cell or control organism without target gene inhibition,
(ii) a cell or organism with target gene inhibition and
(iii) a cell or organism with target inhibition plus target gene complementation by an exogenous target nucleic acid.

The method and cell of the invention are also suitable in a procedure for identifying and/or characterizing pharmacological agents, e.g. identifying new pharmacological agents from a collection of test substances and/characterizing mechanisms of action and/or side effects of known pharmacological agents.

Thus, the present invention also relates to a system for identifying and/or characterizing pharmacological agents acting on at least one target protein comprising:
(a) a eukaryotic cell or a eukaryotic non-human organism capable of expressing at least one endogenous target gene coding for said target protein,
(b) at least one double-stranded RNA molecule capable of inhibiting the expression of said at least one endogenous target gene, and
(c) a test substance or a collection of test substances wherein pharmacological properties of said test substance or said collection are to be identified and/or characterized.

Further, the system as described above preferably comprises:
(d) at least one exogenous target nucleic acid coding for the target protein or a variant or mutated form of the target protein wherein said exogenous target nucleic acid differs from the endogenous target gene on the nucleic acid level such that the expression of the exogenous target nucleic acid is substantially less inhibited by the double stranded RNA molecule than the expression of the endogenous target gene.

Furthermore, the RNA knockout complementation method may be used for preparative purposes, e.g. for the affinity purification of proteins or protein complexes from eukaryotic cells, particularly mammalian cells and more particularly human cells. In this embodiment of the invention, the exogeneous target nucleic acid preferably codes for a target protein which is fused to an affinity tag.

The preparative method may be employed for the purification of high molecular weight protein complexes which preferably have a mass of ≤150 kD and more preferably of ≤500 kD and which optionally may contain nucleic acids such as RNA. Specific examples are the heterotrimeric protein complex consisting of the 20 kD, 60 kD and 90 kD proteins of the U4/U6 snRNP particle, the splicing factor SF3b from the 17S U2 snRNP consisting of 5 proteins having molecular weights of 14, 49, 120, 145 and 155 kD and the 25S U4/U6/U5 tri-snRNP particle containing the U4, U5 and U6 snRNA molecules and about 30 proteins, which has a molecular weight of about 1.7 MD.

This method is suitable for functional proteome analysis in mammalian cells, particularly human cells.

Further, the present invention is explained in more detail in the following figures and examples.

FIGURE LEGENDS

FIG. 1: Double-stranded RNA as short as 38 bp can mediate RNAi. (A) Graphic representation of dsRNAs used for targeting Pp-luc mRNA. Three series of blunt-ended dsRNAs covering a range of 29 to 504 bp were prepared. The position of the first nucleotide of the sense strand of the dsRNA is indicated relative to the start codon of Pp-luc mRNA (p1). (B) RNA interference assay (Tuschl et al., 1999). Ratios of target Pp-luc to control Rr-luc activity were normalized to a buffer control (black bar). dsRNAs (5 nM) were preincubated in *Drosophila* lysate for 15 min at 25° C. prior to the addition of 7-methyl-guanosine-capped Pp-luc and Rr-luc mRNAs (~50 pm). The incubation was continued for another hour and then analyzed by the dual luciferase assay (Promega). The data are the average from at least four independent experiments±standard deviation.

Figure 2:
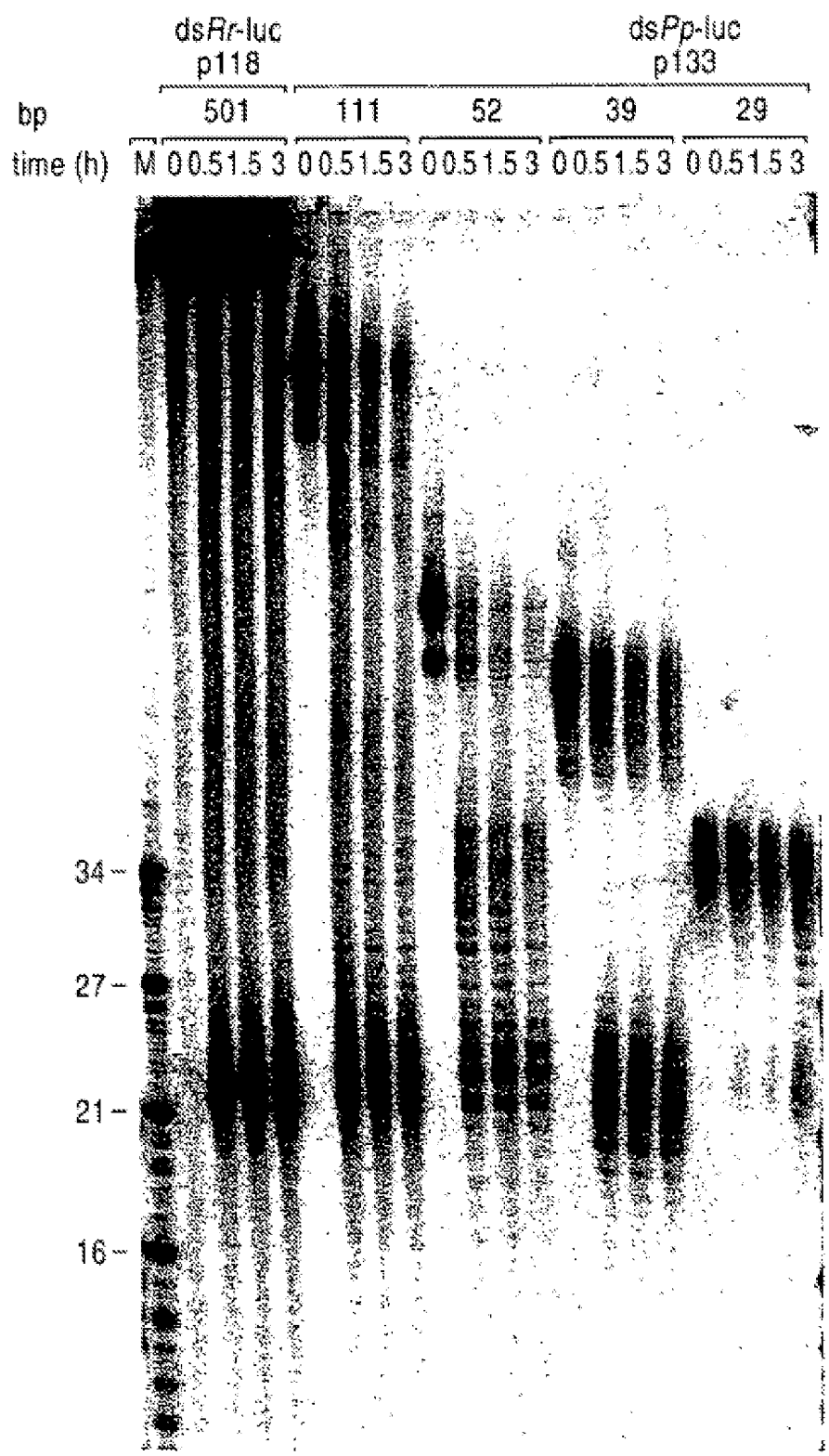

FIG. 2: A 29 bp dsRNA is no longer processed to 21-23 nt fragments. Time course of 21-23 mer formation from processing of internally $^{32}$P-labeled dsRNAs (5 nM) in the *Drosophila* lysate. The length and source of the dsRNA are indicated. An RNA size marker (M) has been loaded in the left lane and the fragment sizes are indicated. Double bands at time zero are due to incompletely denatured dsRNA.

FIG. 3: Short dsRNAs cleave the mRNA target only once.
(A) Denaturing gel electrophoreses of the stable 5' cleavage products produced by 1 h incubation of 10 nM sense or antisense RNA $^{32}$P-labeled at the cap with 10 nM dsRNAs of the p133 series in *Drosophila* lysate.

Length markers were generated by partial nuclease T1 digestion and partial alkaline hydrolysis (OH) of the cap-labeled target RNA. The regions targeted by the dsRNAs are indicated as black bars on both sides. The 20-23 nt spacing between the predominant cleavage sites for the 111 bp long dsRNA is shown. The horizontal arrow indicates unspecific cleavage not due to RNAi. (B) Position of the cleavage sites on sense and antisense target RNAs. The sequences of the capped 177 nt sense and 180 nt antisense target RNAs are represented in antiparallel orientation such that complementary sequence are opposing each other. The region targeted by the different dsRNAs are indicated by differently colored bars positioned between sense and antisense target sequences. Cleavage sites are indicated by circles: large circle for strong cleavage, small circle for weak cleavage. The $^{32}$P-radiolabeled phosphate group is marked by an asterisk.

FIG. 4: 21 and 22 nt RNA fragments are generated by an RNase III-like mechanism.
(A) Sequences of ~21 nt RNAs after dsRNA processing. The ~21 nt RNA fragments generated by dsRNA processing were directionally cloned and sequenced. Oligoribonucleotides originating from the sense strand of the dsRNA are indicated as blue lines, those originating from the antisense strand as red lines. Thick bars are used if the same sequence was present in multiple clones, the number at the right indicating the frequency. The target RNA cleavage sites mediated by the dsRNA are indicated as orange circles, large circle for strong cleavage, small circle for weak cleavage (see FIG. 3B). Circles on top of the sense strand indicated cleavage sites within the sense target and circles at the bottom of the dsRNA indicate cleavage sites in the antisense target. Up to five additional nucleotides were identified in ~21 nt fragments derived from the 3' ends of the dsRNA. These nucleotides are random combinations of predominantly C, G, or A residues and were most likely added in an untemplated fashion during T7 transcription of the dsRNA-constituting strands. (B) Two-dimensional TLC analysis of the nucleotide composition of ~21 nt RNAs. The ~21 nt RNAs were generated by incubation of internally radiolabeled 504 bp Pp-luc dsRNA in *Drosophila* lysate, gel-purified, and then digested to mononucleotides with nuclease P1 (top row) or ribonuclease T2 (bottom row). The dsRNA was internally radiolabeled by transcription in the presence of one of the indicated $\alpha$-$^{32}$P nucleoside triphosphates. Radioactivity was detected by phosphorimaging. Nucleoside 5'-monophosphates, nucleoside 3'-monophosphates, nucleoside 5',3'-diphosphates, and inorganic phosphate are indicated as pN, Np, pNp, and $p_i$, respectively. Black circles indicate UV-absorbing spots from non-radioactive carrier nucleotides. The 3',5'-bisphosphates (red circles) were identified by co-migration with radiolabeled standards prepared by 5'-phosphorylation of nucleoside 3'-monophosphates with T4 polynucleotide kinase and $\gamma$-$^{32}$P-ATP.

FIG. 5: Synthetic 21 and 22 nt RNAs Mediate Target RNA Cleavage.

Figure 4A:
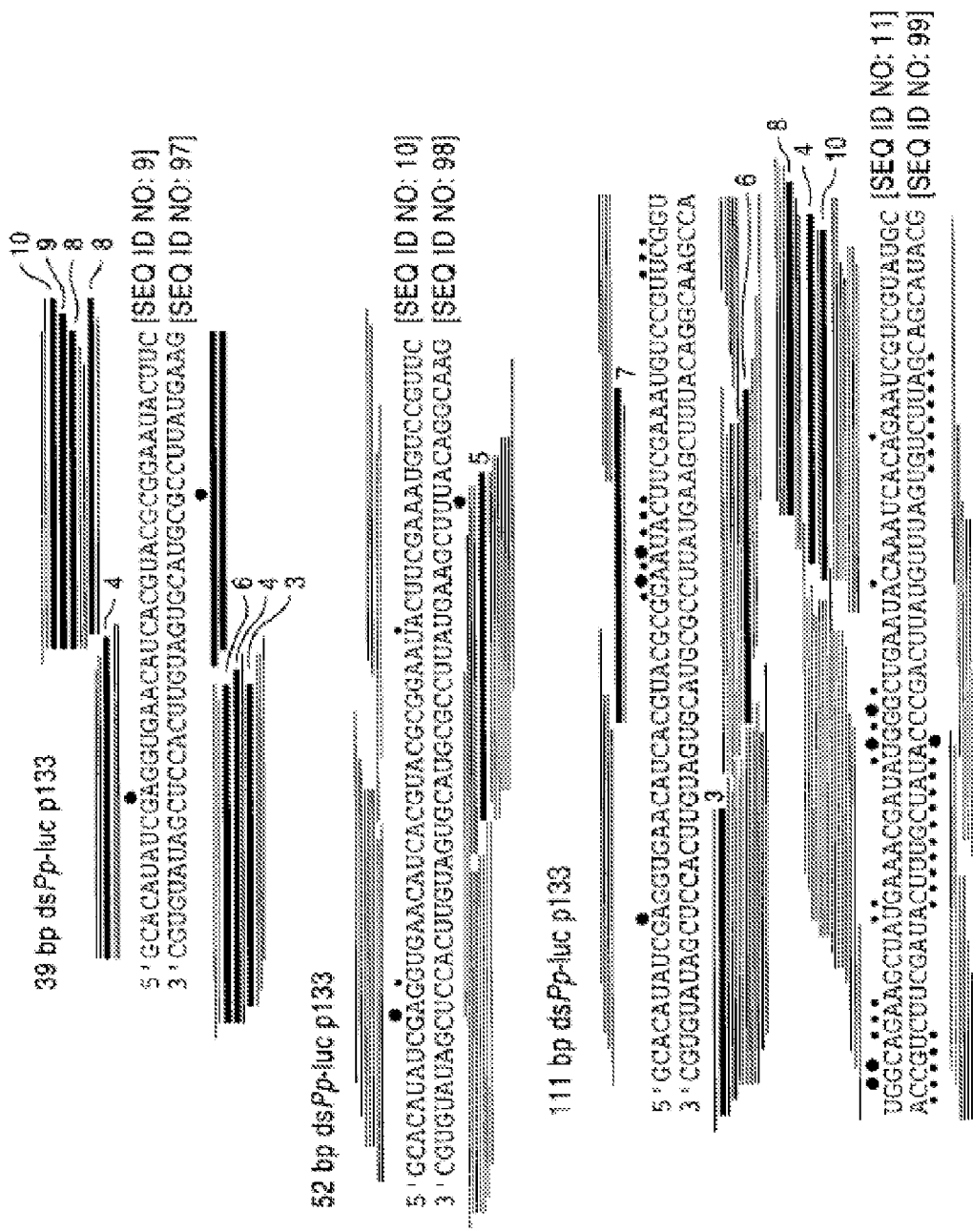
Figure 5A:
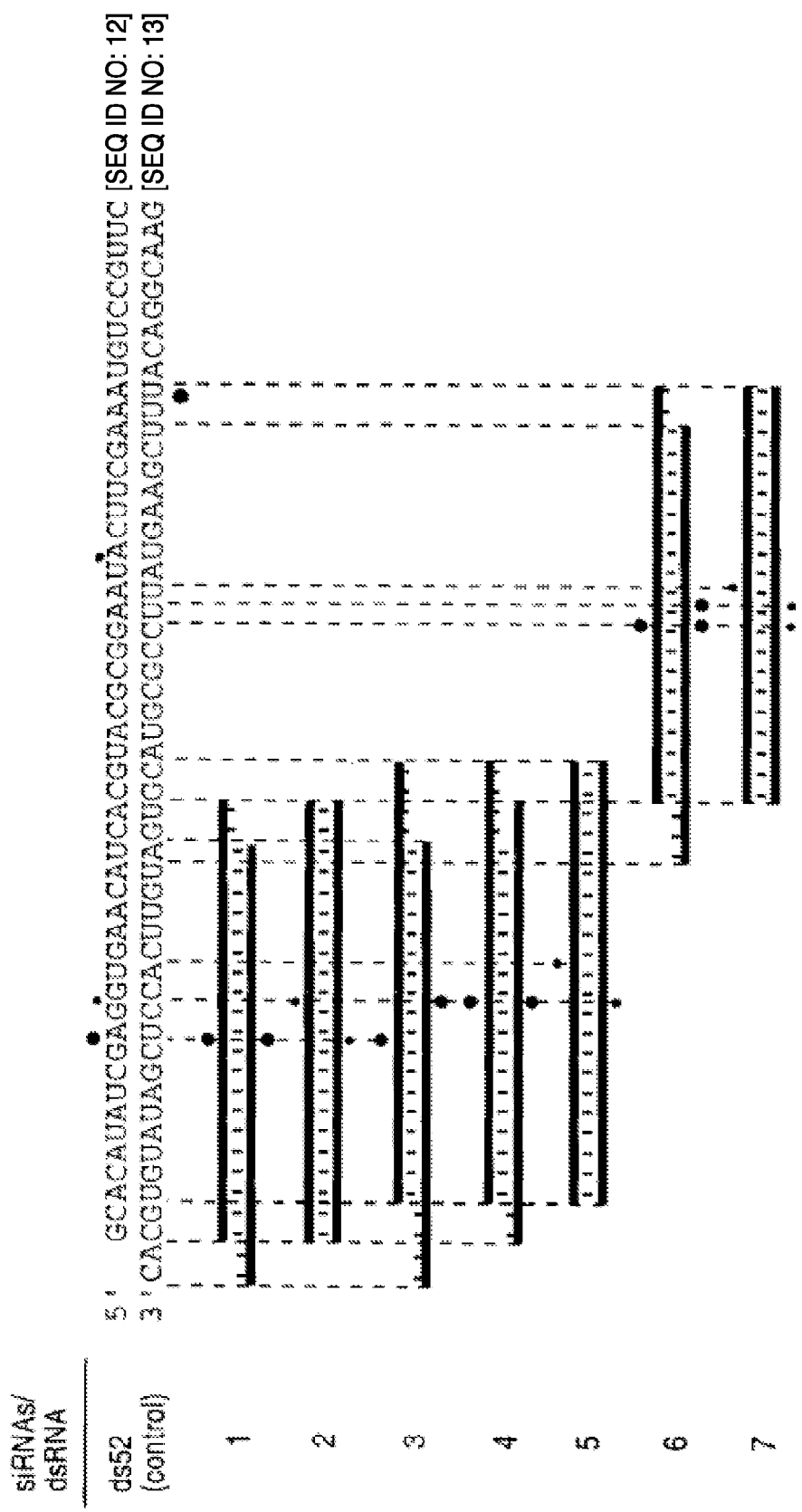
Figure 5B:
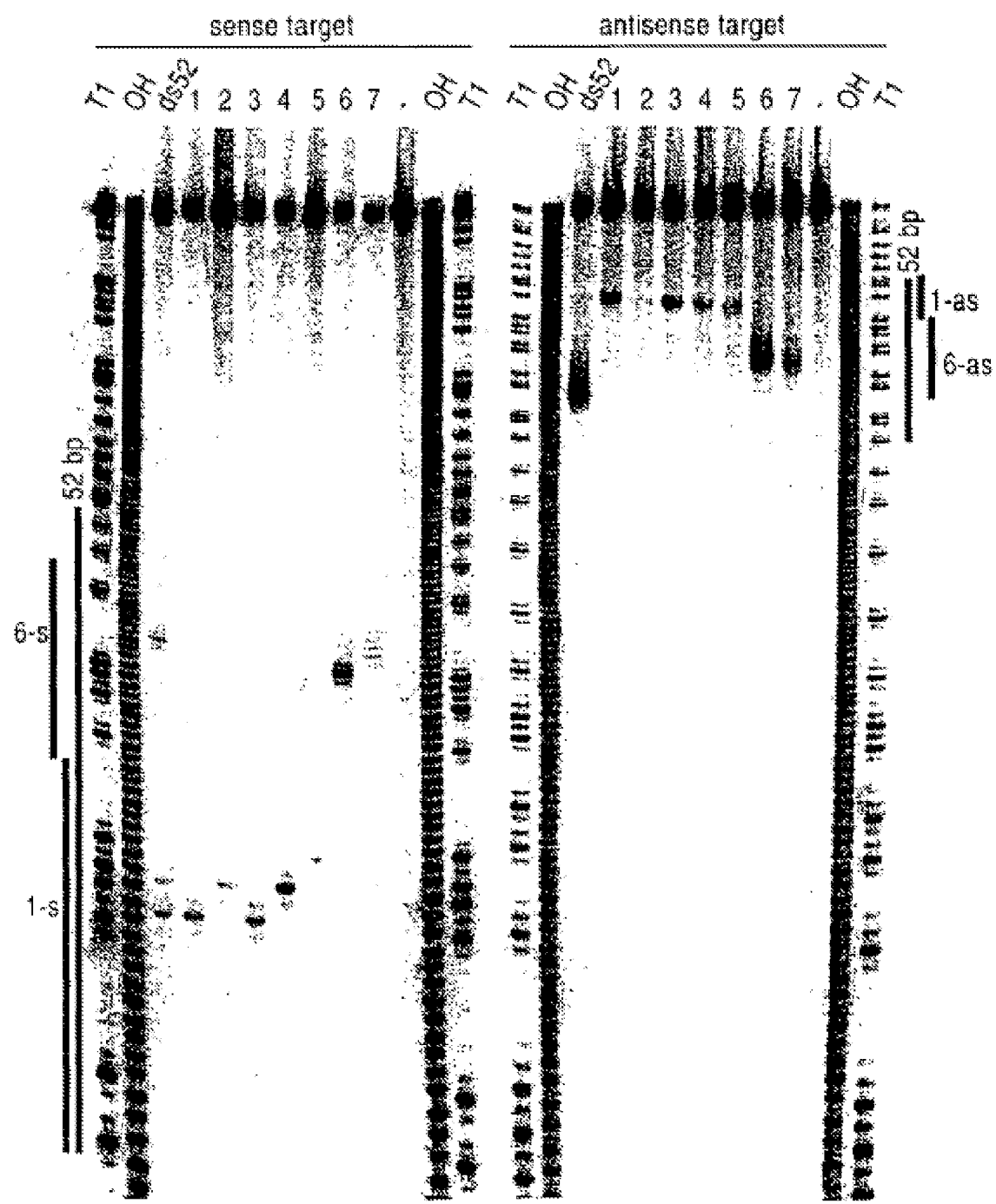

(A) Graphic representation of control 52 bp dsRNA and synthetic 21 and 22 nt dsRNAs. The sense strand of 21 and 22 nt short interfering RNAs (siRNAs) is shown blue, the antisense strand in red. The sequences of the siRNAs were derived from the cloned fragments of 52 and 111 bp dsRNAs (FIG. 4A), except for the 22 nt antisense strand of duplex 5. The siRNAs in duplex 6 and 7 were unique to the 111 bp dsRNA processing reaction. The two 3' overhanging nucleotides indicated in green are present in the sequence of the synthetic antisense strand of duplexes 1 and 3. Both strands of the control 52 bp dsRNA were prepared by in vitro transcription and a fraction of transcripts may contain untemplated 3' nucleotide addition. The target RNA cleavage sites directed by the siRNA duplexes are indicated as orange circles (see legend to FIG. 4A) and were determined as shown in FIG. 5B. (B) Position of the cleavage sites on sense and antisense target RNAs. The target RNA sequences are as described in FIG. 3B. Control 52 bp dsRNA (10 nM) or 21 and 22 nt RNA duplexes 1-7 (100 nM) were incubated with target RNA for 2.5 h at 25° C. in *Drosophila* lysate. The stable 5' cleavage products were resolved on the gel. The cleavage sites are indicated in FIG. 5A. The region targeted by the 52 bp dsRNA or the sense (s) or antisense (as) strands are indicated by the black bars to the side of the gel. The cleavage sites are all located within the region of identity of the dsRNAs. For precise determination of the cleavage sites of the antisense strand, a lower percentage gel was used.

FIG. 6: Long 3' overhangs on short dsRNAs inhibit RNAi.

(A) Graphic representation of 52 bp dsRNA constructs. The 3' extensions of sense and antisense strands are indicated in blue and red, respectively. The observed cleavage sites on the target RNAs are represented as orange circles analogous to FIG. 4A and were determined as shown in FIG. 6B. (B) Position of the cleavage sites on sense and antisense target RNAs. The target RNA sequences are as described in FIG. 3B. DsRNA (10 nM) was incubated with target RNA for 2.5 h at 25° C. in *Drosophila* lysate. The stable 5' cleavage products were resolved on the gel. The major cleavage sites are indicated with a horizontal arrow and also represented in FIG. 6A. The region targeted by the 52 bp dsRNA is represented as a black bar at both sides of the gel.

Figure 7:
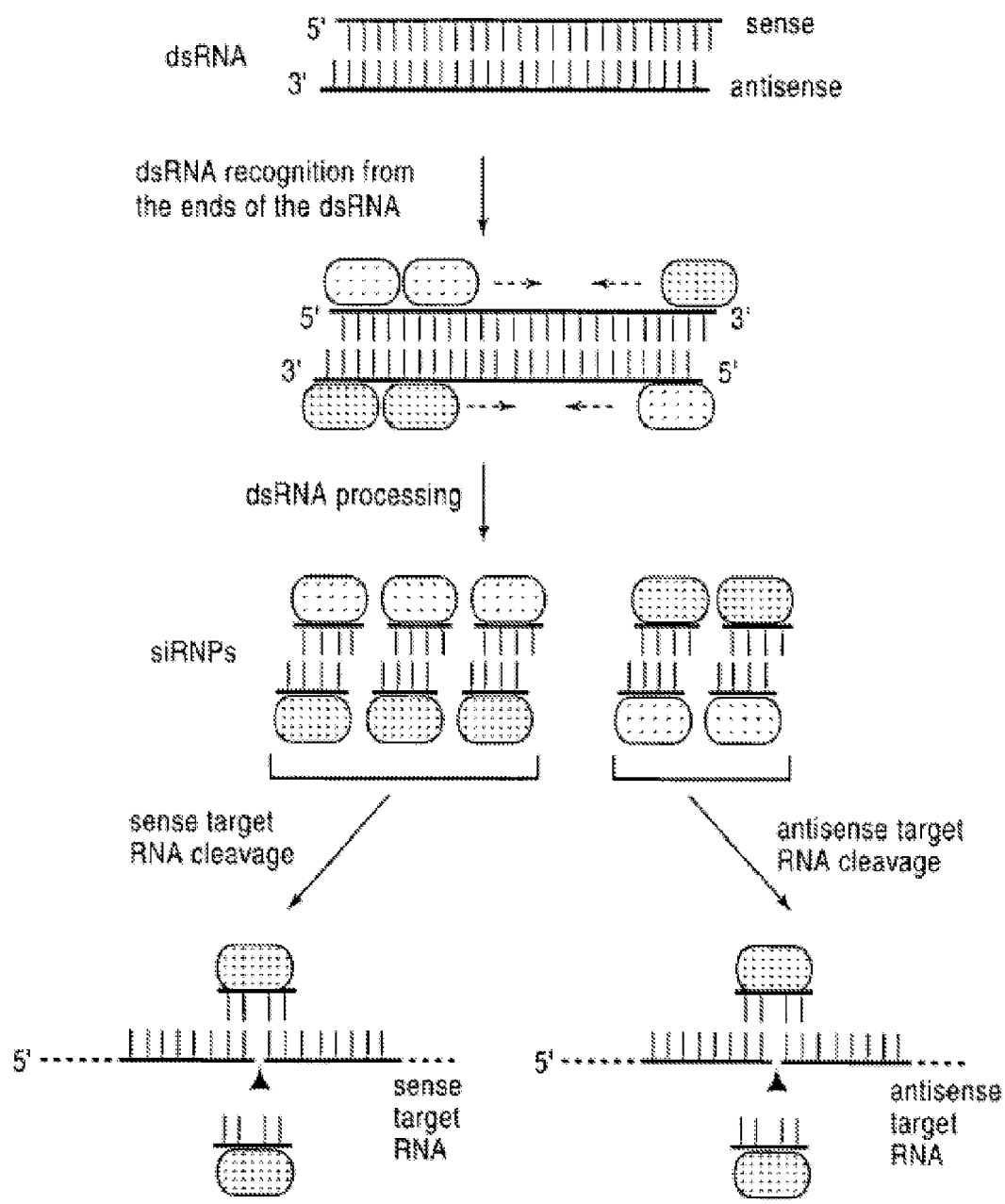

FIG. 7: Proposed Model for RNAi.

RNAi is predicted to begin with processing of dsRNA (sense strand in black, antisense strand in red) to predominantly 21 and 22 nt short interfering RNAs (siRNAs). Short overhanging 3' nucleotides, if present on the dsRNA, may be beneficial for processing of short dsRNAs. The dsRNA-processing proteins, which remain to be characterized, are represented as green and blue ovals, and assembled on the dsRNA in asymmetric fashion. In our model, this is illustrated by binding of a hypothetical blue protein or protein domain with the siRNA strand in 3' to 5' direction while the hypothetical green protein or protein domain is always bound to the opposing siRNA strand. These proteins or a subset remain associated with the siRNA duplex and preserve its orientation as determined by the direction of the dsRNA processing reaction. Only the siRNA sequence associated with the blue protein is able to guide target RNA cleavage. The endonuclease complex is referred to as small interfering ribonucleoprotein complex or siRNP. It is presumed here, that the endonuclease that cleaves the dsRNA may also cleave the target RNA, probably by temporarily displacing the passive siRNA strand not used for target recognition. The target RNA is then cleaved in the center of the region recognized by the sequence-complementary guide siRNA.

FIG. 8: Reporter constructs and siRNA duplexes.

(a) The firefly (Pp-luc) and sea pansy (Rr-luc) luciferase reporter gene regions from plasmids pGL2-Control, pGL-3-Control and pRL-TK (Promega) are illustrated. SV40 regulatory elements, the HSV thymidine kinase promoter and two introns (lines) are indicated. The sequence of GL3 luciferase is 95% identical to GL2, but RL is completely unrelated to both. Luciferase expression from pGL2 is approx. 10-fold lower than from pGL3 in transfected mammalian cells. The region targeted by the siRNA duplexes is indicated as a black bar below the coding region of the luciferase genes. (b) The sense (top) and antisense (bottom) sequences of the siRNA duplexes targeting GL2, GL3 and RL luciferase are shown. The GL2 and GL3 siRNA duplexes differ by only 3 single nucleotide substitutions (boxed in gray). As unspecific control, a duplex with the inverted GL2 sequence, invGL2, was synthesized. The 2 nt 3' overhang of 2'-deoxythymidine is indicated as TT; uGL2 is similar to GL2 siRNA but contains ribo-uridine 3' overhangs.

Figure 9:
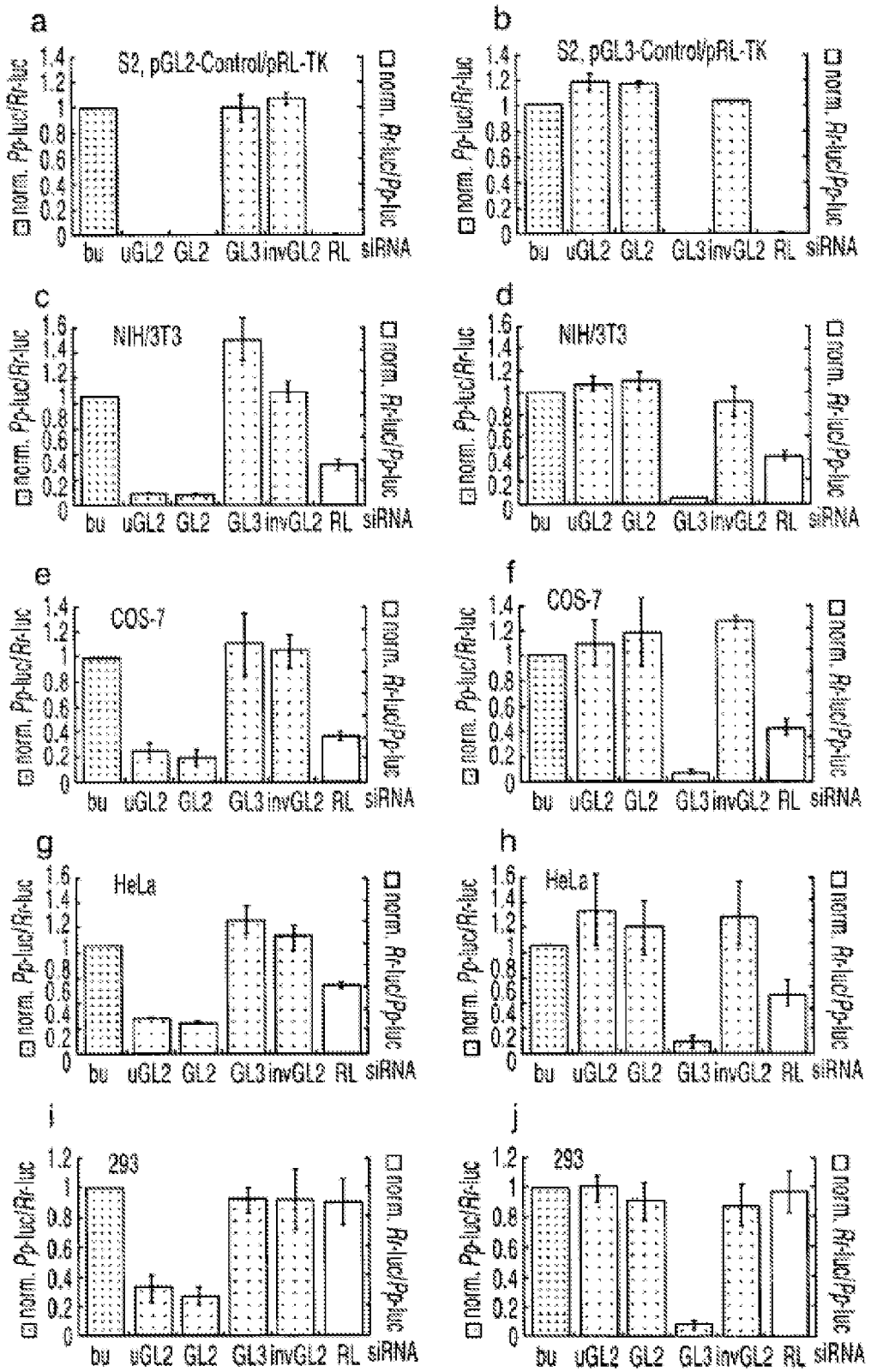

FIG. 9: RNA interference by siRNA duplexes.

Ratios of target control luciferase were normalized to a buffer control (bu, black bars); gray bars indicate ratios of *Photinus pyralis* (Pp-luc) GL2 or GL3 luciferase to *Renilla reniformis* (Rr-luc) RL luciferase (left axis), white bars indicate RL to GL2 or GL3 ratios (right axis). Panels a, c, e, g and i describe experiments performed with the combination of pGL2-Control and pRL-TK reporter plasmids, panels b, d, f, h and j with pGL3-Control and pRL-TK reporter plasmids. The cell line used for the interference experiment is indicated at the top of each plot. The ratios of Pp-luc/Rr-luc for the buffer control (bu) varied between 0.5 and 10 for pGL2/pRL and between 0.03 and 1 for pGL3/pRL, respectively, before normalization and between the various cell lines tested. The plotted data were averaged from three independent experiments±S.D.

Figure 10:
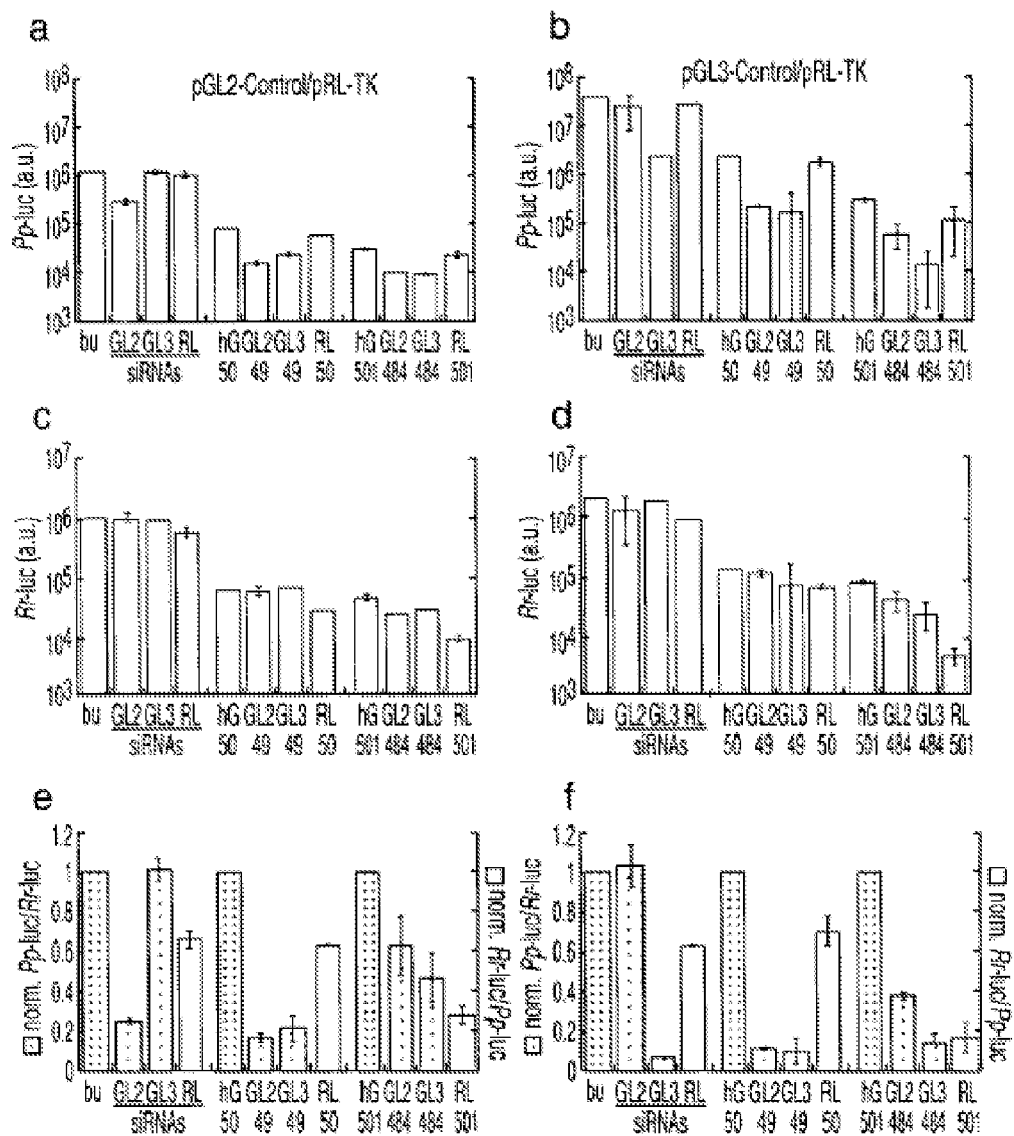

FIG. 10: Effects of 21 nt siRNA, 50 bp and 500 bp dsRNAs on luciferase expression in HeLa cells.

The exact length of the long dsRNAs is indicated below the bars. Panels a, c and e describe experiments performed with pGL2-Control and pRL-TK reporter plasmids, panels b, d and f with pGL3-Control and pRL-TK reporter plasmids. The data were averaged from two independent experiments±S.D. (a), (b) Absolute Pp-luc expression, plotted in arbitrary luminescence units. (c), (d) Rr-luc expression, plotted in arbitrary luminescence units. (e), (f) Ratios of normalized target to control luciferase. The ratios of luciferase activity for siRNA duplexes were normalized to a buffer control (bu, black bars); the luminescence ratios for 50 or 500 bp dsRNAs were normalized to the respective ratios observed for 50 and 500 bp dsRNA from humanized GFP (hG, black bars). It should be noted that the overall differences in sequences between the 49 and 484 bp dsRNAs targeting GL2 and GL3 are not sufficient to confer specificity between GL2 and GL3 targets (43 nt uninterrupted identity in 49 bp segment, 239 nt longest uninterrupted identity in 484 bp segment).

FIG. 11 Parts I-III: Variation of the 3' overhang of duplexes of 21-nt siRNAs.

Part I (A) Outline of the experimental strategy. The capped and polyadenylated sense target mRNA is depicted and the relative positions of sense and antisense siRNAs are shown. Eight series of duplexes, according to the eight different antisense strands were prepared. The siRNA sequences and the number of overhanging nucleotides were changed in 1-nt steps. Part I (B) Normalized relative luminescence of target luciferase (*Photinus pyralis*, Pp-luc) to control luciferase (*Renilla reniformis*, Rr-luc) in *D. melanogaster* embryo lysate in the presence of 5 nM blunt-ended dsRNAs. The luminescence ratios determined in the presence of dsRNA were normalized to the ratio obtained for a buffer control (bu, black bar). Normalized ratios less than 1 indicate specific interference. Part I (C-D), Part II (E-G), Part III (H-J) Normalized interference ratios for eight series of 21-nt siRNA duplexes. The sequences of siRNA duplexes are depicted above the bar graphs. Each panel shows the interference ratio for a set of duplexes formed with a given antisense guide siRNA and 5 different sense siRNAs. The number of overhanging nucleotides (3' overhang, positive numbers; 5' overhangs, negative numbers) is indicated on the x-axis. Data points were averaged from at least 3 independent experiments, error bars represent standard deviations.

FIG. 12: Variation of the length of the sense strand of siRNA duplexes.

Part I (A) Graphic representation of the experiment. Three 21-nt antisense strands were paired with eight sense siRNAs. The siRNAs were changed in length at their 3' end. The 3' overhang of the antisense siRNA was 1-nt Part I (B), 2-nt Part II (C), or 3-nt Part II (D) while the sense siRNA overhang was varied for each series. The sequences of the siRNA duplexes and the corresponding interference ratios are indicated.

Figure 13:
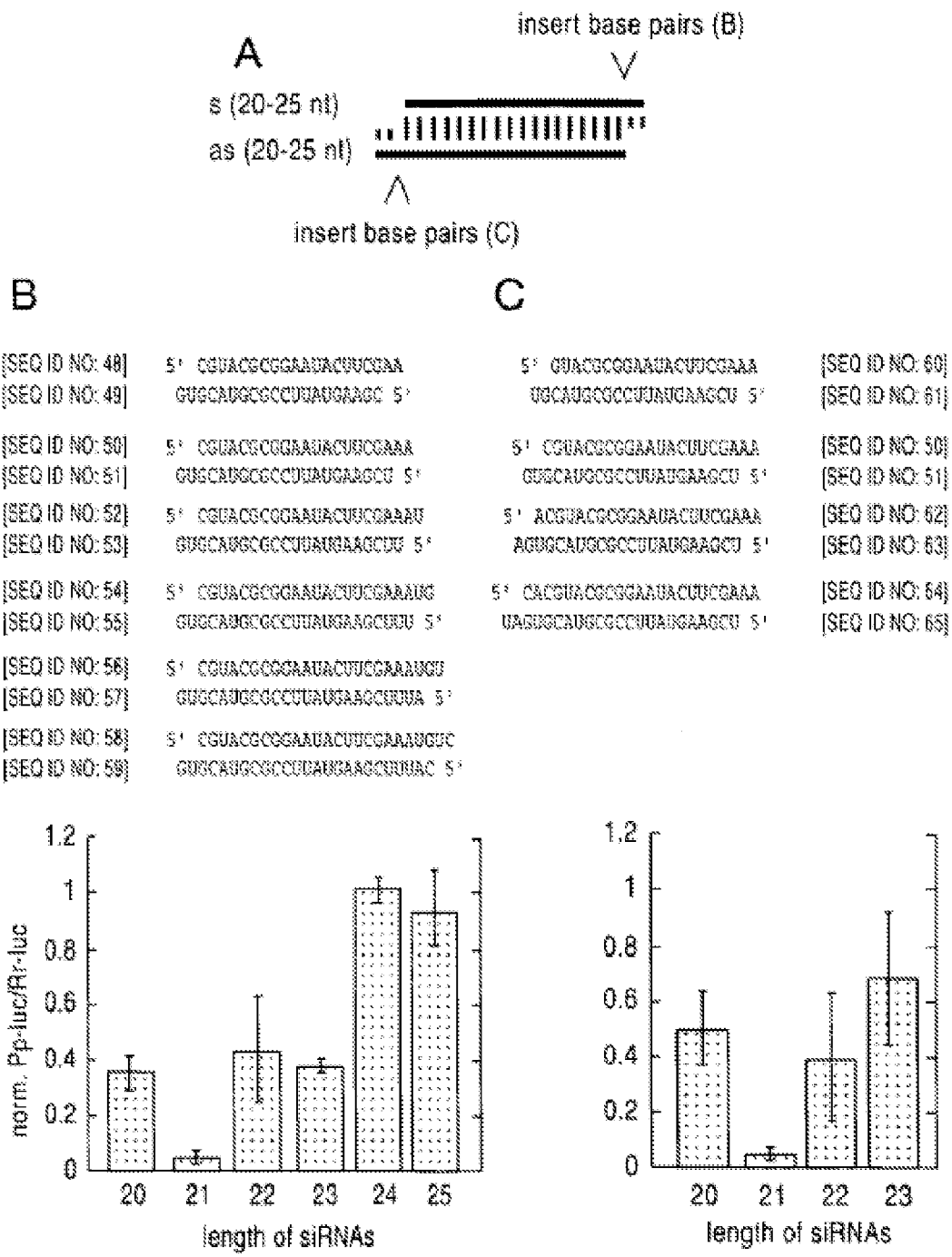

FIG. 13: Variation of the length of siRNA duplexes with preserved 2-nt 3' overhangs.

(A) Graphic representation of the experiment. The 21-nt siRNA duplex is identical in sequence to the one shown in FIG. 11 Part III H or 12 Part II C. The siRNA duplexes were extended to the 3' side of the sense siRNA (B) or the 5' side of the sense siRNA (C). The siRNA duplex sequences and the respective interference ratios are indicated.

Figure 14:
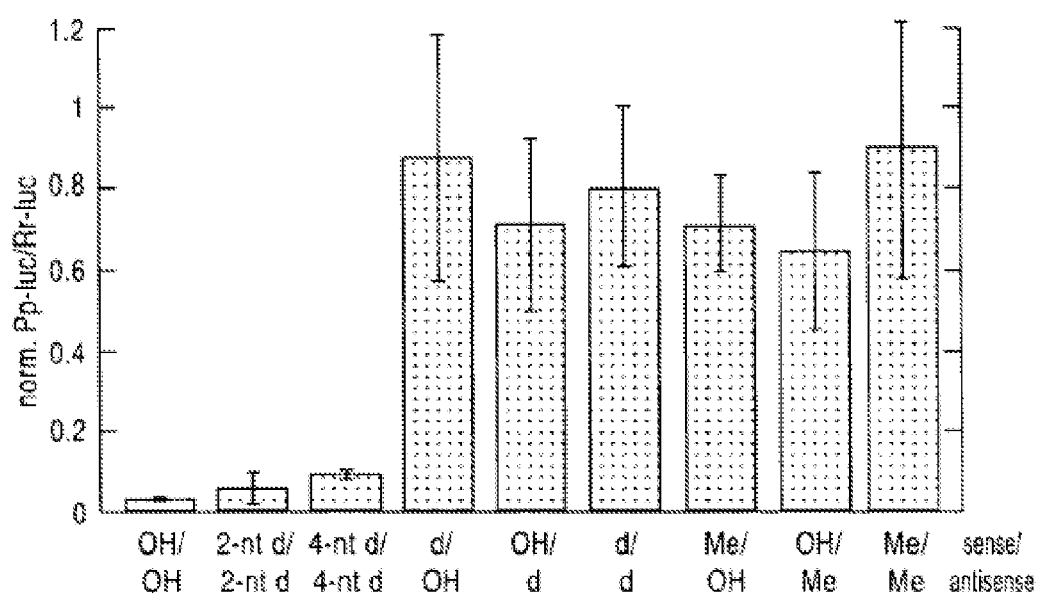

FIG. 14: Substitution of the 2'-hydroxyl groups of the siRNA ribose residues.

The 2'-hydroxyl groups (OH) in the strands of siRNA duplexes were replaced by 2'-deoxy (d) or 2'-O-methyl (Me). 2-nt and 4-nt 2'-deoxy substitutions at the 3'-ends are indicated as 2-nt d and 4-nt d, respectively. Uridine residues were replaced by 2'-deoxy thymidine.

FIG. 15: Mapping of sense and antisense target RNA cleavage by 21-nt siRNA duplexes with 2-nt 3' overhangs.

(A) Graphic representation of $^{32}$P-(asterisk) cap-labelled sense and antisense target RNAs and siRNA duplexes. The position of sense and antisense target RNA cleavage is indicated by triangles on top and below the siRNA duplexes, respectively. (B) Mapping of target RNA cleavage sites. After 2 h incubation of 10 nM target with 100 nM siRNA duplex in *D. melanogaster* embryo lysate, the 5' cap-labelled substrate and the 5' cleavage products were resolved on sequencing gels. Length markers were generated by partial RNase T1 digestion (T1) and partial alkaline hydrolysis (OH—) of the target RNAs. The bold lines to the left of the images indicate the region covered by the siRNA strands 1 and 5 of the same orientation as the target.

Figure 16:
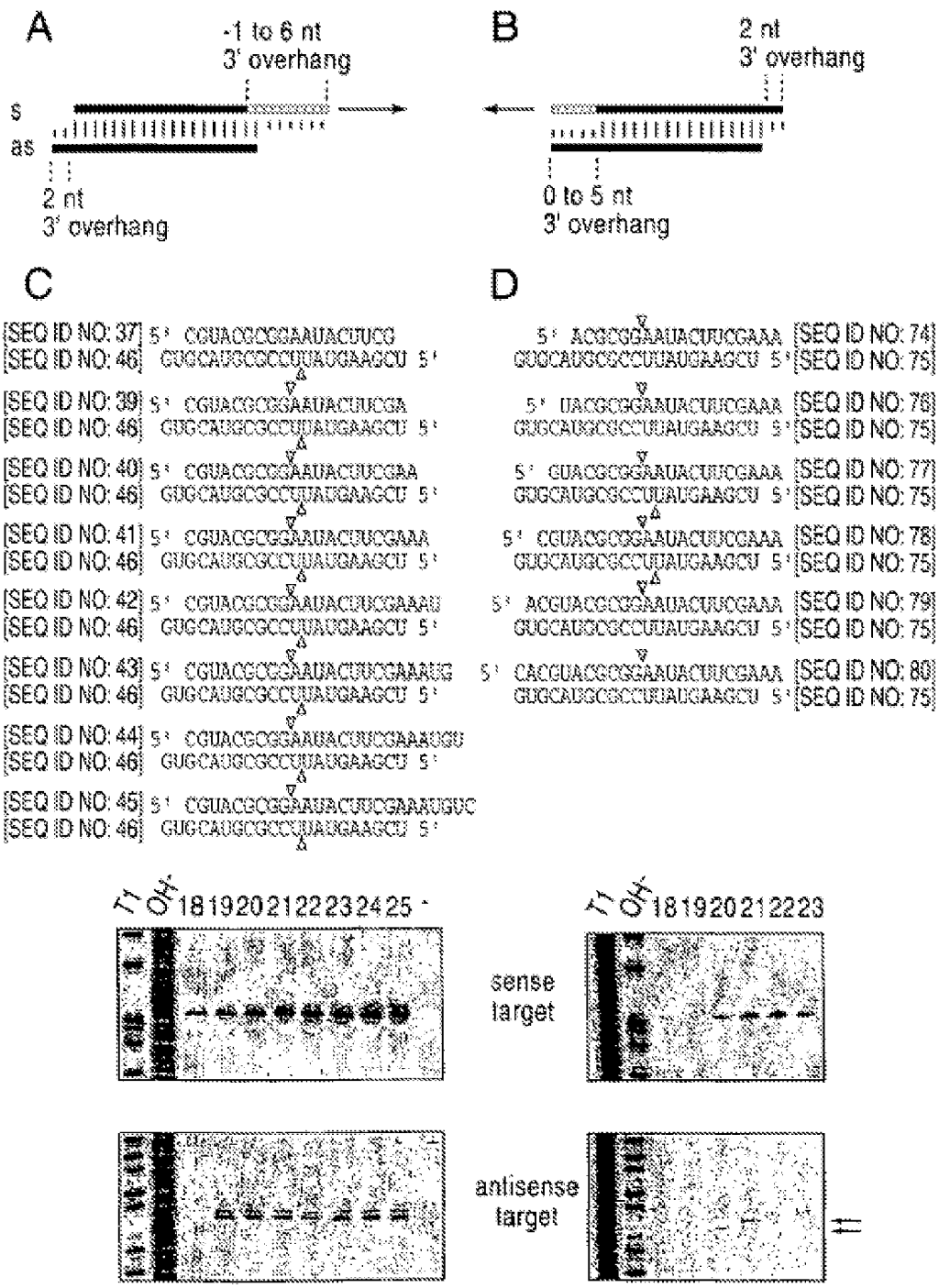

FIG. 16: The 5' end of a guide siRNA defines the position of target RNA cleavage. (A, B) Graphic representation of the experimental strategy. The antisense siRNA was the same in all siRNA duplexes, but the sense strand was varied between 18 to 25 nt by changing the 3' end (A) or 18 to 23 nt by changing the 5' end (B). The position of sense and antisense target RNA cleavage is indicated by triangles on top and below the siRNA duplexes, respectively. (C, D) Analysis of target RNA cleavage using cap-labelled sense (top panel) or antisense (bottom panel) target RNAs. Only the cap-labelled 5' cleavage products are shown. The sequences of the siRNA duplexes are indicated, and the length of the sense siRNA strands is marked on top of the panel. The control lane marked with a dash in (C) shows target RNA incubated in absence of siRNAs. Markers were as described in FIG. 15. The arrows in (D), bottom panel, indicate the target RNA cleavage sites that differ by 1 nt.

Figure 17:
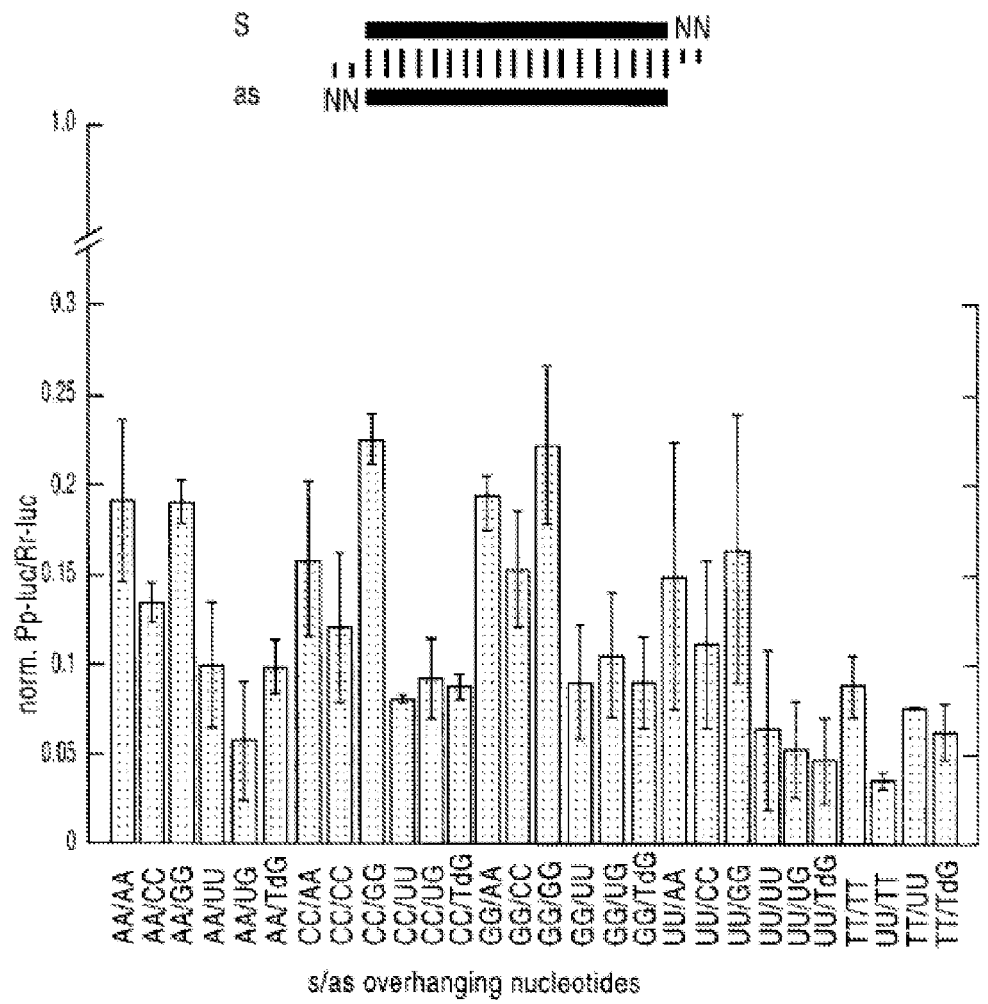

FIG. 17: Sequence variation of the 3' overhang of siRNA duplexes.

The 2-nt 3' overhang (NN, in gray) was changed in sequence and composition as indicated (T, 2'-deoxythymidine, dG, 2'-deoxyguanosine; asterisk, wild-type siRNA duplex). Normalized interference ratios were determined as described in FIG. 11 Parts I-III. The wild-type sequence is the same as depicted in FIG. 14.

Figure 18:
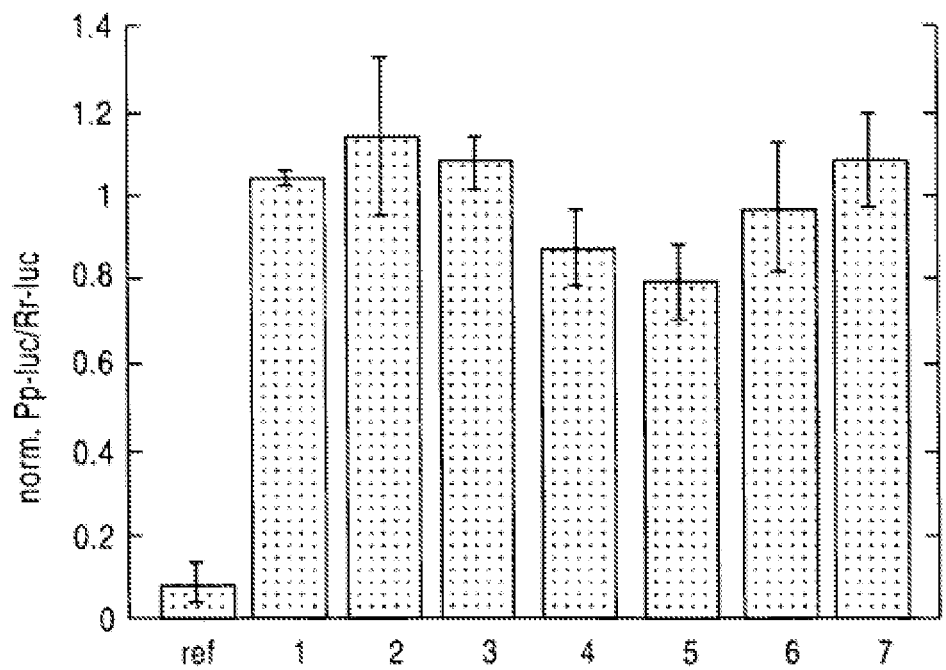

FIG. 18: Sequence specificity of target recognition.

The sequences of the mismatched siRNA duplexes are shown, modified sequence segments or single nucleotides are underlayed in gray. The reference duplex (ref) and the siRNA duplexes 1 to 7 contain 2'-deoxythymidine 2-nt overhangs. The silencing efficiency of the thymidine-modified reference duplex was comparable to the wild-type sequence (FIG. 17). Normalized interference ratios were determined as described in FIG. 11 Parts I-III.

Figure 19:
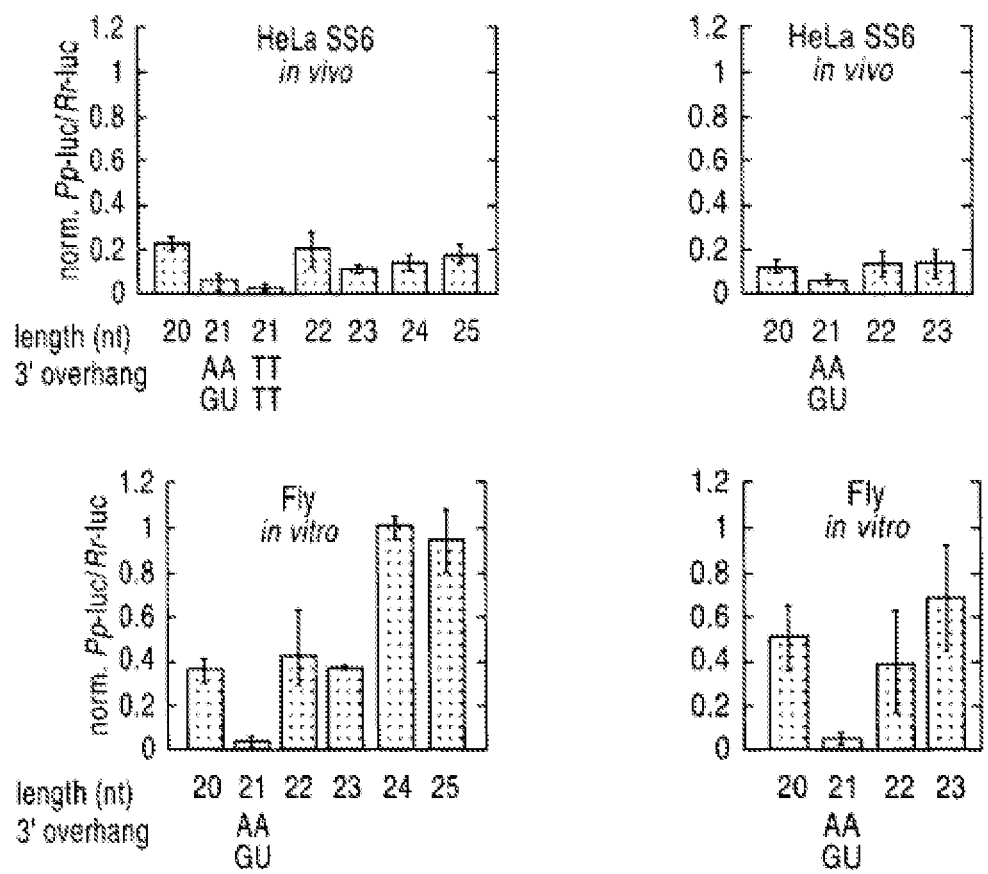

FIG. 19: Variation of the length of siRNA duplexes with preserved 2-nt 3' overhangs. The siRNA duplexes were extended to the 3' side of the sense siRNA (A) or the 5' side of the sense siRNA (B). The siRNA duplex sequences and the respective interference ratios are indicated. For HeLa SS6 cells, siRNA duplexes (0.84 µg) targeting GL2 luciferase were transfected together with pGL2-Control and pRL-TK plasmids. For comparison, the in vitro RNAi activities of siRNA duplexes tested in *D. melanogaster* lysate are indicated.

EXAMPLE 1

RNA Interference Mediated by Small Synthetic RNAs 1.1. Experimental Procedures
1.1.1 In Vitro RNAi In vitro RNAi and lysate preparations were performed as described previously (Tuschl et al., 1999; Zamore et al., 2000). It is critical to use freshly dissolved creatine kinase (Roche) for optimal ATP regeneration. The RNAi translation assays (FIG. 1) were performed with dsRNA concentrations of 5 nM and an extended pre-incubation period of 15 min at 25° C. prior to the addition of in vitro transcribed, capped and polyadenylated Pp-luc and Rr-luc reporter mRNAs. The incubation was continued for 1 h and the relative amount of Pp-luc and Rr-luc protein was analyzed using the dual luciferase assay (Promega) and a Monolight 3010C luminometer (PharMingen).

1.1.2 RNA Synthesis

Standard procedures were used for in vitro transcription of RNA from PCR templates carrying T7 or SP6 promoter sequences, see for example (Tuschl et al., 1998). Synthetic RNA was prepared using Expedite RNA phosphoramidites (Proligo). The 3' adapter oligonucleotide was synthesized using dimethoxytrityl-1,4-benzenedimethanol-succinyl-aminopropyl-CPG. The oligoribonucleotides were deprotected in 3 ml of 32% ammonia/ethanol (3/1) for 4 h at 55° C. (Expedite RNA) or 16 h at 55° C. (3' and 5' adapter DNA/RNA chimeric oligonucleotides) and then desilylated and gel-purified as described previously (Tuschl et al., 1993). RNA transcripts for dsRNA preparation including long 3' overhangs were generated from PCR templates that contained a T7 promoter in sense and an SP6 promoter in antisense direction. The transcription template for sense and antisense target RNA was PCR-amplified with GCGTAATACGACTCACTATAGAACAAT-TGCTTTTACAG (bold, T7 promoter) [SEQ ID NO:1] as 5' primer and ATTTAGGTGACACTATAGGCATAAA-GAATTGAAGA (bold, SP6 promoter) [SEQ ID NO:2] as 3' primer and the linearized Pp-luc plasmid (pGEM-luc sequence) (Tuschl et al., 1999) as template; the T7-transcribed sense RNA was 177 nt long with the Pp-luc sequence between pos. 113-273 relative to the start codon and followed by 17 nt of the complement of the SP6 promoter sequence at the 3' end. Transcripts for blunt-ended dsRNA formation were prepared by transcription from two different PCR products which only contained a single promoter sequence.

dsRNA annealing was carried out using a phenol/chloroform extraction. Equimolar concentration of sense and antisense RNA (50 nM to 10 µM, depending on the length and amount available) in 0.3 M, NaOAc (pH 6) were incubated for 30 s at 90° C. and then extracted at room temperature with an equal volume of phenol/chloroform, and followed by a chloroform extraction to remove residual phenol. The resulting dsRNA was precipitated by addition of 2.5-3 volumes of ethanol. The pellet was dissolved in lysis buffer (100 mM KCl, 30 mM HEPES-KOH, pH 7.4, 2 mM Mg(OAc)$_2$) and the quality of the dsRNA was verified by standard agarose gel electrophoreses in 1×TAE-buffer. The 52 bp dsRNA with the 17 nt and 20 nt 3' overhangs (FIG. 6) were annealed by incubating for 1 min at 95° C., then rapidly cooled to 70° C. and followed by slow cooling to room temperature over a 3 h period (50 µl annealing reaction, 1 µM strand concentration, 300 mM NaCl, 10 mM Tris-HCl, pH 7.5). The dsRNAs were then phenol/chloroform extracted, ethanol-precipitated and dissolved in lysis buffer.

Transcription of internally $^{32}$P-radiolabeled RNA used for dsRNA preparation (FIGS. 2 and 4) was performed using 1 mM ATP, CTP, GTP, 0.1 or 0.2 mM UTP, and 0.2-0.3 µM-$^{32}$P-UTP (3000 Ci/mmol), or the respective ratio for radiolabeled nucleoside triphosphates other than UTP. Labeling of the cap of the target RNAs was performed as described previously. The target RNAs were gel-purified after cap-labeling.

1.1.3 Cleavage Site Mapping

Standard RNAi reactions were performed by pre-incubating 10 nM dsRNA for 15 min followed by addition of 10 nM cap-labeled target RNA. The reaction was stopped after a further 2 h (FIG. 2A) or 2.5 h incubation (FIGS. 5B and 6B) by proteinase K treatment (Tuschl et al., 1999). The samples were then analyzed on 8 or 10% sequencing gels. The 21 and 22 nt synthetic RNA duplexes were used at 100 nM final concentration (FIG. 5B).

1.1.4 Cloning of ~21 nt RNAs

The 21 nt RNAs were produced by incubation of radiolabeled dsRNA in Drosophila lysate in absence of target RNA (200 Fl reaction, 1 h incubation, 50 nM dsP111, or 100 nM dsP52 or dsP39). The reaction mixture was subsequently treated with proteinase K (Tuschl et al., 1999) and the dsRNA-processing products were separated on a denaturing 15% polyacrylamide gel. A band, including a size range of at least 18 to 24 nt, was excised, eluted into 0.3 M NaCl overnight at 4° C. and in siliconized tubes. The RNA was recovered by ethanol-precipitation and dephosphorylated (30 Fl reaction, 30 min, 50° C., 10 U alkaline phosphatase, Roche). The reaction was stopped by phenol/chloroform extraction and the RNA was ethanol-precipitated. The 3' adapter oligonucleotide (pUUUaaccgcatccttctcx: uppercase, RNA; lowercase, DNA; p, phosphate; x, 4-hydroxymethylbenzyl) [SEQ ID NO: 100] was then ligated to the dephosphorylated ~21 nt RNA (20 Fl reaction, 30 min, 37° C., 5 FM 3' adapter, 50 mM Tris-HCl, pH 7.6, 10 mM MgCl$_2$, 0.2 mM ATP, 0.1 mg/ml acetylated BSA, 15% DMSO, 25 U T4 RNA ligase, Amersham-Pharmacia) (Pan and Uhlenbeck, 1992). The ligation reaction was stopped by the addition of an equal volume of 8 M urea/50 mM EDTA stop mix and directly loaded on a 15% gel. Ligation yields were greater 50%. The ligation product was recovered from the gel and 5'-phosphorylated (20 Fl reaction, 30 min, 37° C., 2 mM ATP, 5 U T4 polynucleotide kinase, NEB). The phosphorylation reaction was stopped by phenol/chloroform extraction and RNA was recovered by ethanol-precipitation. Next, the 5' adapter (tactaatacgactcactAAA: uppercase, RNA; lowercase, DNA) [SEQ ID NO: 101] was ligated to the phosphorylated ligation product as described above. The new ligation product was gel-purified and eluted from the gel slice in the presence of reverse transcription primer (GACTAGCTGGAATTCAAGGATGCG-GTTAAA: bold, Eco RI site) [SEQ ID NO: 3] used as carrier. Reverse transcription (15 Fl reaction, 30 min, 42° C., 150 U Superscript II reverse transcriptase, Life Technologies) was followed by PCR using as 5' primer CAGCCAACGGAAT-TCATACGACTCACTAAA (bold, Eco RI site) [SEQ ID NO: 4] and the 3' RT primer. The PCR product was purified by phenol/chloroform extraction and ethanol-precipitated. The PCR product was then digested with Eco RI (NEB) and concatamerized using T4 DNA ligase (high conc., NEB). Concatamers of a size range of 200 to 800 bp were separated on a low-melt agarose gel, recovered from the gel by a standard melting and phenol extraction procedure, and ethanol-precipitated. The unpaired ends were filled in by incubation with Taq polymerase under standard conditions for 15 min at 72° C. and the DNA product was directly ligated into the pCR2.1-TOPO vector using the TOPO TA cloning kit (Invitrogen). Colonies were screened using PCR and M13-20 and M13 Reverse sequencing primers. PCR products were directly submitted for custom sequencing (Sequence Laboratories Göttingen GmbH, Germany). On average, four to five 21 mer sequences were obtained per clone.

1.1.5 2D-TLC Analysis

Nuclease PI digestion of radiolabeled, gel-purified siRNAs and 2D-TLC was carried out as described (Zamore et al., 2000). Nuclease T2 digestion was performed in 10 µl reactions for 3 h at 50° C. in 10 mM ammonium acetate (pH 4.5) using 2 µg/µl carrier tRNA and 30 U ribonuclease T2 (Life Technologies). The migration of non-radioactive standards was determined by UV shadowing. The identity of nucleoside-3',5'-disphosphates was confirmed by co-migration of the T2 digestion products with standards prepared by 5'-$^{32}$P-phosphorylation of commercial nucleoside 3'-monophosphates using γ-$^{32}$P-ATP and T4 polynucleotide kinase (data not shown).

Figure 1B:
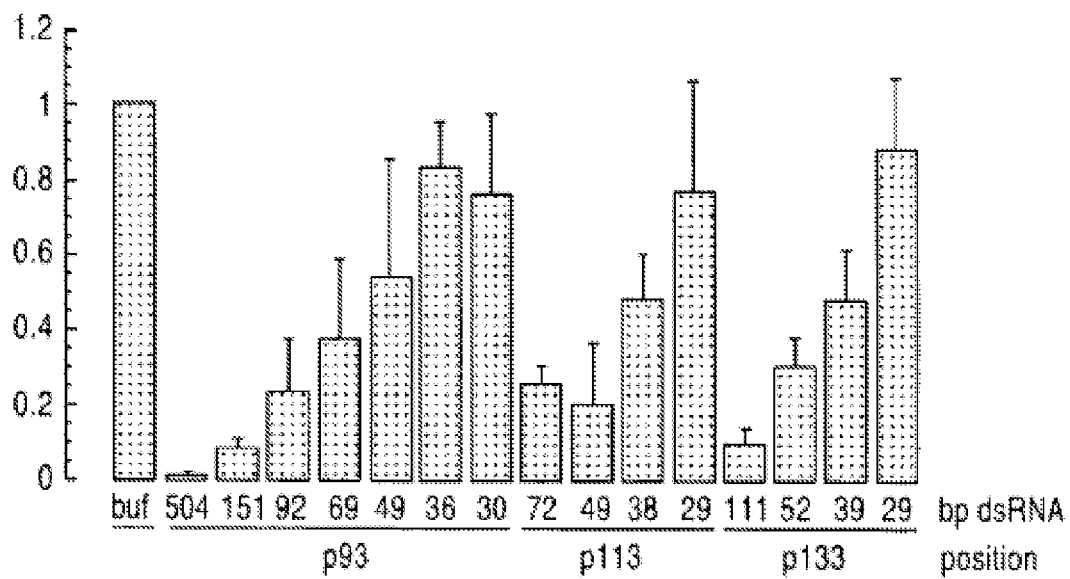

1.2 Results and Discussion 1.2.1 Length Requirements for Processing of dsRNA to 21 and 22 nt RNA Fragments Lysate prepared from D. melanogaster syncytial embryos recapitulates RNAi in vitro providing a novel tool for biochemical analysis of the mechanism of RNAi (Tuschl et al., 1999; Zamore et al., 2000). In vitro and in vivo analysis of the length requirements of dsRNA for RNAi has revealed that short dsRNA (<150 bp) are less effective than longer dsRNAs in degrading target mRNA (Caplen et al., 2000; Hammond et al., 2000; Ngo et al., 1998; Tuschl et al., 1999). The reasons for reduction in mRNA degrading efficiency are not understood. We therefore examined the precise length requirement of dsRNA for target RNA degradation under optimized conditions in the *Drosophila* lysate (Zamore et al., 2000). Several series of dsRNAs were synthesized and directed against firefly luciferase (Pp-luc) reporter RNA. The specific suppression of target RNA expression was monitored by the dual luciferase assay (Tuschl et al., 1999) (FIGS. 1A and 1B). We detected specific inhibition of target RNA expression for dsRNAs as short as 38 bp, but dsRNAs of 29 to 36 bp were not effective in this process. The effect was independent of the target position and the degree of inhibition of Pp-luc mRNA expression correlated with the length of the dsRNA, i.e. long dsRNAs were more effective than short dsRNAs.

It has been suggested that the 21-23 nt RNA fragments generated by processing of dsRNAs are the mediators of RNA interference and co-suppression (Hamilton and Baulcombe, 1999; Hammond et al., 2000; Zamore et al., 2000). We therefore analyzed the rate of 21-23 nt fragment formation for a subset of dsRNAs ranging in size between 501 to 29 bp. Formation of 21-23 nt fragments in *Drosophila* lysate (FIG. 2) was readily detectable for 39 to 501 bp long dsRNAs but was significantly delayed for the 29 bp dsRNA. This observation is consistent with a role of 21-23 nt fragments in guiding mRNA cleavage and provides an explanation for the lack of RNAi by 30 bp dsRNAs. The length dependence of 21-23 mer formation is likely to reflect a biologically relevant control mechanism to prevent the undesired activation of RNAi by short intramolecular base-paired structures of regular cellular RNAs.

1.2.2 39 bp dsRNA Mediates Target RNA Cleavage at a Single Site

Addition of dsRNA and 5'-capped target RNA to the *Drosophila* lysate results in sequence-specific degradation of the target RNA (Tuschl et al., 1999). The target mRNA is only cleaved within the region of identity with the dsRNA and many of the target cleavage sites were separated by 21-23 nt (Zamore et al., 2000). Thus, the number of cleavage sites for a given dsRNA was expected to roughly correspond to the length of the dsRNA divided by 21. We mapped the target cleavage sites on a sense and an antisense target RNA which was 5' radiolabeled at the cap (Zamore et al., 2000) (FIGS. 3 and 3B). Stable 5' cleavage products were separated on a sequencing gel and the position of cleavage was determined by comparison with a partial RNase TI and an alkaline hydrolysis ladder from the target RNA.

Consistent with the previous observation (Zamore et al., 2000), all target RNA cleavage sites were located within the region of identity to the dsRNA. The sense or the antisense target was only cleaved once by 39 bp dsRNA. Each cleavage site was located 10 nt from the 5' end of the region covered by the dsRNA (FIG. 3B). The 52 bp dsRNA, which shares the same 5' end with the 39 bp dsRNA, produces the same cleavage site on the sense target, located 10 nt from the 5' end of the region of identity with the dsRNA, in addition to two weaker cleavage sites 23 and 24 nt downstream of the first site. The antisense target was only cleaved once, again 10 nt from the 5' end of the region covered by its respective dsRNA. Mapping of the cleavage sites for the 38 to 49 bp dsRNA shown in FIG. 1 showed that the first and predominant cleavage site was always located 7 to 10 nt downstream of the region covered by the dsRNA (data not shown). This suggests that the point of target RNA cleavage is determined by the end of the dsRNA and could imply that processing to 21-23 mers, starts from the ends of the duplex.

Figure 3A:
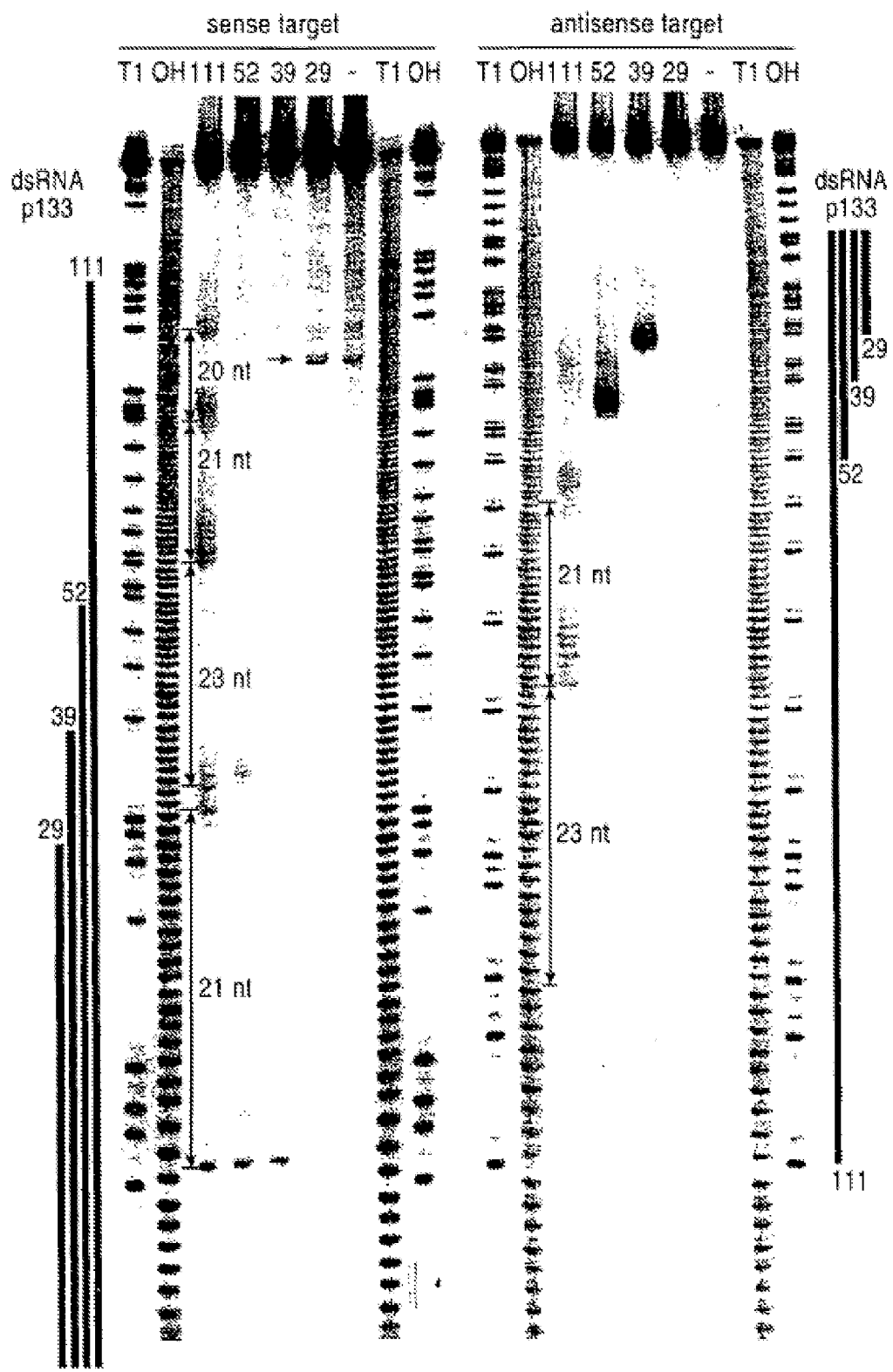
Figure 3B:
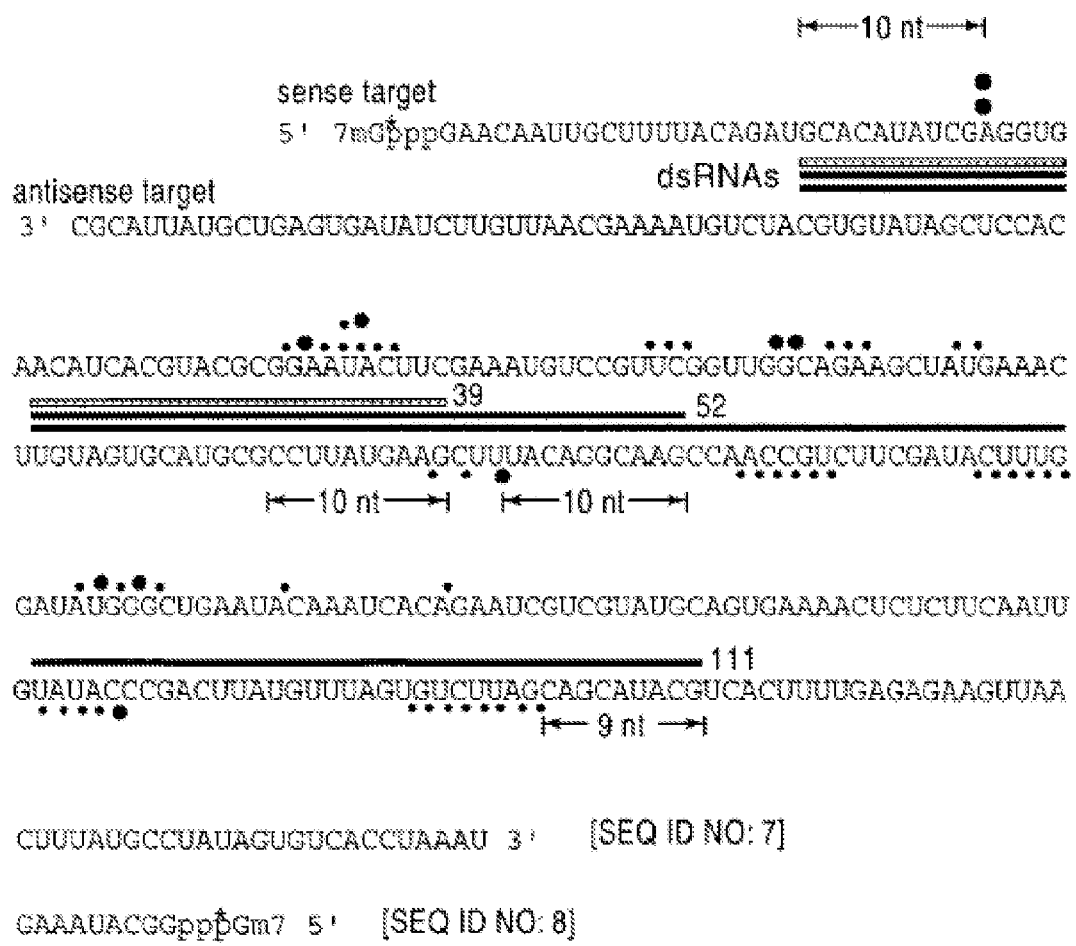

Cleavage sites on sense and antisense target for the longer 111 bp dsRNA were much more frequent than anticipated and most of them appear in clusters separated by 20 to 23 nt (FIGS. 3A and 3B). As for the shorter dsRNAs, the first cleavage site on the sense-target is 10 nt from the 5' end of the region spanned by the dsRNA, and the first cleavage site on the antisense target is located 9 nt from the 5' end of the region covered by the dsRNA. It is unclear what causes this disordered cleavage, but one possibility could be that longer dsRNAs may not only get processed from the ends but also internally, or there are some specificity determinants for dsRNA processing which we do not yet understand. Some irregularities to the 21-23 nt spacing were also previously noted (Zamore et al., 2000). To better understand the molecular basis of dsRNA processing and target RNA recognition, we decided to analyze the sequences of the 21-23 nt fragments generated by processing of 39, 52, and 111 bp dsRNAs in the *Drosophila* lysate.

1.2.3. dsRNA is Processed to 21 and 22 nt RNAs by an RNase III-Like Mechanism

In order to characterize the 21-23 nt RNA fragments we examined the 5' and 3' termini of the RNA fragments. Periodate oxidation of gel-purified 21-23 nt RNAs followed by β-elimination indicated the presence of a terminal 2' and 3' hydroxyl groups. The 21-23 mers were also responsive to alkaline phosphatase treatment indicating the presence of a 5' terminal phosphate group. The presence of 5' phosphate and 3' hydroxyl termini suggests that the dsRNA could be processed by an enzymatic activity similar to *E. coli* RNase III (for reviews, see (Dunn, 1982; Nicholson, 1999; Robertson 1990; Robertson, 1982)).

Directional cloning of 21-23 nt RNA fragments was performed by ligation of a 3' and 5' adapter oligonucleotide to the purified 21-23 mers using T4 RNA ligase. The ligation products were reverse transcribed, PCR-amplified, concatamerized, cloned, and sequenced. Over 220 short RNAs were sequenced from dsRNA processing reactions of the 39, 52 and 111 bp dsRNAs (FIG. 4A). We found the following length distribution: 1% 18 nt, 5% 19 nt, 12% 20 nt, 45% 21 nt, 28% 22 nt, 6% 23 nt, and 2% 24 nt. Sequence analysis of the 5' terminal nucleotide of the processed fragments indicated that oligonucleotides with a 5' guanosine were underrepresented. This bias was most likely introduced by T4 RNA ligase which discriminates against 5' phosphorylated guanosine as donor oligonucleotide; no significant sequence bias was seen at the 3' end. Many of the ~21 nt fragments derived from the 3' ends of the sense or antisense strand of the duplexes include 3' nucleotides that are derived from untemplated addition of nucleotides during RNA synthesis using T7 RNA polymerase. Interestingly, a significant number of endogenous *Drosophila* ~21 nt RNAs were also cloned, some of them from LTR and non-LTR retrotransposons (data not shown). This is consistent with a possible role for RNAi in transposon silencing.

The ~21 nt RNAs appear in clustered groups (FIG. 4A) which cover the entire dsRNA sequences. Apparently, the processing reaction cuts the dsRNA by leaving staggered 3' ends, another characteristic of RNase III cleavage. For the 39 bp dsRNA, two clusters of ~21 nt RNAs were found from each dsRNA-constituting strand including overhanging 3' ends, yet only one cleavage site was detected on the sense and antisense target (FIGS. 3A and 3B). If the ~21 nt fragments were present as single-stranded guide RNAs in a complex that mediates mRNA degradation, it could be assumed that at least two target cleavage sites exist, but this was not the case. This suggests that the ~21 nt RNAs may be present in double-stranded form in the endonuclease complex but that only one of the strands can be used for target RNA recognition and cleavage. The use of only one of the ~21 nt strands for target cleavage may simply be determined by the orientation in which the ~21 nt duplex is bound to the nuclease complex. This orientation is defined by the direction in which the original dsRNA was processed.

The ~21 mer clusters for the 52 bp and 111 bp dsRNA are less well defined when compared to the 39 bp dsRNA. The clusters are spread over regions of 25 to 30 nt most likely representing several distinct subpopulations of ~21 nt duplexes and therefore guiding target cleavage at several nearby sites. These cleavage regions are still predominantly separated by 20 to 23 nt intervals. The rules determining how regular dsRNA can be processed to ~21 nt fragments are not yet understood, but it was previously observed that the approx. 21-23 nt spacing of cleavage sites could be altered by a run of uridines (Zamore et al., 2000). The specificity of dsRNA cleavage by E. coli RNase III appears to be mainly controlled by antideterminants, i.e. excluding some specific base-pairs at given positions relative to the cleavage site (Zhang and Nicholson, 1997).

Figure 4B:
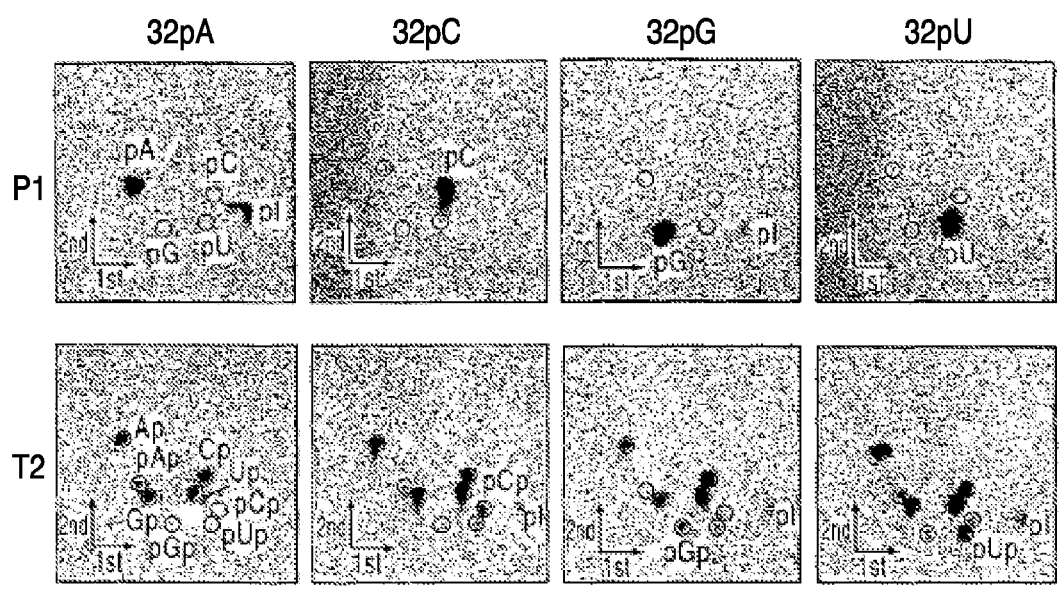

To test whether sugar-, base- or cap-modification were present in processed ~21 nt RNA fragments, we incubated radiolabeled 505 bp Pp-luc dsRNA in lysate for 1 h, isolated the ~21 nt products, and digested it with P1 or T2 nuclease to mononucleotides. The nucleotide mixture was then analyzed by 2D thin-layer chromatography (FIG. 4B). None of the four natural ribonucleotides were modified as indicated by P1 or T2 digestion. We have previously analyzed adenosine to inosine conversion in the ~21 nt fragments (after a 2 h incubation) and detected a small extent (<0.7%) deamination (Zamore et al., 2000); shorter incubation in lysate (1 h) reduced this inosine fraction to barely detectable levels. RNase T2, which cleaves 3' of the phosphodiester linkage, produced nucleoside 3'-phosphate and nucleoside 3',5'-diphosphate, thereby indicating the presence of a 5'-terminal monophosphate. All four nucleoside 3',5'-diphosphates were detected and suggest that the internucleotidic linkage was cleaved with little or no sequence-specificity. In summary, the ~21 nt fragments are unmodified and were generated from dsRNA such that 5'-monophosphates and 3'-hydroxyls were present at the 5'-end.

1.2.4 Synthetic 21 and 22 nt RNAs Mediate Target RNA Cleavage

Analysis of the products of dsRNA processing indicated that the ~21 nt fragments are generated by a reaction with all the characteristics of an RNase III cleavage reaction (Dunn, 1982; Nicholson, 1999; Robertson, 1990; Robertson, 1982). RNase III makes two staggered cuts in both strands of the dsRNA, leaving a 3' overhang of about 2 nt. We chemically synthesized 21 and 22 nt RNAs, identical in sequence to some of the cloned ~21 nt fragments, and tested them for their ability to mediate target RNA degradation (FIGS. 5A and 5B). The 21 and 22 nt RNA duplexes were incubated at 100 nM concentrations in the lysate, a 10-fold higher concentration than the 52 bp control dsRNA. Under these conditions, target RNA cleavage is readily detectable. Reducing the concentration of 21 and 22 nt duplexes from 100 to 10 nM does still cause target RNA cleavage. Increasing the duplex concentration from 100 nM to 1000 nM however does not further increase target cleavage, probably due to a limiting protein factor within the lysate.

In contrast to 29 or 30 bp dsRNAs that did not mediate RNAi, the 21 and 22 nt dsRNAs with overhanging 3' ends of 2 to 4 nt mediated efficient degradation of target RNA (duplexes 1, 3, 4, 6, FIGS. 5A and 5B). Blunt-ended 21 or 22 nt dsRNAs (duplexes 2, 5, and 7, FIGS. 5A and 5B) were reduced in their ability to degrade the target and indicate that overhanging 3' ends are critical for reconstitution of the RNA-protein nuclease complex. The single-stranded overhangs may be required for high affinity binding of the ~21 nt duplex to the protein components. A 5' terminal phosphate, although present after dsRNA processing, was not required to mediate target RNA cleavage and was absent from the short synthetic RNAs.

The synthetic 21 and 22 nt duplexes guided cleavage of sense as well as antisense targets within the region covered by the short duplex. This is an important result considering that a 39 bp dsRNA, which forms two pairs of clusters of ~21 nt fragments (FIG. 2), cleaved sense or antisense target only once and not twice. We interpret this result by suggesting that only one of two strands present in the ~21 nt duplex is able to guide target RNA cleavage and that the orientation of the ~21 nt duplex in the nuclease complex is determined by the initial direction of dsRNA processing. The presentation of an already perfectly processed ~21 nt duplex to the in vitro system however does allow formation of the active sequence-specific nuclease complex with two possible orientations of the symmetric RNA duplex. This results in cleavage of sense as well as antisense target within the region of identity with the 21 nt RNA duplex.

The target cleavage site is located 11 or 12 nt downstream of the first nucleotide that is complementary to the 21 or 22 nt guide sequence, i.e. the cleavage site is near center of the region covered by the 21 or 22 nt RNAs (FIGS. 4A and 4B). Displacing the sense strand of a 22 nt duplex by two nucleotides (compare duplexes 1 and 3 in FIG. 5A) displaced the cleavage site of only the antisense target by two nucleotides. Displacing both sense and antisense strand by two nucleotides shifted both cleavage sites by two nucleotides (compare duplexes 1 and 4). We predict that it will be possible to design a pair of 21 or 22 nt RNAs to cleave a target RNA at almost any given position.

The specificity of target RNA cleavage guided by 21 and 22 nt RNAs appears exquisite as no aberrant cleavage sites are detected (FIG. 5B). It should however be noted, that the nucleotides present in the 3' overhang of the 21 and 22 nt RNA duplex may contribute less to substrate recognition than the nucleotides near the cleavage site. This is based on the observation that the 3' most nucleotide in the 3' overhang of the active duplexes 1 or 3 (FIG. 5A) is not complementary to the target. A detailed analysis of the specificity of RNAi can now be readily undertaken using synthetic 21 and 22 nt RNAs.

Based on the evidence that synthetic 21 and 22 nt RNAs with overhanging 3' ends mediate RNA interference, we propose to name the ~21 nt RNAs "short interfering RNAs" or siRNAs and the respective RNA-protein complex a "small interfering ribonucleoprotein particle" or siRNP.

1.2.5 3' Overhangs of 20 nt on Short dsRNAs Inhibit RNAi

We have shown that short blunt-ended dsRNAs appear to be processed from the ends of the dsRNA. During our study of the length dependence of dsRNA in RNAi, we have also analyzed dsRNAs with 17 to 20 nt overhanging 3' ends and found to our surprise that they were less potent than blunt-ended dsRNAs. The inhibitory effect of long 3' ends was particularly pronounced for dsRNAs up to 100 bp but was less dramatic for longer dsRNAS. The effect was not due to imperfect dsRNA formation based on native gel analysis (data not shown). We tested if the inhibitory effect of long overhanging 3' ends could be used as a tool to direct dsRNA processing to only one of the two ends of a short RNA duplex.

Figure 6A:
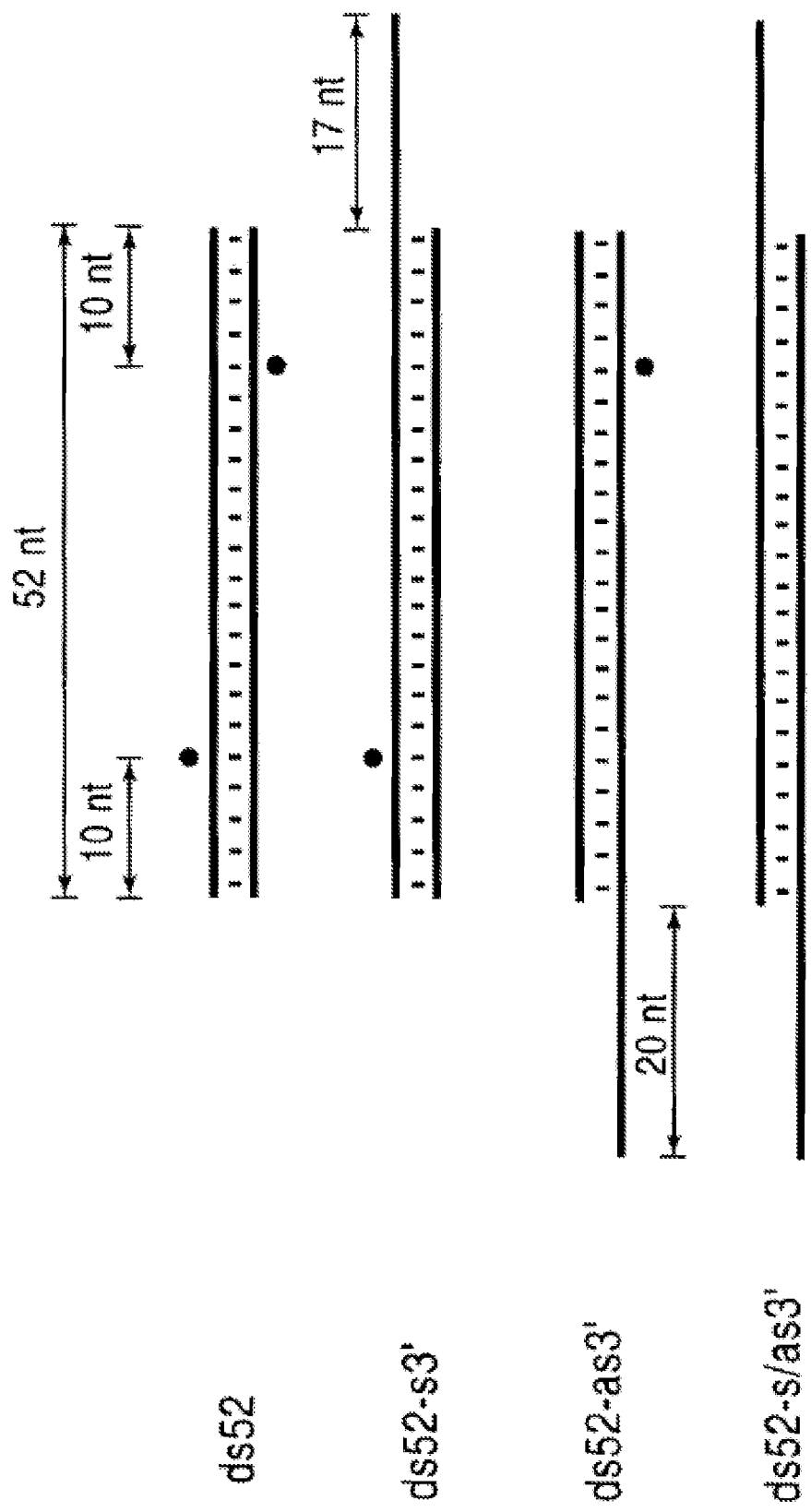
Figure 6B:
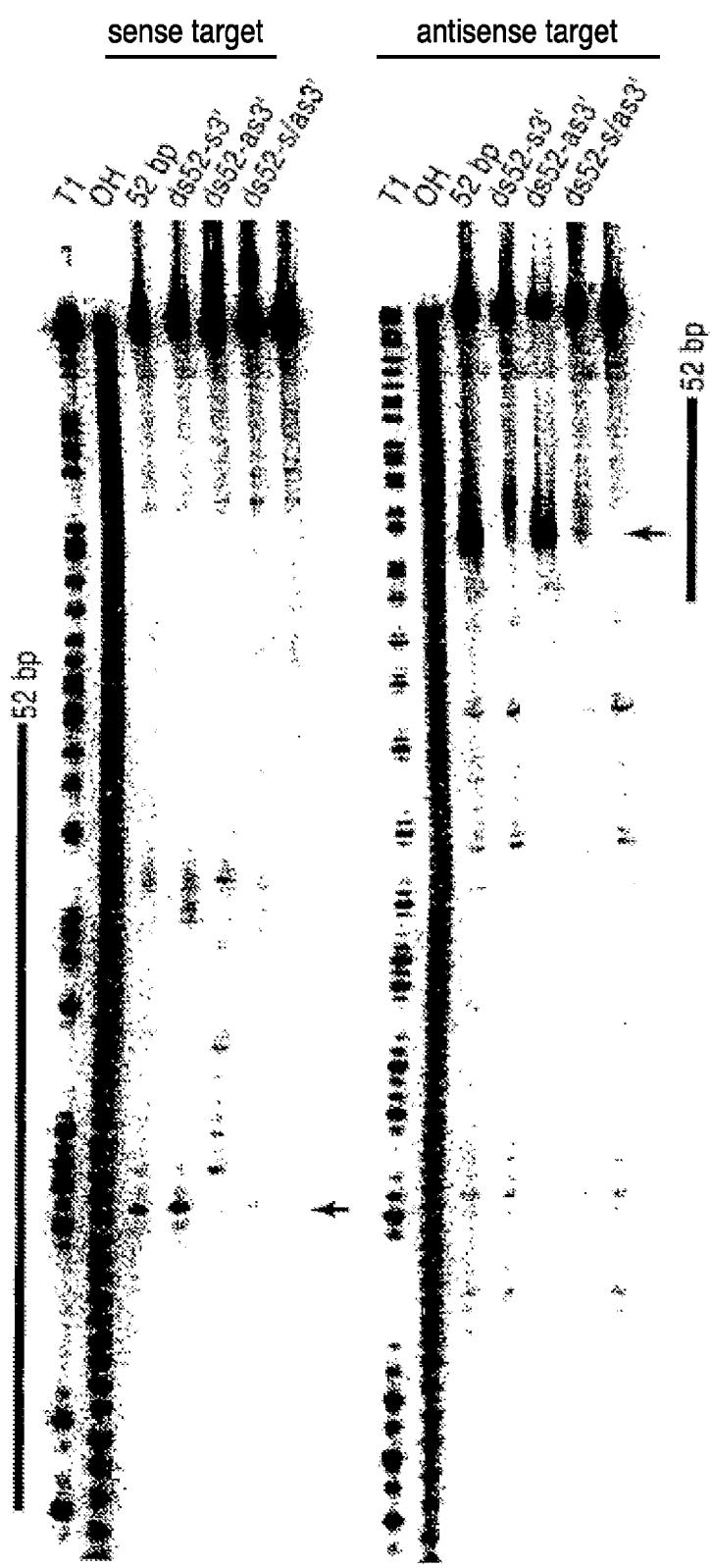

We synthesized four combinations of the 52 bp model dsRNA, blunt-ended, 3' extension on only the sense strand, 3' extension on only the antisense strand, and double 3' extension on both strands, and mapped the target RNA cleavage sites after incubation in lysate (FIGS. 6A and 6B). The first and predominant cleavage site of the sense target was lost when the 3' end of the antisense strand of the duplex was extended, and vice versa, the strong cleavage site of the antisense target was lost when the 3' end of sense strand of the duplex was extended. 3' extensions on both strands rendered the 52 bp dsRNA virtually inactive. One explanation for the dsRNA inactivation by ~20 nt 3' extensions could be the association of single-stranded RNA-binding proteins which could interfere with the association of one of the dsRNA-processing factors at this end. This result is also consistent with our model where only one of the strands of the siRNA duplex in the assembled siRNP is able to guide target RNA cleavage. The orientation of the strand that guides RNA cleavage is defined by the direction of the dsRNA processing reaction. It is likely that the presence of 3' staggered ends may facilitate the assembly of the processing complex. A block at the 3' end of the sense strand will only permit dsRNA processing from the opposing 3' end of the antisense strand. This in turn generates siRNP complexes in which only the antisense strand of the siRNA duplex is able to guide sense target RNA cleavage. The same is true for the reciprocal situation.

The less pronounced inhibitory effect of long 3' extensions in the case of longer dsRNAs (≥500 bp, data not shown) suggests to us that long dsRNAs may also contain internal dsRNA-processing signals or may get processed cooperatively due to the association of multiple cleavage factors.

1.2.6 A Model for dsRNA-Directed mRNA Cleavage

The new biochemical data update the model for how dsRNA targets mRNA for destruction (FIG. 7). Double-stranded RNA is first processed to short RNA duplexes of predominantly 21 and 22 nt in length and with staggered 3' ends similar to an RNase III-like reaction (Dunn, 1982; Nicholson, 1999; Robertson, 1982). Based on the 21-23 nt length of the processed RNA fragments it has already been speculated that an RNase III-like activity may be involved in RNAi (Bass, 2000). This hypothesis is further supported by the presence of 5' phosphates and 3' hydroxyls at the termini of the siRNAs as observed in RNase III reaction products (Dunn, 1982; Nicholson, 1999). Bacterial RNase III and the eukaryotic homologs Rnt1p in *S. cerevisiae* and Pac1p in *S. pombe* have been shown to function in processing of ribosomal RNA as well as snRNA and snoRNAs (see for example Chanfreau et al., 2000).

Little is known about the biochemistry of RNase III homologs from plants, animals or human. Two families of RNase III enzymes have been identified predominantly by database-guided sequence analysis or cloning of cDNAs. The first RNase III family is represented by the 1327 amino acid long *D. melanogaster* protein drosha (Acc. AF116572). The C-terminus is composed of two RNase III and one dsRNA-binding domain and the N-terminus is of unknown function. Close homologs are also found in *C. elegans* (Acc. AF160248) and human (Acc. AF189011) (Filippov et al., 2000; Wu et al., 2000). The drosha-like human RNase III was recently cloned and characterized (Wu et al., 2000). The gene is ubiquitously expressed in human tissues and cell lines, and the protein is localized in the nucleus and the nucleolus of the cell. Based on results inferred from antisense inhibition studies, a role of this protein for rRNA was suggested. The second class is represented by the *C. elegans* gene K12H4.8 (Acc. S44849) coding for a 1822 amino acid long protein. This protein has an N-terminal RNA helicase motif which is followed by 2 RNase III catalytic domains and a dsRNA-binding motif, similar to the drosha RNase III family. There are close homologs in *S. pombe* (Acc. Q09884), *A. thaliana* (Acc. AF187317), *D. melanogaster* (Acc. AE003740), and human (Acc. AB028449) (Filippov et al., 2000; Jacobsen et al., 1999; Matsuda et al., 2000). Possibly the K12H4.8 RNase III/helicase is the likely candidate to be involved in RNAi.

Genetic screens in *C. elegans* identified rde-1 and rde-4 as essential for activation of RNAi without an effect on transposon mobilization or co-suppression (Dernburg et al., 2000; Grishok et al., 2000; Ketting and Plasterk, 2000; Tabara et al., 1999). This led to the hypothesis that these genes are important for dsRNA processing but are not involved in mRNA target degradation. The function of both genes is as yet unknown, the rde-1 gene product is a member of a family of proteins similar to the rabbit protein eIF2C (Tabara et al., 1999), and the sequence of rde-4 has not yet been described. Future biochemical characterization of these proteins should reveal their molecular function.

Processing to the siRNA duplexes appears to start from the ends of both blunt-ended dsRNAs or dsRNAs with short (1-5 nt) 3' overhangs, and proceeds in approximately 21-23 nt steps. Long (~20 nt) 3' staggered ends on short dsRNAs suppress RNAi, possibly through interaction with single-stranded RNA-binding proteins. The suppression of RNAi by single-stranded regions flanking short dsRNA and the lack of siRNA formation from short 30 bp dsRNAs may explain why structured regions frequently encountered in mRNAs do not lead to activation of RNAi.

Without wishing to be bound by theory, we presume that the dsRNA-processing proteins or a subset of these remain associated with the siRNA duplex after the processing reaction. The orientation of the siRNA duplex relative to these proteins determines which of the two complementary strands functions in guiding target RNA degradation. Chemically synthesized siRNA duplexes guide cleavage of sense as well as antisense target RNA as they are able to associate with the protein components in either of the two possible orientation.

The remarkable finding that synthetic 21 and 22 nt siRNA duplexes can be used for efficient mRNA degradation provides new tools for sequence-specific regulation of gene expression in functional genomics as well as biomedical studies. The siRNAs may be effective in mammalian systems where long dsRNAs cannot be used due to the activation of the PKR response (Clemens, 1997). As such, the siRNA duplexes represent a new alternative to antisense or ribozyme therapeutics.

EXAMPLE 2

RNA Interference in Human Tissue Cultures 2.1 Methods 2.1.1 RNA Preparation 21 nt RNAs were chemically synthesized using Expedite RNA phosphoramidites and thymidine phosphoramidite (Proligo, Germany). Synthetic oligonucleotides were deprotected and gel-purified (Example 1), followed by Sep-Pak C18 cartridge (Waters, Milford, Mass., USA) purification (Tuschl, 1993). The siRNA sequences targeting GL2 (Acc. X65324) and GL3 luciferase (Acc. U47296) corresponded to the coding regions 153-173 relative to the first nucleotide of the start codon, siRNAs targeting RL (Acc. AF025846) corresponded to region 119-129 after the start codon. Longer RNAs were transcribed with T7 RNA polymerase from PCR products, followed by gel and Sep-Pak purification. The 49 and 484 bp GL2 or GL3 dsRNAs corresponded to position 113-161 and 113-596, respectively, relative to the start of translation; the 50 and 501 bp RL dsRNAs corresponded to position 118-167 and 118-618, respectively. PCR templates for dsRNA synthesis targeting humanized GFP (hG) were amplified from pAD3 (Kehlenbach, 1998), whereby 50 and 501 bp hG dsRNA corresponded to position 118-167 and 118-618 respectively, to the start codon.

For annealing of siRNAs, 20 µM single strands were incubated in annealing buffer (100 mM potassium acetate, 30 mM HEPES-KOH at pH 7.4, 2 mM magnesium acetate) for 1 min at 90° C. followed by 1 h at 37° C. The 37° C. incubation step was extended overnight for the 50 and 500 bp dsRNAs and these annealing reactions were performed at 8.4 µM and 0.84 µM strand concentrations, respectively.

2.1.2 Cell Culture

S2 cells were propagated in Schneider's *Drosophila* medium (Life Technologies) supplemented with 10% FBS, 100 units/ml penicillin and 100 µg/ml streptomycin at 25° C. 293, NIH/3T3, HeLa S3, COS-7 cells were grown at 37° C. in Dulbecco's modified Eagle's medium supplemented with 10% FBS, 100 units/ml penicillin and 100 µg/ml streptomycin. Cells were regularly passaged to maintain exponential growth. 24 h before transfection at approx. 80% confluency, mammalian cells were trypsinized and diluted 1:5 with fresh medium without antibiotics (1–3×10$^5$ cells/ml) and transferred to 24-well plates (500 µl/well). S2 cells were not trypsinized before splitting. Transfection was carried out with Lipofectamine 2000 reagent (Life Technologies) as described by the manufacturer for adherent cell lines. Per well, 1.0 µg pGL2-Control (Promega) or pGL3-Control (Promega), 0.1 µg pRL-TK (Promega) and 0.28 µg siRNA duplex or dsRNA, formulated into liposomes, were applied; the final volume was 600 µl per well. Cells were incubated 20 h after transfection and appeared healthy thereafter. Luciferase expression was subsequently monitored with the Dual luciferase assay (Promega). Transfection efficiencies were determined by fluorescence microscopy for mammalian cell lines after co-transfection of 1.1 µg hGFP-encoding pAD3 and 0.28 µg invGL2 in GL2 siRNA and were 70-90%. Reporter plasmids were amplified in XL-1 Blue (Stratagene) and purified using the Qiagen EndoFree Maxi Plasmid Kit.

2.2 Results and Discussion

To test whether siRNAs are also capable of mediating RNAi in tissue culture, we synthesized 21 nt siRNA duplexes with symmetric 2 nt 3' overhangs directed against reporter genes coding for sea pansy (*Renilla reniformis*) and two sequence variants of firefly (*Photinus pyralis*, GL2 and GL3) luciferases (FIG. 8a, b). The siRNA duplexes were co-transfected with the reporter plasmid combinations pGL2/pRL or pGL3/pRL into *D. melanogaster* Schneider S2 cells or mammalian cells using cationic liposomes. Luciferase activities were determined 20 h after transfection. In all cell lines tested, we observed specific reduction of the expression of the reporter genes in the presence of cognate siRNA duplexes (FIG. 9a-j). Remarkably, the absolute luciferase expression levels were unaffected by non-cognate siRNAs, indicating the absence of harmful side effects by 21 nt RNA duplexes (e.g. FIG. 10a-d for HeLa cells). In *D. melanogaster* S2 cells (FIG. 9a, b), the specific inhibition of luciferases was complete. In mammalian cells, where the reporter genes were 50- to 100-fold stronger expressed, the specific suppression was less complete (FIG. 9c-j). GL2 expression was reduced 3- to 12-fold, GL3 expression 9- to 25-fold and RL expression 1- to 3-fold, in response to the cognate siRNAs. For 293 cells, targeting of RL luciferase by RL siRNAs was ineffective, although GL2 and GL3 targets responded specifically (FIG. 9i, j). The lack of reduction of RL expression in 293 cells may be due to its 5- to 20-fold higher expression compared to any other mammalian cell line tested and/or to limited accessibility of the target sequence due to RNA secondary structure or associated proteins. Nevertheless, specific targeting of GL2 and GL3 luciferase by the cognate siRNA duplexes indicated that RNAi is also functioning in 293 cells.

The 2 nt 3' overhang in all siRNA duplexes; except for uGL2, was composed of (2'-deoxy) thymidine. Substitution of uridine by thymidine in the 3' overhang was well tolerated in the *D. melanogaster* in vitro system and the sequence of the overhang was uncritical for target recognition. The thymidine overhang was chosen, because it is supposed to enhance nuclease resistance of siRNAs in the tissue culture medium and within transfected cells. Indeed, the thymidine-modified GL2 siRNA was slightly more potent than the unmodified uGL2 siRNA in all cell lines tested (FIG. 9a, c, e, g, i). It is conceivable that further modifications of the 3' overhanging nucleotides may provide additional, benefits to the delivery and stability of siRNA duplexes.

In co-transfection experiments, 25 nM siRNA duplexes with respect to the final volume of tissue culture medium were used (FIG. 9, 10). Increasing the siRNA concentration to 100 nM did not enhance the specific silencing effects, but started to affect transfection efficiencies due to competition for liposome encapsulation between plasmid DNA and siRNA (data not shown). Decreasing the siRNA concentration to 1.5 nM did not reduce the specific silencing effect (data not shown), even though the siRNAs were now only 2- to 20-fold more concentrated than the DNA plasmids. This indicates that siRNAs are extraordinarily powerful reagents for mediating gene silencing and that siRNAs are effective at concentrations that are several orders of magnitude below the concentrations applied in conventional antisense or ribozyme gene targeting experiments.

In order to monitor the effect of longer dsRNAs on mammalian cells, 50 and 500 bp dsRNAs cognate to the reporter genes were prepared. As nonspecific control, dsRNAs from humanized GFP (hG) (Kehlenbach, 1998) was used. When dsRNAs were co-transfected, in identical amounts (not concentrations) to the siRNA duplexes, the reporter gene expression was strongly and unspecifically reduced. This effect is illustrated for HeLa cells as a representative example (FIG. 10a-d). The absolute luciferase activities were decreased unspecifically 10- to 20-fold by 50 bp dsRNA and 20- to 200-fold by 500 bp dsRNA co-transfection, respectively. Similar unspecific effects were observed for COS-7 and NIH/3T3 cells. For 293 cells, a 10- to 20-fold unspecific reduction was observed only for 500 bp dsRNAs. Unspecific reduction in reporter gene expression by dsRNA >30 bp was expected as part of the interferon response.

Surprisingly, despite the strong unspecific decrease in reporter gene expression, we reproducibly detected additional sequence-specific, dsRNA-mediated silencing. The specific silencing effects, however, were only apparent when the relative reporter gene activities were normalized to the hG dsRNA controls (FIGS. 10e, f). A 2- to 10-fold specific reduction in response to cognate dsRNA was observed, also in the other three mammalian cell lines tested (data not shown). Specific silencing effects with dsRNAs (356-1662 bp) were previously reported in CHO-K1 cells, but the amounts of dsRNA required to detect a 2- to 4-fold specific reduction were about 20-fold higher than in our experiments (Ui-Tei, 2000). Also CHO-KI cells appear to be deficient in the interferon response. In another report, 293, NIH/3T3 and BHK-21 cells were tested for RNAi using luciferase/lacZ reporter combinations and 829 bp specific lacZ or 717 bp unspecific GFP dsRNA (Caplen, 2000). The failure of detecting RNAi in this case may be due to the less sensitive luciferase/lacZ reporter assay and the length differences of target and control dsRNA. Taken together, our results indicate that RNAi is active in mammalian cells, but that the silencing effect is difficult to detect, if the interferon system is activated by dsRNA >30 bp.

In summary, we have demonstrated for the first time siRNA-mediated gene silencing in mammalian cells. The use of short siRNAs holds great promise for inactivation of gene function in human tissue culture and the development of gene-specific therapeutics.

EXAMPLE 3

Specific Inhibition of Gene Expression by RNA Interference 3.1 Materials and Methods
3.1.1 RNA Preparation and RNAi Assay Chemical RNA synthesis, annealing, and luciferase-based RNAi assays were performed as described in Examples 1 or 2 or in previous publications (Tuschl et al., 1999; Zamore et al., 2000). All siRNA duplexes were directed against firefly luciferase, and the luciferase mRNA sequence was derived from pGEM-luc (GenBank acc. X65316) as described (Tusch et al., 1999). The siRNA duplexes were incubated in $D.$ $melanogaster$ RNA/translation reaction for 15 min prior to addition of mRNAs. Translation-based RNAi assays were performed at least in triplicate.

For mapping of sense target RNA cleavage, a 177-nt transcript was generated, corresponding to the firefly luciferase sequence between positions 113-273 relative to the start codon, followed by the 17-nt complement of the SP6 promoter sequence. For mapping of antisense target RNA cleavage, a 166-nt transcript was produced from a template, which was amplified from plasmid sequence by PCR using 5' primer TAATACGACTCACTATAGAGCCCATATCGTTTCATA (T7 promoter in bold) [SEQ ID NO: 5] and 3' primer AGAG-GATGGAACCGCTGG [SEQ ID NO: 6]. The target sequence corresponds to the complement of the firefly luciferase sequence between positions 50-215 relative to the start codon. Guanylyl transferase labelling was performed as previously described (Zamore et al., 2000). For mapping of target RNA cleavage, 100 nM siRNA duplex was incubated with 5 to 10 nM target RNA in $D.$ $melanogaster$ embryo lysate under standard conditions (Zamore et al., 2000) for 2 h at 25EC. The reaction was stopped by the addition of 8 volumes of proteinase K buffer (200 mM Tris-HCl pH 7.5, 25 mM EDTA, 300 mM NaCl, 2% w/v sodium dodecyl sulfate). Proteinase K (E.M. Merck, dissolved in water) was added to a final concentration of 0.6 mg/ml. The reactions were then incubated for 15 min at 65EC, extracted with phenol/chloroform/isoamyl alcohol (25:24:1) and precipitated with 3 volumes of ethanol. Samples were located on 6% sequencing gels. Length standards were generated by partial RNase T1 digestion and partial base hydrolysis of the cap-labelled sense or antisense target RNAs.
3.2 Results
3.2.1 Variation of the 3' Overhang in Duplexes of 21-nt siRNAs As described above, 2 or 3 unpaired nucleotides at the 3' end of siRNA duplexes were more efficient in target RNA degradation than the respective blunt-ended duplexes. To perform a more comprehensive analysis of the function of the terminal nucleotides, we synthesized five 21-nt sense siRNAs, each displayed by one nucleotide relative to the target RNA, and eight 21-nt antisense siRNAs, each displaced by one nucleotide relative to the target (FIG. 11 Part I A). By combining sense and antisense siRNAs, eight series of siRNA duplexes with synthetic overhanging ends were generated covering a range of 7-nt 3' overhang to 4-nt 5' overhang. The interference of siRNA duplexes was measured using the dual luciferase assay system (Tuschl et al., 1999; Zamore et al., 2000). siRNA duplexes were directed against firefly luciferase mRNA, and sea pansy luciferase mRNA was used as internal control. The luminescence ratio of target to control luciferase activity was determined in the presence of siRNA duplex and was normalized to the ratio observed in the absence of dsRNA. For comparison, the interference ratios of long dsRNAs (39 to 504 pb) are shown in FIG. 11 Part I B. The interference ratios were determined at concentrations of 5 nM for long dsRNAs (FIG. 11 Part I A) and at 100 nM for siRNA duplexes (FIG. 11 Part I C-D, Part II E-G, Part III -J). The 100 nM concentrations of siRNAs was chosen, because complete processing of 5 nM 504 bp dsRNA would result in 120 nM total siRNA duplexes.

The ability of 21-nt siRNA duplexes to mediate RNAi is dependent on the number of overhanging nucleotides or base pairs formed. Duplexes with four to six 3' overhanging nucleotides were unable to mediate RNAi (FIG. 11 Part I C-D, Part II E-F), as were duplexes with two or more 5' overhanging nucleotides (FIG. 11 Part II G, Part III H-J). The duplexes with 2-nt 3' overhangs were most efficient in mediating RNA interference, though the efficiency of silencing was also sequence-dependent, and up to 12-fold differences were observed for different siRNA duplexes with 2-nt 3' overhangs (compare FIG. 11 Part I D, Part II E-G, Part III H). Duplexes with blunted ends, 1-nt 5' overhang or 1- to 3-nt 3' overhangs were sometimes functional. The small silencing effect observed for the siRNA duplex with 7-nt 3' overhang (FIG. 11 Part I C) may be due to an antisense effect of the long 3' overhang rather than due to RNAi. Comparison of the efficiency of RNAi between long dsRNAs (FIG. 11 Part I B) and the most effective 21-nt siRNA duplexes (FIG. 11 Part II E, Part II G, Part III H) indicates that a single siRNA duplex at 100 nM concentration can be as effective as 5 nM 504 bp dsRNA.
3.2.2 Length Variation of the Sense siRNA Paired to an Invariant 21-nt Antisense siRNA In order to investigate the effect of length of siRNA on RNAi, we prepared 3 series of siRNA duplexes, combining three 21-nt antisense strands with eight, 18- to 25-nt sense strands. The 3' overhang of the antisense siRNA was fixed to 1, 2, or 3 nt in each siRNA duplex series, while the sense siRNA was varied at its 3' end (FIG. 12 Part I A). Independent of the length of the sense siRNA, we found that duplexes with 2-nt 3' overhang of antisense siRNA (FIG. 12 Part II C) were more active than those with 1- or 3-nt 3' overhang (FIG. 12 Part I B, Part II D). In the first series, with 1-nt 3' overhang of antisense siRNA, duplexes with a 21- and 22-nt sense siRNAs, carrying a 1- and 2-nt 3' overhang of sense siRNA, respectively, were most active. Duplexes with 19- to 25-nt sense siRNAs were also able to mediate RNA, but to a lesser extent. Similarly, in the second series, with 2-nt overhang of antisense siRNA, the 21-nt siRNA duplex with 2-nt 3' overhang was most active, and any other combination with the 18- to 25-nt sense siRNAs was active to a significant degree. In the last series, with 3-nt antisense siRNA 3' overhang, only the duplex with a 20-nt sense siRNA and the 2-nt sense 3' overhang was able to reduce target RNA expression. Together, these results indicate that the length of the siRNA as well as the length of the 3' overhang are important, and that duplexes of 21-nt siRNAs with 2-nt 3' overhang are optimal for RNAi.

3.2.3 Length Variation of siRNA Duplexes with a Constant 2-nt 3' Overhang

We then examined the effect of simultaneously changing the length of both siRNA strands by maintaining symmetric 2-nt 3' overhangs (FIG. 13A). Two series of siRNA duplexes were prepared including the 21-nt siRNA duplex of FIG. 11 Part III H as reference. The length of the duplexes was varied between 20 to 25 bp extending the base-paired segment at the 3' end of the sense siRNA (FIG. 13B) or at the 3' end of the antisense siRNA (FIG. 13C). Duplexes of 20 to 23 bp caused specific repression of target luciferase activity, but the 21-nt siRNA duplex was at least 8-fold more efficient than any of the other duplexes. 24- and 25-nt siRNA duplexes did not result in any detectable interference. Sequence-specific effects were minor as variations on both ends of the duplex produced similar effects.

3.2.4 2'-Deoxy and 2'-O-methyl-modified siRNA Duplexes

To assess the importance of the siRNA ribose residues for RNAi, duplexes with 21-nt siRNAs and 2-nt 3' overhangs with 2'-deoxy or 2'-O-methyl-modified strands were examined (FIG. 14). Substitution of the 2-nt 3' overhangs by 2'-deoxy nucleotides had no effect, and even the replacement of two additional ribonucleotides adjacent to the overhangs in the paired region, produced significantly active siRNAs. Thus, 8 out of 42 nt of a siRNA duplex were replaced by DNA residues without loss of activity. Complete substitution of one or both siRNA strands by 2'-deoxy residues, however, abolished RNAi, as did substitution by 2'-O-methyl residues.

3.2.5 Definition of Target RNA Cleavage Sites

Target RNA cleavage positions were previously determined for 22-nt siRNA duplexes and for a 21-nt/22-nt duplex. It was found that the position of the target RNA cleavage was located in the centre of the region covered by the siRNA duplex, 11 or 12 nt downstream of the first nucleotide that was complementary to the 21- or 22-nt siRNA guide sequence. Five distinct 21-nt siRNA duplexes with 2-nt 3' overhang (FIG. 15A) were incubated with 5' cap-labelled sense or antisense target RNA in *D. melanogaster* lysate (Tuschl et al., 1999; Zamore et al., 2000). The 5' cleavage products were resolved on sequencing gels (FIG. 15B). The amount of sense target RNA cleaved correlates with the efficiency of siRNA duplexes determined in the translation-based assay, and siRNA duplexes 1, 2 and 4 (FIG. 15B and 11 Part II E, Part II G, Part III H) cleave target RNA faster than duplexes 3 and 5 (FIG. 15B and 11 Part I D, Part II F). Notably, the sum of radioactivity of the 5' cleavage product and the input target RNA were not constant over time, and the 5' cleavage products did not accumulate. Presumably, the cleavage products, once released from the siRNA-endonuclease complex, are rapidly degraded due to the lack of either of the poly(A) tail of the 5'-cap.

The cleavage sites for both, sense and antisense target RNAs were located in the middle of the region spanned by the siRNA duplexes. The cleavage sites for each target produced by the 5 different duplexes varied by 1-nt according to the 1-nt displacement of the duplexes along the target sequences. The targets were cleaved precisely 11 nt downstream of the target position complementary to the 3'-most nucleotide of the sequence-complementary guide siRNA (FIG. 15A, B).

In order to determine, whether the 5' or the 3' end of the guide siRNA sets the ruler for target RNA cleavage, we devised the experimental strategy outlined in FIGS. 16A and B. A 21-nt antisense siRNA, which was kept invariant for this study, was paired with sense siRNAs that were modified at either of their 5' or 3' ends. The position of sense and antisense target RNA cleavage was determined as described above. Changes in the 3' end of the sense siRNA, monitored for 1-nt 5' overhang to 6-nt 3' overhang, did neither effect the position of sense nor antisense target RNA cleavage (FIG. 16C). Changes in the 5' end of the sense siRNA did not affect the sense target RNA cleavage (FIG. 16D, top panel), which was expected because the antisense siRNA was unchanged. However, the antisense target RNA cleavage was affected and strongly dependent on the 5' end of the sense siRNA (FIG. 16D, bottom panel). The antisense target was only cleaved, when the sense siRNA was 20 or 21 nt in size, and the position of cleavage different by 1-nt, suggesting that the 5' end of the target-recognizing siRNA sets the ruler for target RNA cleavage. The position is located between nucleotide 10 and 11 when counting in upstream direction from the target nucleotide paired to the 5'-most nucleotide of the guide siRNA (see also FIG. 15A).

3.2.6 Sequence Effects and 2'-deoxy Substitutions in the 3' Overhang

A 2-nt 3' overhang is preferred for siRNA function. We wanted to know, if the sequence of the overhanging nucleotides contributes to target recognition, or if it is only a feature required for reconstitution of the endonuclease complex (RISC or siRNP). We synthesized sense and antisense siRNAs with AA, CC, GG, UU, and UG 3' overhangs and included the 2'-deoxy modifications TdG and TT. The wild-type siRNAs contained AA in the sense 3' overhang and UG in the antisense 3' overhang (ANUG). All siRNA duplexes were functional in the interference assay and reduced target expression at least 5-fold (FIG. 17). The most efficient siRNA duplexes that reduced target expression more than 10-fold, were of the sequence type NN/UG, NN/UU, NN/TdG, and NN/TT (N, any nucleotide). siRNA duplexes with an antisense siRNA 3' overhang of AA, CC or GG were less active by a factor 2 to 4 when compared to the wild-type sequence UG or the mutant UU. This reduction in RNAi efficiency is likely due to the contribution of the penultimate 3' nucleotide to sequence-specific target recognition, as the 3' terminal nucleotide was changed from G to U without effect.

Changes in the sequence of the 3' overhang of the sense siRNA did not reveal any sequence-dependent effects, which was expected, because the sense siRNA must not contribute to sense target mRNA recognition.

3.2.7 Sequence Specificity of Target Recognition

In order to examine the sequence-specificity of target recognition, we introduced sequence changes into the paired segments of siRNA duplexes and determined the efficiency of silencing. Sequence changes were introduced by inverting short segments of 3- or 4-nt length or as point mutations (FIG. 18). The sequence changes in one siRNA strand were compensated in the complementary siRNA strand to avoid perturbing the base-paired siRNA duplex structure. The sequence of all 2-nt 3' overhangs was TT (T, 2'-deoxythymidine) to reduce costs of synthesis. The TT/TT reference siRNA duplex was comparable in RNAi to the wild-type siRNA duplex AA/UG (FIG. 17). The ability to mediate reporter mRNA destruction was quantified using the translation-based luminescence assay. Duplexes of siRNAs with inverted sequence segments showed dramatically reduced ability for targeting the firefly luciferase reporter (FIG. 18). The sequence changes located between the 3' end and the middle of the antisense siRNA completely abolished target RNA recognition, but mutations near the 5' end of the antisense siRNA exhibit a small degree of silencing. Transversion of the A/U base pair located directly opposite of the predicted target RNA cleavage site, or one nucleotide further away from the predicted site, prevented target RNA cleavage, therefore indicating that single mutation within the centre of a siRNA duplex discriminate between mismatched targets.

3.3 Discussion siRNAs are valuable reagents for inactivation of gene expression, not only in insect cells, but also in mammalian cells, with a great potential for therapeutic application. We have systematically analyzed the structural determinants of siRNA duplexes required to promote efficient target RNA degradation in *D. melanogaster* embryo lysate, thus providing rules for the design of most potent siRNA duplexes. A perfect siRNA duplex is able to silence gene expression with an efficiency comparable to a 500 bp dsRNA, given that comparable quantities of total RNA are used.

3.4 The siRNA User Guide

Efficiently silencing siRNA duplexes are preferably composed of 21-nt antisense siRNAs, and should be selected to form a 19 bp double helix with 2-nt 3' overhanging ends. 2'-deoxy substitutions of the 2-nt 3' overhanging ribonucleotides do not affect RNAi, but help to reduce the costs of RNA synthesis and may enhance RNAse resistance of siRNA duplexes. More extensive 2'-deoxy or 2'-O-methyl modifications, however, reduce the ability of siRNAs to mediate RNAi, probably by interfering with protein association for siRNAP assembly.

Target recognition is a highly sequence-specific process, mediated by the siRNA complementary to the target. The 3'-most nucleotide of the guide siRNA does not contribute to specificity of target recognition, while the penultimate nucleotide of the 3' overhang affects target RNA cleavage, and a mismatch reduces RNAi 2- to 4-fold. The 5' end of a guide siRNA also appears more permissive for mismatched target RNA recognition when compared to the 3' end. Nucleotides in the centre of the siRNA, located opposite the target RNA cleavage site, are important specificity determinants and even single nucleotide changes reduce RNAi to undetectable levels. This suggests that siRNA duplexes may be able to discriminate mutant or polymorphic alleles in gene targeting experiments, which may become an important feature for future therapeutic developments.

Sense and antisense siRNAs, when associated with the protein components of the endonuclease complex or its commitment complex, were suggested to play distinct roles; the relative orientation of the siRNA duplex in this complex defines which strand can be used for target recognition. Synthetic siRNA duplexes have dyad symmetry with respect to the double-helical structure, but not with respect to sequence. The association of siRNA duplexes with the RNAi proteins in the *D. melanogaster* lysate will lead to formation of two asymmetric complexes. In such hypothetical complexes, the chiral environment is distinct for sense and antisense siRNA, hence their function. The prediction obviously does not apply to palindromic siRNA sequences, or to RNAi proteins that could associate as homodimers. To minimize sequence effects, which may affect the ratio of sense and antisense-targeting siRNPs, we suggest to use siRNA sequences with identical 3' overhanging sequences. We recommend to adjust the sequence of the overhang of the sense siRNA to that of the antisense 3' overhang, because the sense siRNA does not have a target in typical knock-down experiments. Asymmetry in reconstitution of sense and antisense-cleaving siRNPs could be (partially) responsible for the variation in RNAi efficiency observed for various 21-nt siRNA duplexes with 2-nt 3' overhangs used in this study (FIG. 14). Alternatively, the nucleotide sequence at the target site and/or the accessibility of the target RNA structure may be responsible for the variation in efficiency for these siRNA duplexes.

References

Bass, B. L. (2000). Double-stranded RNA a template for gene silencing. Cell 101, 235-238.

Bosher, J. M., and Labouesse, M. (2000). RNA interference: genetic wand and genetic watchdog. Nat. Cell Biol. 2, E31-36.

Caplen, N. J., Fleenor, J., Fire, A., and Morgan, R. A. (2000). dsRNA-mediated gene silencing in cultured *Drosophila* cells: a tissue culture model for the analysis of RNA interference. Gene 252, 95-105.

Catalanotto, C., Azzalin, G., Macino, G., and Cogoni, C. (2000). Gene silencing in worms and fungi. Nature 404, 245.

Chanfreau, G., Buckle. M., and Jacquier, A. (2000). Recognition of a conserved class of RNA tetraloops by *Saccharomyces cerevisiae* RNase III. Proc. Natl. Acad. Sci. USA 97, 3142-3147.

Clemens, M. J. (1997). PKR—a protein kinase regulated by double-stranded RNA. Int. J. Biochem. Cell Biol. 29, 945-949.

Cogoni, C., and Macino, G. (1999). Homology-dependent gene silencing in plants and fungi: a number of variations on the same theme. Curr. Opin. Microbiol. 2, 657-662.

Dalmay, T., Hamilton, A., Rudd, S., Angell, S., and Baulcombe, D. C. (2000). An RNA-dependent RNA polymerase gene in *Arabidopsis* is required for posttranscriptional gene silencing mediated by a transgene but not by a virus. Cell 101, 543-553.

Dernburg, A. F., Zalevsky, J., Colaiacovo, M. P., and Villeneuve, A. M. (2000). Transgene-mediated cosuppression in the *C. elegans* germ line. Genes & Dev. 14, 1578-1583.

Dunn, J. J. (1982). Ribonuclease III. In The Enzymes, vol 15, part B, P. D. Boyer, ed. (New York: Academic Press), pp. 485-499.

Filipov, V., Solovyev, V., Filippova, M., and Gill, S. S. (2000). A novel type of RNase III family proteins in eukaryotes. Gene 245, 213-221.

Fire, A. (1999). RNA-triggered gene silencing. Trends Genet. 15, 358-363.

Fire, A., Xu, S., Montgomery, M. K., Kostas, S. A., Driver, S. E., and Mello, C. C. (1998). Potent and specific genetic interference by double-stranded RNA in *Caenorhabditis elegans*. Nature 391, 806-811.

Grishok, A., Tabara, H., and Mello, C. C. (2000). Genetic requirements for inheritance of RNAi in *C. elegans*. Science 287, 2494-2497.

Hamilton, A. J., and Baulcombe, D. C. (1999). A species of small antisense RNA in posttranscriptional gene silencing in plants. Science 286, 950-952.

Hammond, S. M., Bernstein, E., Beach, D., and Hannon, G. J. (2000). An RNA-directed nuclease mediates post-transcriptional gene silencing in *Drosophila* cells. Nature 404, 293-296.

Jacobsen, S. E., Running, M. P., and M., M. E. (1999). Disruption of an RNA helicase/RNase III gene in *Arabidopsis* causes unregulated cell division in floral meristems. Development 126, 5231-5243.

Jensen, S., Gassama, M. P., and Heidmann, T. (1999). Taming of transposable elements by homology-dependent gene silencing. Nat. Genet. 21, 209-212.

Kehlenbach, R. H., Dickmanns, A. & Gerace, L. (1998). Nucleocytoplasmic shuttling factors including Ran and CRM1 mediate nuclear export of NFAT In vitro. J. Cell Biol. 141, 863-874.

Kennerdell, J. R., and Carthew, R. W. (1998). Use of dsRNA-mediated genetic interference to demonstrate that frizzled and frizzled 2 act in the wingless pathway. Cell 95, 1017-1026.

Ketting, R. F., Haverkamp, T. H., van Luenen, H. G., and Plasterk, R. H. (1999). Mut-7 of *C. elegans*, required for transposon silencing and RNA interference, is a homolog of Werner syndrome helicase and RNaseD. Cell 99, 133-141.

Ketting, R. F., and Plasterk, R. H. (2000). A genetic link between co-suppression and RNA interference in *C. elegans*. Nature 404, 296-298.

Lucy, A. P., Guo, H. S., Li, W. X., and Ding, S. W. (2000). Suppression of post-transcriptional gene silencing by a plant viral protein localized in the nucleus. EMBO J. 19, 1672-1680.

Matsuda, S., Ichigotani, Y., Okuda, T., Irimura, T., Nakatsugawa, S., and Hamaguchi, M. (2000). Molecular cloning and characterization of a novel human gene (HERNA) which encodes a putative RNA-helicase. Biochim. Biophys. Acta 31, 1-2.

Milligan, J. F., and Uhlenbeck, O. C. (1989). Synthesis of small RNAs using T7 RNA polymerase. Methods Enzymol. 180, 51-62.

Mourrain, P., Beclin, C., Elmayan, T., Feuerbach, F., Godon, C., Morel, J. B., Jouette, D., Lacombe, A. M., Nikic, S., Picault, N., Remoue, K., Sanial, M., Vo, T. A., and Vaucheret, H. (2000). *Arabidopsis* SGS2 and SGS3 genes are required for posttranscriptional gene silencing and natural virus resistance. Cell 101, 533-542.

Ngo, H., Tschudi, C., Gull, K., and Ullu, E. (1998). Double-stranded RNA induces mRNA degradation in *Trypanosoma* brucei. Proc. Natl. Acad. Sci. USA 95, 14687-14692.

Nicholson, A. W. (1999). Function, mechanism and regulation of bacterial ribonucleases. FEMS Microbial. Rev. 23, 371-390.

Oelgeschlager, M., Larrain, J., Geissert, D., and De Robertis, E. M. (2000). The evolutionarily conserved BMP-binding protein Twisted gastrulation promotes BMP signalling. Nature 405, 757-763.

Pan, T., and Uhlenbeck, O. C. (1992). In vitro selection of RNAs that undergo autolytic cleavage with $Pb^{2+}$. Biochemistry 31, 3887-3895.

Pelissier, T., and Wassenegger, M. (2000). A DNA target of 30 bp is sufficient for RNA-directed methylation. RNA 6, 55-65.

Plasterk, R. H., and Ketting, R. F. (2000). The silence of the genes. Curr. Opin. Genet. Dev. 10, 562-567.

Ratcliff, F. G., MacFarlane, S. A., and Baulcombe, D. C. (1999). Gene Silencing without DNA. RNA-mediated cross-protection between viruses. Plant Cell 11, 1207-1216.

Robertson, H. D. (1990). *Escherichia coli* ribonuclease III. Methods Enzymol. 181, 189-202.

Robertson, H. D. (1982). *Escherichia coli* ribonuclease III cleavage sites. Cell 30, 669-672.

Romaniuk, E., McLaughlin, L. W., Nielson, T., and Romaniuk, P. J. (1982). The effect of acceptor oligoribonucleotide sequence on the T4 RNA ligase reaction. Eur J Biochem 125, 639-643.

Sharp, P. A. (1999). RNAi and double-strand RNA. Genes & Dev. 13, 139-141.

Sijen, T., and Kooter, J. M. (2000). Post-transcriptional gene-silencing: RNAs on the attack or on the defense? Bioessays 22, 520-531.

Smardon, A., Spoerke, J., Stacey, S., Klein, M., Mackin, N., and Maine, E. (2000). EGO-1 is related to RNA-directed RNA polymerase and functions in germ-line development and RNA interference in *C. elegans*. Curr. Biol. 10, 169-178.

Svoboda, P., Stein, P., Hayashi, H., and Schultz, R. M. (2000). Selective reduction of dormant maternal mRNAs in mouse oocytes by RNA interference. Development 127, 4147-4156.

Tabara, H., Sarkissian, M., Kelly, W. G., Fleenor, J., Grishok, A., Timmons, L., Fire, A., and Mello, C. C. (1999). The rde-1 gene, RNA interference, and transposon silencing in *C. elegans*. Cell 99, 123-132.

Tuschl, T., Ng, M. M., Pieken, W., Benseler, F., and Eckstein, F. (1993). Importance of exocyclic base functional groups of central core guanosines for hammerhead ribozyme activity. Biochemistry 32, 11658-11668.

Tuschl, T., Sharp, P. A., and Bartel, D. P. (1998). Selection in vitro of novel ribozymes from a partially randomized U2 and U6 snRNA library. EMBO J. 17, 2637-2650.

Tuschl, T., Zamore, P. D., Lehmann, R., Bartel, D. P., and Sharp, P. A. (1999). Targeted mRNA degradation by double-stranded RNA in vitro. Genes & Dev. 13, 3191-3197.

Ui-Tei, K., Zenno, S., Miyata, Y. & Saigo, K. (2000). Sensitive assay of RNA interference in *Drosophila* and Chinese hamster cultured cells using firefly luciferase gene as target. FEBS Letters 479, 79-82.

Verma, S., and Eckstein, F. (1999). Modified oligonucleotides: Synthesis and strategy for users. Annu. Rev. Biochem. 67, 99-134.

Voinnet, O., Lederer, C., and Baulcombe, D. C. (2000). A viral movement protein prevents spread of the gene silencing signal in *Nicotiana benthamiana*. Cell 103, 157-167.

Wassenegger, M. (2000). RNA-directed DNA methylation. Plant Mol. Biol. 43, 203-220.

Wianny, F., and Zernicka-Goetz, M. (2000). Specific interference with gene function by double-stranded RNA in early mouse development. Nat. Cell Biol. 2, 70-75.

Wu, H., Xu, H., Miraglia, L. J., and Crooke, S. T. (2000). Human RNase III is a 160 kDa Protein Involved in Preribosomal RNA Processing. J. Biol. Chem. 17, 17.

Yang, D., Lu, H, and Erickson, J. W. (2000). Evidence that processed small dsRNAs may mediate sequence-specific mRNA degradation during RNAi in drosophilia embryos. Curr. Biol. 10, 1191-1200.

Zamore, P. D., Tuschl, T., Sharp, P. A., and Bartel, D. P. (2000). RNAi: Double-stranded RNA directs the ATP-dependent cleavage of mRNA at 21 to 23 nucleotide intervals. Cell 101, 25-33.

Zhang, K., and Nicholson, A. W. (1997). Regulation of ribonuclease III processing by double-helical sequence antideterminants. Proc. Natl. Acad. Sci. USA 94, 13437-13441.

The invention claimed is:

1. A method for reducing the level of a target mRNA in a cell in vitro, comprising contacting a cell with an isolated synthetically prepared, double-stranded RNA molecule which mediates a reduction in the level of a target mRNA, wherein said molecule consists of two separate RNA strands each independently consisting of 19-23 nucleotides, wherein said separate RNA strands form a single continuous double-stranded region and wherein at least one strand of said RNA molecule has a 3'-overhang from 1-5 nucleotides, wherein one of said strands is complementary to a portion of a target mRNA, and said RNA molecule comprises at least one stabilizing modification at the 5' end or the 3' end, or both ends, of the double-stranded RNA molecule, wherein said stabilizing modification is selected from the group consisting of a sugar modified ribonucleotide and a backbone-modified ribonucleotide containing a phosphorothioate group, wherein said sugar modified ribonucleotide 2'-OH group is replaced by a member selected from the group consisting of H, OR, R, halo, SH, SR, $NH_2$, NHR, $NR_2$ and CN, wherein R is $C_1$-$C_6$ alkyl, $C_2$-$C_6$ alkenyl, $C_2$-$C_6$ alkynyl, and halo is F, C l , Br or I.

2. The method of claim 1, wherein both strands of said double-stranded RNA molecule have a 3'-overhang from 1-3 nucleotides.

3. The method of claim 1, wherein both strands of said double-stranded RNA molecule have a 3'-overhang of 2 nucleotides.

4. The method of claim 1, wherein each strand has a length from 20-22 nucleotides.

5. The method of claim 4, wherein both strands of said double-stranded RNA molecule have a 3'-overhang from 1-3 nucleotides.

6. The method of claim 4, wherein both strands of said double-stranded RNA molecule have a 3'-overhang of 2 nucleotides.

7. The method of claim 1, wherein the double-stranded RNA molecule comprises at least one sugar-modified ribonucleotide, wherein the 2'—OH group of said sugar-modified ribonucleotide is replaced by a group selected from H, OR, R, halo, SH, $SR_1$, $NH_2$, NHR, $NR_2$ or CN, wherein R is $C_1$-$C_6$ alkyl, $C_2$-$C_6$ alkenyl or $C_2$-$C_6$ alkynyl and halo is F, Cl, Br or I.

8. The method of claim 1, wherein the double-stranded RNA molecule comprises at least one backbone-modified ribonucleotide containing a phosphorothioate group.

9. The method according to claim 1, wherein said 3' overhang consists of purine nucleotides.

10. The method according to claim 1, wherein pyrimidine nucleotides in said 3' overhang is substituted by modified nucleotide analogues.

11. The method according to claim 10, wherein said modified nucleotide analogues are selected from the group consisting of uridines or cytodines modified at the 5-position, adenosines and guanosines modified at the 8-position, deaza nucleotides, and O— and N— alkylated nucleotides.

12. The method according to claim 11, wherein said modified nucleotide analogues are selected from the group consisting of 5-(2amino)propyl uridine, 5-bromo uridine, 8-bromo guanosine, 7-deaza-adenosine, and N6-methyl adenosine.

13. The method according to claim 1, wherein said stabilized RNA molecule has two or more different substitutions.

14. The method according to claim 13, wherein said stabilized RNA molecule has at least one 2'-OMe sugar modified ribonucleotide and at least one phosphorothioate backbone modified ribonucleotide.

15. The method according to claim 13, wherein said stabilized RNA molecule has at least one 2'-F sugar modified ribonucleotide and at least one phosphorothioate backbone modified ribonucleotide.

16. The method according to claim 1, wherein said 3' overhang is comprised of phosphorothioate backbone modified ribonucleotides.

17. The method according to claim 1, wherein one of said RNA strands is complementary to a target nucleic acid.

18. The method according to claim 1, wherein said sugar modified ribonucleotide 2'-OH group is replaced by a member selected from the group consisting of OR, R, halo, SH, SR, $NH_2$, NHR, $NR_2$ and CN.

19. The method according to claim 1, wherein said RNA molecule is substantially free from contaminants occurring in cell extracts.

20. The method according to claim 1, wherein said cell is a non-embryonic mammalian cell.

21. A method for reducing the level of a target mRNA in a cell in vitro, comprising contacting a cell with an isolated synthetically prepared, double-stranded RNA molecule which mediates a reduction in the level of a target mRNA, wherein said molecule consists of two separate RNA strands each independently consisting of 19 -25 nucleotides, wherein said separate RNA strands form a single continuous double-stranded region and wherein at least one strand of said RNAi molecule has a 3'-overhang from 1-5 nucleotides, wherein one of said strands is complementary to a portion of a target mRNA, and said RNAi molecule comprises at least one stabilizing modification at the 5' end or the 3' end, or both ends, of the double-stranded RNAi molecule, wherein said stabilizing modification is selected from the group consisting of a sugar modified ribonucleotide and a backbone-modified ribonucleotide containing a phosphorothioate group, wherein said sugar modified ribonucleotide 2'-OH group is replaced by a member selected from the group consisting of H, OR, R, halo, SH, SR, $NH_2$, NHR, $NR_2$ and CN, wherein R is $C_1$-$C_6$ alkyl, $C_2$-$C_6$ alkenyl, $C_2$-$C_6$ alkynyl, and halo is F, Cl, Br or I.

22. The method of claim 1, wherein at least one strand of said RNA molecule comprises a 3'-overhang from 1 to 3 nucleotides.

23. The method of claim 22, wherein the 3'-overhang of the RNA molecule is 2 nucleotides in length.

24. The method of claim 22, wherein the 3'-overhang of the RNA molecule comprises at least one phosphorothioate backbone modified ribonucleotide.

25. The method of claim 22, wherein each strand of the molecule consists of 20-25 nucleotides in length.

26. The method of claim 25, wherein each strand of the RNA molecule consists of 21-23 nucleotides in length.

27. The method of claim 22, wherein the other strand is blunt-ended.

28. The method of claim 22, wherein said sugar modified ribonucleotide 2'-OH group is replaced by a member selected from the group consisting of OR, R, halo, SH, SR, $NH_2$, NHR, $NR_2$ and CN, wherein R is $C_1$-$C_6$ alkyl, $C_2$-$C_6$ alkenyl, $C_2$-$C_6$ alkynyl, and halo is F, Cl, Br or I.

29. The method of claim 22, wherein said RNA molecule comprises two or more different substitutions.

30. The method of claim 29, wherein said RNA molecule comprises at least one 2'-OMe sugar modified ribonucleotide and at least one phosphorothioate backbone modified ribonucleotide.

31. The method of claim 29, wherein said RNA molecule comprises at least one 2'-F sugar modified ribonucleotide and at least one phosphorothioate backbone modified ribonucleotide.

32. The method of claim 29, wherein said RNA molecule comprises at least one 2'-F sugar modified ribonucleotide, at least one 2'-OMe sugar modified ribonucleotide, and at least one phosphorothioate backbone modified ribonucleotide.

33. The method of claim 22, wherein said contacting comprises introducing said double-stranded RNA molecule into a target cell in which the reduction in the level of the target mRNA can occur.

34. The method of claim 33, wherein said double-stranded RNA molecule is introduced into said target cell using carrier-mediated delivery or injection.

35. The method according to claim 33, further comprising modulating a function of a gene in a cell in vitro by reducing the level of the target mRNA.

36. The method of claim 22, wherein one of said RNA strands is complementary to a target nucleic acid.

37. The method of claim 22, wherein one of said RNA strands has a sequence having an identity of at least 70 percent in the double-stranded portion of the RNA molecule to the target mRNA.

38. The method of claim 37, wherein the identity is at least 85 percent in the double-stranded portion of the RNA molecule.

39. The method of claim 37, wherein the identity is 100 percent in the double-stranded portion of the RNA molecule.

40. The method of claim 21, wherein at least one strand of said RNA molecule comprises a 3'-overhang from 1 to 3 nucleotides.

41. The method of claim 40, wherein the 3'-overhang of the RNA molecule is 2 nucleotides in length.

42. The method of claim 40, wherein the 3'-overhang of the RNA molecule comprises at least one phosphorothioate backbone modified ribonucleotide.

43. The method of claim 40, wherein each strand of the molecule consists of 20-25 nucleotides in length.

44. The method of claim 43, wherein each strand of the RNA molecule consists of 21-23 nucleotides in length.

45. The method of claim 40, wherein the other strand is blunt-ended.

46. The method of claim 40, wherein said sugar modified ribonucleotide 2'-OH group is replaced by a member selected from the group consisting of OR, R, halo, SH, SR, $NH_2$, NHR, $NR_2$ and CN, wherein R is $C_1$-$C_6$ alkyl, $C_2$-$C_6$ alkenyl, $C_2$-$C_6$ alkynyl, and halo is F, Cl, Br or I.

47. The method of claim 40, wherein said RNA molecule comprises two or more different substitutions.

48. The method of claim 47, wherein said RNA molecule comprises at least one 2'-OMe sugar modified ribonucleotide and at least one phosphorothioate backbone modified ribonucleotide.

49. The method of claim 47, wherein said RNA molecule comprises at least one 2'-F sugar modified ribonucleotide and at least one phosphorothioate backbone modified ribonucleotide.

50. The method of claim 47, wherein said RNA molecule comprises at least one 2'-F sugar modified ribonucleotide, at least one 2'-OMe sugar modified ribonucleotide, and at least one phosphorothioate backbone modified ribonucleotide.

51. The method of claim 22, wherein said contacting comprises introducing said double-stranded RNA molecule into a target cell in which the reduction in the level of target mRNA can occur.

52. The method of claim 51, wherein said double-stranded RNA molecule is introduced into said target cell using carrier-mediated delivery or injection.

53. The method according to claim 51, further comprising modulating a function of a gene in a cell in vitro by reducing the level of the target mRNA.

54. The method of claim 22, wherein one of said RNA strands is complementary to a target nucleic acid.

55. The method of claim 22, wherein one of said RNA strands has a sequence having an identity of at least 70 percent in the double-stranded portion of the RNA molecule to the target mRNA.

56. The method of claim 55, wherein the identity is at least 85 percent in the double-stranded portion of the RNA molecule.

57. The method of claim 55, wherein the identity is 100 percent in the double-stranded portion of the RNA molecule.

58. A method for reducing the level of a target mRNA in a cell in vitro, comprising:

contacting a cell with an isolated synthetically prepared, double-stranded RNA molecule which mediates a reduction in the level of a target mRNA, wherein said RNA molecule consists of two separate RNA strands each independently consisting of 19-25 nucleotides, and wherein at least one strand of said RNA molecule comprises a 3'-overhang from 1-5 nucleotides, wherein one of said strands is complementary to a portion of a target mRNA, and said RNA molecule comprises at least one stabilizing modification at the 5' end or the 3' end, or both ends, of the double-stranded RNA molecule, wherein said stabilizing modification is selected from the group consisting of a sugar modified ribonucleotide and a backbone-modified ribonucleotide containing a phosphorothioate group, wherein said sugar modified ribonucleotide 2'-OH group is replaced by a member selected from the group consisting of H, OR, R, halo, SH, SR, $NH_2$, NHR, $NR_2$ and CN, wherein R is $C_1$-$C_6$ alkyl, $C_2$-$C_6$ alkenyl, $C_2$-$C_6$ alkynyl, and halo is F, Cl, Br or I.

59. A method for reducing the level of a target mRNA in a cell in vitro, comprising:

contacting a cell with an isolated synthetically prepared, double-stranded RNA molecule which mediates a reduction in the level of a target mRNA, wherein said RNA molecule consists of two separate RNA strands each independently consisting of 19-23 nucleotides, and wherein at least one strand of said RNA molecule comprises a 3'-overhang from 1-3 nucleotides, wherein one of said strands is complementary to a portion of a target mRNA, and said RNA molecule comprises at least one stabilizing modification at the 5' end or the 3' end, or both ends, of the double-stranded RNA molecule, wherein said stabilizing modification is selected from the group consisting of a sugar modified ribonucleotide and a backbone-modified ribonucleotide containing a phosphorothioate group, wherein said sugar modified ribonucleotide 2'-OH group is replaced by a member selected from the group consisting of H, OR, R, halo, SH, SR, $NH_2$, NHR, $NR_2$ and CN, wherein R is $C_1$-$C_6$ alkyl, $C_2$-$C_6$ alkenyl, $C_2$-$C_6$ alkynyl, and halo is F, Cl, Br or I.

* * * * *

SEQUENCE LISTING

<160> NUMBER OF SEQ ID NOS: 101

<210> SEQ ID NO 1
<211> LENGTH: 38
<212> TYPE: DNA
<213> ORGANISM: Artificial sequence -continued

```
<220> FEATURE:
<223> OTHER INFORMATION: pGEM-luc sequence from the Pp-luc plasmid
<220> FEATURE:
<221> NAME/KEY: misc_feature
<222> LOCATION: (4)..(20)
<223> OTHER INFORMATION: T7 promoter

<400> SEQUENCE: 1
gcgtaatacg actcactata gaacaattgc ttttacag                              38

<210> SEQ ID NO 2
<211> LENGTH: 35
<212> TYPE: DNA
<213> ORGANISM: Artificial Sequence
<220> FEATURE:
<223> OTHER INFORMATION: pGEM-luc sequence from the Pp-luc plasmid
<220> FEATURE:
<221> NAME/KEY: misc_feature
<222> LOCATION: (1)..(17)
<223> OTHER INFORMATION: SP6 promoter

<400> SEQUENCE: 2
atttaggtga cactataggc ataaagaatt gaaga                                 35

<210> SEQ ID NO 3
<211> LENGTH: 30
<212> TYPE: DNA
<213> ORGANISM: Artificial sequence
<220> FEATURE:
<223> OTHER INFORMATION: reverse transcription primer for cloning RNAs
<220> FEATURE:
<221> NAME/KEY: misc_feature
<222> LOCATION: (10)..(15)
<223> OTHER INFORMATION: Eco R1 site

<400> SEQUENCE: 3
gactagctgg aattcaagga tgcggttaaa                                       30

<210> SEQ ID NO 4
<211> LENGTH: 30
<212> TYPE: DNA
<213> ORGANISM: Artificial sequence
<220> FEATURE:
<223> OTHER INFORMATION: PCR primer for cloning RNAs
<220> FEATURE:
<221> NAME/KEY: misc_feature
<222> LOCATION: (10)..(15)
<223> OTHER INFORMATION: Eco R1 site

<400> SEQUENCE: 4
cagccaacgg aattcatacg actcactaaa                                       30

<210> SEQ ID NO 5
<211> LENGTH: 36
<212> TYPE: DNA
<213> ORGANISM: Artificial sequence
<220> FEATURE:
<223> OTHER INFORMATION: PCR primer that amplifies firefly luciferase
      sequence in a plasmid
<220> FEATURE:
<221> NAME/KEY: misc_feature
<222> LOCATION: (1)..(19)
<223> OTHER INFORMATION: T7 promoter

<400> SEQUENCE: 5
taatacgact cactatagag cccatatcgt ttcata                                36

<210> SEQ ID NO 6
<211> LENGTH: 18
```

```
<212> TYPE: DNA
<213> ORGANISM: Artificial sequence
<220> FEATURE:
<223> OTHER INFORMATION: PCR primer that amplifies firefly luciferase
      sequence in a plasmid

<400> SEQUENCE: 6
agaggatgga accgctgg                                                     18

<210> SEQ ID NO 7
<211> LENGTH: 177
<212> TYPE: RNA
<213> ORGANISM: Artificial sequence
<220> FEATURE:
<223> OTHER INFORMATION: luciferase gene

<400> SEQUENCE: 7
gaacaauugc uuuuacagau gcacauaucg aggugaacau cacguacgcg gaauacuucg       60
aaauguccgu ucgguuggca gaagcuauga aacgauaugg gcugaauaca aaucacagaa      120
ucgucguaug cagugaaaac ucucuucaau ucuuuaugcc auagugauca ccuaaau         177

<210> SEQ ID NO 8
<211> LENGTH: 180
<212> TYPE: RNA
<213> ORGANISM: Artificial sequence
<220> FEATURE:
<223> OTHER INFORMATION: luciferase gene

<400> SEQUENCE: 8
ggcauaaaga auugaagaga guuuucacug cauacgacga uucugugauu uguauucagc       60
ccauaucguu ucauagcuuc ugccaaccga acggacauuu cgaaguauuc cgcguacgug      120
auguucaccu cgauaugugc aucuguaaaa gcaauuguuc uauagugagu cguauuacgc      180

<210> SEQ ID NO 9
<211> LENGTH: 39
<212> TYPE: RNA
<213> ORGANISM: Artificial sequence
<220> FEATURE:
<223> OTHER INFORMATION: luciferase gene

<400> SEQUENCE: 9
gcacauaucg aggugaacau cacguacgcg gaauacuuc                              39

<210> SEQ ID NO 10
<211> LENGTH: 52
<212> TYPE: RNA
<213> ORGANISM: Artificial sequence
<220> FEATURE:
<223> OTHER INFORMATION: luciferase gene

<400> SEQUENCE: 10
gcacauaucg aggugaacau cacguacgcg gaauacuucg aaauguccgu uc               52

<210> SEQ ID NO 11
<211> LENGTH: 111
<212> TYPE: RNA
<213> ORGANISM: Artificial sequence
<220> FEATURE:
<223> OTHER INFORMATION: luciferase gene

<400> SEQUENCE: 11
gcacauaucg aggugaacau cacguacgcg gaauacuucg aaauguccgu ucgguuggca       60
gaagcuauga aacgauaugg gcugaauaca aaucacagaa ucgucguaug c                111
```

```
<210> SEQ ID NO 12
<211> LENGTH: 52
<212> TYPE: RNA
<213> ORGANISM: Artificial sequence
<220> FEATURE:
<223> OTHER INFORMATION: luciferase gene

<400> SEQUENCE: 12
gcacauaucg aggugaacau cacguacgcg gaauacuucg aaauguccgu uc          52

<210> SEQ ID NO 13
<211> LENGTH: 54
<212> TYPE: RNA
<213> ORGANISM: Artificial sequence
<220> FEATURE:
<223> OTHER INFORMATION: luciferase gene

<400> SEQUENCE: 13
gaacggacau uucgaaguau uccgcguacg ugauguucac cucgauaugu gcac        54

<210> SEQ ID NO 14
<211> LENGTH: 21
<212> TYPE: RNA
<213> ORGANISM: Artificial sequence
<220> FEATURE:
<223> OTHER INFORMATION: luciferase gene

<400> SEQUENCE: 14
cguacgcgga auacuucgau u                                            21

<210> SEQ ID NO 15
<211> LENGTH: 21
<212> TYPE: RNA
<213> ORGANISM: Artificial sequence
<220> FEATURE:
<223> OTHER INFORMATION: luciferase gene

<400> SEQUENCE: 15
ucgaaguauu ccgcguacgu u                                            21

<210> SEQ ID NO 16
<211> LENGTH: 21
<212> TYPE: DNA
<213> ORGANISM: Artificial sequence
<220> FEATURE:
<223> OTHER INFORMATION: luciferase gene
<220> FEATURE:
<221> NAME/KEY: misc_feature
<222> LOCATION: (1)..(21)
<223> OTHER INFORMATION: molecule is combined DNA/RNA

<400> SEQUENCE: 16
cguacgcgga auacuucgat t                                            21

<210> SEQ ID NO 17
<211> LENGTH: 21
<212> TYPE: DNA
<213> ORGANISM: Artificial sequence
<220> FEATURE:
<223> OTHER INFORMATION: luciferase gene
<220> FEATURE:
<221> NAME/KEY: misc_feature
<222> LOCATION: (1)..(21)
<223> OTHER INFORMATION: molecule is combined DNA/RNA

<400> SEQUENCE: 17
```
ucgaaguauu ccgcguacgt t                                              21

<210> SEQ ID NO 18
<211> LENGTH: 21
<212> TYPE: DNA
<213> ORGANISM: Artificial sequence
<220> FEATURE:
<223> OTHER INFORMATION: luciferase gene
<220> FEATURE:
<221> NAME/KEY: misc_feature
<222> LOCATION: (1)..(21)
<223> OTHER INFORMATION: molecule is combined DNA/RNA

<400> SEQUENCE: 18
cuuacgcuga guacuucgat t                                              21

<210> SEQ ID NO 19
<211> LENGTH: 21
<212> TYPE: DNA
<213> ORGANISM: Artificial sequence
<220> FEATURE:
<223> OTHER INFORMATION: luciferase gene
<220> FEATURE:
<221> NAME/KEY: misc_feature
<222> LOCATION: (1)..(21)
<223> OTHER INFORMATION: molecule is combined DNA/RNA

<400> SEQUENCE: 19
ucgaaguacu cagcguaagt t                                              21

<210> SEQ ID NO 20
<211> LENGTH: 21
<212> TYPE: DNA
<213> ORGANISM: Artificial sequence
<220> FEATURE:
<223> OTHER INFORMATION: luciferase gene
<220> FEATURE:
<221> NAME/KEY: misc_feature
<222> LOCATION: (1)..(21)
<223> OTHER INFORMATION: molecule is combined DNA/RNA

<400> SEQUENCE: 20
agcuucauaa ggcgcaugct t                                              21

<210> SEQ ID NO 21
<211> LENGTH: 21
<212> TYPE: DNA
<213> ORGANISM: Artificial sequence
<220> FEATURE:
<223> OTHER INFORMATION: luciferase gene
<220> FEATURE:
<221> NAME/KEY: misc_feature
<222> LOCATION: (1)..(21)
<223> OTHER INFORMATION: molecule is combined DNA/RNA

<400> SEQUENCE: 21
gcaugcgccu uaugaagcut t                                              21

<210> SEQ ID NO 22
<211> LENGTH: 21
<212> TYPE: DNA
<213> ORGANISM: Artificial sequence
<220> FEATURE:
<223> OTHER INFORMATION: luciferase gene
<220> FEATURE:
<221> NAME/KEY: misc_feature
<222> LOCATION: (1)..(21)
<223> OTHER INFORMATION: molecule is combined DNA/RNA

<400> SEQUENCE: 22
aaacaugcag aaaaugcugt t                                           21

<210> SEQ ID NO 23
<211> LENGTH: 21
<212> TYPE: DNA
<213> ORGANISM: Artificial sequence
<220> FEATURE:
<223> OTHER INFORMATION: luciferase gene
<220> FEATURE:
<221> NAME/KEY: misc_feature
<222> LOCATION: (1)..(21)
<223> OTHER INFORMATION: molecule is combined DNA/RNA

<400> SEQUENCE: 23
cagcauuuuc ugcauguuut t                                           21

<210> SEQ ID NO 24
<211> LENGTH: 21
<212> TYPE: RNA
<213> ORGANISM: Artificial sequence
<220> FEATURE:
<223> OTHER INFORMATION: luciferase gene

<400> SEQUENCE: 24
aucacguacg cggaauacuu c                                           21

<210> SEQ ID NO 25
<211> LENGTH: 21
<212> TYPE: RNA
<213> ORGANISM: Artificial sequence
<220> FEATURE:
<223> OTHER INFORMATION: luciferase gene

<400> SEQUENCE: 25
guauuccgcg uacgugaugu u                                           21

<210> SEQ ID NO 26
<211> LENGTH: 21
<212> TYPE: RNA
<213> ORGANISM: Artificial sequence
<220> FEATURE:
<223> OTHER INFORMATION: luciferase gene

<400> SEQUENCE: 26
ucacguacgc ggaauacuuc g                                           21

<210> SEQ ID NO 27
<211> LENGTH: 21
<212> TYPE: RNA
<213> ORGANISM: Artificial sequence
<220> FEATURE:
<223> OTHER INFORMATION: luciferase gene

<400> SEQUENCE: 27
cacguacgcg gaauacuucg a                                           21

<210> SEQ ID NO 28
<211> LENGTH: 21
<212> TYPE: RNA
<213> ORGANISM: Artificial sequence
<220> FEATURE:
<223> OTHER INFORMATION: luciferase gene

<400> SEQUENCE: 28
acguacgcgg aauacuucga a                                           21

<210> SEQ ID NO 29
<211> LENGTH: 21
<212> TYPE: RNA
<213> ORGANISM: Artificial sequence
<220> FEATURE:
<223> OTHER INFORMATION: luciferase gene

<400> SEQUENCE: 29
cguacgcgga auacuucgaa a                                             21

<210> SEQ ID NO 30
<211> LENGTH: 21
<212> TYPE: RNA
<213> ORGANISM: Artificial sequence
<220> FEATURE:
<223> OTHER INFORMATION: luciferase gene

<400> SEQUENCE: 30
aguauuccgc guacgugaug u                                             21

<210> SEQ ID NO 31
<211> LENGTH: 21
<212> TYPE: RNA
<213> ORGANISM: Artificial sequence
<220> FEATURE:
<223> OTHER INFORMATION: luciferase gene

<400> SEQUENCE: 31
aaguauuccg cguacgugau g                                             21

<210> SEQ ID NO 32
<211> LENGTH: 21
<212> TYPE: RNA
<213> ORGANISM: Artificial sequence
<220> FEATURE:
<223> OTHER INFORMATION: luciferase gene

<400> SEQUENCE: 32
gaaguauucc gcguacguga u                                             21

<210> SEQ ID NO 33
<211> LENGTH: 21
<212> TYPE: RNA
<213> ORGANISM: Artificial sequence
<220> FEATURE:
<223> OTHER INFORMATION: luciferase gene

<400> SEQUENCE: 33
cgaaguauuc cgcguacgug a                                             21

<210> SEQ ID NO 34
<211> LENGTH: 21
<212> TYPE: RNA
<213> ORGANISM: Artificial sequence
<220> FEATURE:
<223> OTHER INFORMATION: luciferase gene

<400> SEQUENCE: 34
ucgaaguauu ccgcguacgu g                                             21

<210> SEQ ID NO 35
<211> LENGTH: 21
<212> TYPE: RNA
<213> ORGANISM: Artificial sequence
<220> FEATURE:
<223> OTHER INFORMATION: luciferase gene

```
<400> SEQUENCE: 35
uucgaaguau uccgcguacg u                                              21

<210> SEQ ID NO 36
<211> LENGTH: 21
<212> TYPE: RNA
<213> ORGANISM: Artificial sequence
<220> FEATURE:
<223> OTHER INFORMATION: luciferase gene

<400> SEQUENCE: 36
uuucgaagua uuccgcguac g                                              21

<210> SEQ ID NO 37
<211> LENGTH: 18
<212> TYPE: RNA
<213> ORGANISM: Artificial sequence
<220> FEATURE:
<223> OTHER INFORMATION: luciferase gene

<400> SEQUENCE: 37
cguacgcgga auacuucg                                                  18

<210> SEQ ID NO 38
<211> LENGTH: 21
<212> TYPE: RNA
<213> ORGANISM: Artificial sequence
<220> FEATURE:
<223> OTHER INFORMATION: luciferase gene

<400> SEQUENCE: 38
uucgaaguau uccgcguacg u                                              21

<210> SEQ ID NO 39
<211> LENGTH: 19
<212> TYPE: RNA
<213> ORGANISM: Artificial sequence
<220> FEATURE:
<223> OTHER INFORMATION: luciferase gene

<400> SEQUENCE: 39
cguacgcgga auacuucga                                                 19

<210> SEQ ID NO 40
<211> LENGTH: 20
<212> TYPE: RNA
<213> ORGANISM: Artificial sequence
<220> FEATURE:
<223> OTHER INFORMATION: luciferase gene

<400> SEQUENCE: 40
cguacgcgga auacuucgaa                                                20

<210> SEQ ID NO 41
<211> LENGTH: 21
<212> TYPE: RNA
<213> ORGANISM: Artificial sequence
<220> FEATURE:
<223> OTHER INFORMATION: luciferase gene

<400> SEQUENCE: 41
cguacgcgga auacuucgaa a                                              21

<210> SEQ ID NO 42
```

```
<211> LENGTH: 22
<212> TYPE: RNA
<213> ORGANISM: Artificial sequence
<220> FEATURE:
<223> OTHER INFORMATION: luciferase gene

<400> SEQUENCE: 42
cguacgcgga auacuucgaa au                                            22

<210> SEQ ID NO 43
<211> LENGTH: 23
<212> TYPE: RNA
<213> ORGANISM: Artificial sequence
<220> FEATURE:
<223> OTHER INFORMATION: luciferase gene

<400> SEQUENCE: 43
cguacgcgga auacuucgaa aug                                           23

<210> SEQ ID NO 44
<211> LENGTH: 24
<212> TYPE: RNA
<213> ORGANISM: Artificial sequence
<220> FEATURE:
<223> OTHER INFORMATION: luciferase gene

<400> SEQUENCE: 44
cguacgcgga auacuucgaa augu                                          24

<210> SEQ ID NO 45
<211> LENGTH: 25
<212> TYPE: RNA
<213> ORGANISM: Artificial sequence
<220> FEATURE:
<223> OTHER INFORMATION: luciferase gene

<400> SEQUENCE: 45
cguacgcgga auacuucgaa auguc                                         25

<210> SEQ ID NO 46
<211> LENGTH: 21
<212> TYPE: RNA
<213> ORGANISM: Artificial sequence
<220> FEATURE:
<223> OTHER INFORMATION: luciferase gene

<400> SEQUENCE: 46
ucgaaguauu ccgcguacgu g                                             21

<210> SEQ ID NO 47
<211> LENGTH: 21
<212> TYPE: RNA
<213> ORGANISM: Artificial sequence
<220> FEATURE:
<223> OTHER INFORMATION: luciferase gene

<400> SEQUENCE: 47
cgaaguauuc cgcguacgug a                                             21

<210> SEQ ID NO 48
<211> LENGTH: 20
<212> TYPE: RNA
<213> ORGANISM: Artificial sequence
<220> FEATURE:
<223> OTHER INFORMATION: luciferase gene

<400> SEQUENCE: 48
```

-continued cguacgcgga auacuucgaa                                        20

<210> SEQ ID NO 49
<211> LENGTH: 20
<212> TYPE: RNA
<213> ORGANISM: Artificial sequence
<220> FEATURE:
<223> OTHER INFORMATION: luciferase gene

<400> SEQUENCE: 49
cgaaguauuc cgcguacgug                                        20

<210> SEQ ID NO 50
<211> LENGTH: 21
<212> TYPE: RNA
<213> ORGANISM: Artificial sequence
<220> FEATURE:
<223> OTHER INFORMATION: luciferase gene

<400> SEQUENCE: 50
cguacgcgga auacuucgaa a                                      21

<210> SEQ ID NO 51
<211> LENGTH: 21
<212> TYPE: RNA
<213> ORGANISM: Artificial sequence
<220> FEATURE:
<223> OTHER INFORMATION: luciferase gene

<400> SEQUENCE: 51
ucgaaguauu ccgcguacgu g                                      21

<210> SEQ ID NO 52
<211> LENGTH: 22
<212> TYPE: RNA
<213> ORGANISM: Artificial sequence
<220> FEATURE:
<223> OTHER INFORMATION: luciferase gene

<400> SEQUENCE: 52
cguacgcgga auacuucgaa au                                     22

<210> SEQ ID NO 53
<211> LENGTH: 22
<212> TYPE: RNA
<213> ORGANISM: Artificial sequence
<220> FEATURE:
<223> OTHER INFORMATION: luciferase gene

<400> SEQUENCE: 53
uucgaaguau uccgcguacg ug                                     22

<210> SEQ ID NO 54
<211> LENGTH: 23
<212> TYPE: RNA
<213> ORGANISM: Artificial sequence
<220> FEATURE:
<223> OTHER INFORMATION: luciferase gene

<400> SEQUENCE: 54
cguacgcgga auacuucgaa aug                                    23

<210> SEQ ID NO 55
<211> LENGTH: 23
<212> TYPE: RNA

```
<213> ORGANISM: Artificial sequence
<220> FEATURE:
<223> OTHER INFORMATION: luciferase gene

<400> SEQUENCE: 55
uuucgaagua uuccgcguac gug                                         23

<210> SEQ ID NO 56
<211> LENGTH: 24
<212> TYPE: RNA
<213> ORGANISM: Artificial sequence
<220> FEATURE:
<223> OTHER INFORMATION: luciferase gene

<400> SEQUENCE: 56
cguacgcgga auacuucgaa augu                                        24

<210> SEQ ID NO 57
<211> LENGTH: 24
<212> TYPE: RNA
<213> ORGANISM: Artificial sequence
<220> FEATURE:
<223> OTHER INFORMATION: luciferase gene

<400> SEQUENCE: 57
auuucgaagu auuccgcgua cgug                                        24

<210> SEQ ID NO 58
<211> LENGTH: 25
<212> TYPE: RNA
<213> ORGANISM: Artificial sequence
<220> FEATURE:
<223> OTHER INFORMATION: luciferase gene

<400> SEQUENCE: 58
cguacgcgga auacuucgaa auguc                                       25

<210> SEQ ID NO 59
<211> LENGTH: 25
<212> TYPE: RNA
<213> ORGANISM: Artificial sequence
<220> FEATURE:
<223> OTHER INFORMATION: luciferase gene

<400> SEQUENCE: 59
cauuucgaag uauuccgcgu acgug                                       25

<210> SEQ ID NO 60
<211> LENGTH: 19
<212> TYPE: RNA
<213> ORGANISM: Artificial sequence
<220> FEATURE:
<223> OTHER INFORMATION: luciferase gene

<400> SEQUENCE: 60
guacgcggaa uacuucgaa                                              19

<210> SEQ ID NO 61
<211> LENGTH: 20
<212> TYPE: RNA
<213> ORGANISM: Artificial sequence
<220> FEATURE:
<223> OTHER INFORMATION: luciferase gene

<400> SEQUENCE: 61
ucgaaguauu ccgcguacgu                                             20
```

```
<210> SEQ ID NO 62
<211> LENGTH: 22
<212> TYPE: RNA
<213> ORGANISM: Artificial sequence
<220> FEATURE:
<223> OTHER INFORMATION: luciferase gene

<400> SEQUENCE: 62
acguacgcgg aauacuucga aa                                              22

<210> SEQ ID NO 63
<211> LENGTH: 22
<212> TYPE: RNA
<213> ORGANISM: Artificial sequence
<220> FEATURE:
<223> OTHER INFORMATION: luciferase gene

<400> SEQUENCE: 63
ucgaaguauu ccgcguacgu ga                                              22

<210> SEQ ID NO 64
<211> LENGTH: 23
<212> TYPE: RNA
<213> ORGANISM: Artificial sequence
<220> FEATURE:
<223> OTHER INFORMATION: luciferase gene

<400> SEQUENCE: 64
cacguacgcg gaauacuucg aaa                                             23

<210> SEQ ID NO 65
<211> LENGTH: 23
<212> TYPE: RNA
<213> ORGANISM: Artificial sequence
<220> FEATURE:
<223> OTHER INFORMATION: luciferase gene

<400> SEQUENCE: 65
ucgaaguauu ccgcguacgu gau                                             23

<210> SEQ ID NO 66
<211> LENGTH: 21
<212> TYPE: RNA
<213> ORGANISM: Artificial sequence
<220> FEATURE:
<223> OTHER INFORMATION: luciferase gene

<400> SEQUENCE: 66
acguacgcgg aauacuucga a                                               21

<210> SEQ ID NO 67
<211> LENGTH: 21
<212> TYPE: RNA
<213> ORGANISM: Artificial sequence
<220> FEATURE:
<223> OTHER INFORMATION: luciferase gene

<400> SEQUENCE: 67
cgaaguauuc cgcguacgug a                                               21

<210> SEQ ID NO 68
<211> LENGTH: 21
<212> TYPE: RNA
<213> ORGANISM: Artificial sequence
<220> FEATURE:
```

```
<223> OTHER INFORMATION: luciferase gene

<400> SEQUENCE: 68
cacguacgcg gaauacuucg a                                              21

<210> SEQ ID NO 69
<211> LENGTH: 21
<212> TYPE: RNA
<213> ORGANISM: Artificial sequence
<220> FEATURE:
<223> OTHER INFORMATION: luciferase gene

<400> SEQUENCE: 69
gaaguauucc gcguacguga u                                              21

<210> SEQ ID NO 70
<211> LENGTH: 21
<212> TYPE: RNA
<213> ORGANISM: Artificial sequence
<220> FEATURE:
<223> OTHER INFORMATION: luciferase gene

<400> SEQUENCE: 70
ucacguacgc ggaauacuuc g                                              21

<210> SEQ ID NO 71
<211> LENGTH: 21
<212> TYPE: RNA
<213> ORGANISM: Artificial sequence
<220> FEATURE:
<223> OTHER INFORMATION: luciferase gene

<400> SEQUENCE: 71 aaguauccg cguacgugau g                                               21

<210> SEQ ID NO 72
<211> LENGTH: 21
<212> TYPE: RNA
<213> ORGANISM: Artificial sequence
<220> FEATURE:
<223> OTHER INFORMATION: luciferase gene

<400> SEQUENCE: 72
aucacguacg cggaauacuu c                                              21

<210> SEQ ID NO 73
<211> LENGTH: 21
<212> TYPE: RNA
<213> ORGANISM: Artificial sequence
<220> FEATURE:
<223> OTHER INFORMATION: luciferase gene

<400> SEQUENCE: 73
aguauuccgc guacgugaug u                                              21

<210> SEQ ID NO 74
<211> LENGTH: 18
<212> TYPE: RNA
<213> ORGANISM: Artificial sequence
<220> FEATURE:
<223> OTHER INFORMATION: luciferase gene

<400> SEQUENCE: 74
acgcggaaua cuucgaaa                                                  18
```

```
<210> SEQ ID NO 75
<211> LENGTH: 21
<212> TYPE: RNA
<213> ORGANISM: Artificial sequence
<220> FEATURE:
<223> OTHER INFORMATION: luciferase gene

<400> SEQUENCE: 75
ucgaaguauu ccgcguacgu g                                    21

<210> SEQ ID NO 76
<211> LENGTH: 19
<212> TYPE: RNA
<213> ORGANISM: Artificial sequence
<220> FEATURE:
<223> OTHER INFORMATION: luciferase gene

<400> SEQUENCE: 76
uacgcggaau acuucgaaa                                       19

<210> SEQ ID NO 77
<211> LENGTH: 20
<212> TYPE: RNA
<213> ORGANISM: Artificial sequence
<220> FEATURE:
<223> OTHER INFORMATION: luciferase gene

<400> SEQUENCE: 77
guacgcggaa uacuucgaaa                                      20

<210> SEQ ID NO 78
<211> LENGTH: 21
<212> TYPE: RNA
<213> ORGANISM: Artificial sequence
<220> FEATURE:
<223> OTHER INFORMATION: luciferase gene

<400> SEQUENCE: 78
cguacgcgga auacuucgaa a                                    21

<210> SEQ ID NO 79
<211> LENGTH: 22
<212> TYPE: RNA
<213> ORGANISM: Artificial sequence
<220> FEATURE:
<223> OTHER INFORMATION: luciferase gene

<400> SEQUENCE: 79
acguacgcgg aauacuucga aa                                   22

<210> SEQ ID NO 80
<211> LENGTH: 23
<212> TYPE: RNA
<213> ORGANISM: Artificial sequence
<220> FEATURE:
<223> OTHER INFORMATION: luciferase gene

<400> SEQUENCE: 80
cacguacgcg gaauacuucg aaa                                  23

<210> SEQ ID NO 81
<211> LENGTH: 21
<212> TYPE: DNA
<213> ORGANISM: Artificial sequence
<220> FEATURE:
<223> OTHER INFORMATION: luciferase gene
<220> FEATURE:
```

-continued

```
<221> NAME/KEY: misc_feature
<222> LOCATION: (1)..(21)
<223> OTHER INFORMATION: molecule is combined DNA/RNA

<400> SEQUENCE: 81
cguacgcgga auacuucgat t                                              21

<210> SEQ ID NO 82
<211> LENGTH: 21
<212> TYPE: DNA
<213> ORGANISM: Artificial sequence
<220> FEATURE:
<223> OTHER INFORMATION: luciferase gene
<220> FEATURE:
<221> NAME/KEY: misc_feature
<222> LOCATION: (1)..(21)
<223> OTHER INFORMATION: molecule is combined DNA/RNA

<400> SEQUENCE: 82
ucgaaguauu ccgcguacgt t                                              21

<210> SEQ ID NO 83
<211> LENGTH: 21
<212> TYPE: DNA
<213> ORGANISM: Artificial sequence
<220> FEATURE:
<223> OTHER INFORMATION: luciferase gene
<220> FEATURE:
<221> NAME/KEY: misc_feature
<222> LOCATION: (1)..(21)
<223> OTHER INFORMATION: molecule is combined DNA/RNA

<400> SEQUENCE: 83
augccgcgga auacuucgat t                                              21

<210> SEQ ID NO 84
<211> LENGTH: 21
<212> TYPE: DNA
<213> ORGANISM: Artificial sequence
<220> FEATURE:
<223> OTHER INFORMATION: luciferase gene
<220> FEATURE:
<221> NAME/KEY: misc_feature
<222> LOCATION: (1)..(21)
<223> OTHER INFORMATION: molecule is combined DNA/RNA

<400> SEQUENCE: 84
ucgaaguauu ccgcggcaut t                                              21

<210> SEQ ID NO 85
<211> LENGTH: 21
<212> TYPE: DNA
<213> ORGANISM: Artificial sequence
<220> FEATURE:
<223> OTHER INFORMATION: luciferase gene
<220> FEATURE:
<221> NAME/KEY: misc_feature
<222> LOCATION: (1)..(21)
<223> OTHER INFORMATION: molecule is combined DNA/RNA

<400> SEQUENCE: 85
cguagcgcga auacuucgat t                                              21

<210> SEQ ID NO 86
<211> LENGTH: 21
<212> TYPE: DNA
<213> ORGANISM: Artificial sequence
<220> FEATURE:
<223> OTHER INFORMATION: luciferase gene
```

```
<220> FEATURE:
<221> NAME/KEY: misc_feature
<222> LOCATION: (1)..(21)
<223> OTHER INFORMATION: molecule is combined DNA/RNA

<400> SEQUENCE: 86
ucgaaguauu cgcgcuacgt t                                              21

<210> SEQ ID NO 87
<211> LENGTH: 21
<212> TYPE: DNA
<213> ORGANISM: Artificial sequence
<220> FEATURE:
<223> OTHER INFORMATION: luciferase gene
<220> FEATURE:
<221> NAME/KEY: misc_feature
<222> LOCATION: (1)..(21)
<223> OTHER INFORMATION: molecule is combined DNA/RNA

<400> SEQUENCE: 87
cguacgcgag uaacuucgat t                                              21

<210> SEQ ID NO 88
<211> LENGTH: 21
<212> TYPE: DNA
<213> ORGANISM: Artificial sequence
<220> FEATURE:
<223> OTHER INFORMATION: luciferase gene
<220> FEATURE:
<221> NAME/KEY: misc_feature
<222> LOCATION: (1)..(21)
<223> OTHER INFORMATION: molecule is combined DNA/RNA

<400> SEQUENCE: 88
ucgaaguuac ucgcguacgt t                                              21

<210> SEQ ID NO 89
<211> LENGTH: 21
<212> TYPE: DNA
<213> ORGANISM: Artificial sequence
<220> FEATURE:
<223> OTHER INFORMATION: luciferase gene
<220> FEATURE:
<221> NAME/KEY: misc_feature
<222> LOCATION: (1)..(21)
<223> OTHER INFORMATION: molecule is combined DNA/RNA

<400> SEQUENCE: 89
cguacgcgga auuucacgat t                                              21

<210> SEQ ID NO 90
<211> LENGTH: 21
<212> TYPE: DNA
<213> ORGANISM: Artificial sequence
<220> FEATURE:
<223> OTHER INFORMATION: luciferase gene
<220> FEATURE:
<221> NAME/KEY: misc_feature
<222> LOCATION: (1)..(21)
<223> OTHER INFORMATION: molecule is combined DNA/RNA

<400> SEQUENCE: 90
ucgugaaauu ccgcguacgt t                                              21

<210> SEQ ID NO 91
<211> LENGTH: 21
<212> TYPE: DNA
<213> ORGANISM: Artificial sequence
<220> FEATURE:
```

```
<223> OTHER INFORMATION: luciferase gene
<220> FEATURE:
<221> NAME/KEY: misc_feature
<222> LOCATION: (1)..(21)
<223> OTHER INFORMATION: molecule is combined DNA/RNA

<400> SEQUENCE: 91
cguacgcgga auacuuagct t                                              21

<210> SEQ ID NO 92
<211> LENGTH: 21
<212> TYPE: DNA
<213> ORGANISM: Artificial sequence
<220> FEATURE:
<223> OTHER INFORMATION: luciferase gene
<220> FEATURE:
<221> NAME/KEY: misc_feature
<222> LOCATION: (1)..(21)
<223> OTHER INFORMATION: molecule is combined DNA/RNA

<400> SEQUENCE: 92
gcuaaguauu ccgcguacgt t                                              21

<210> SEQ ID NO 93
<211> LENGTH: 21
<212> TYPE: DNA
<213> ORGANISM: Artificial sequence
<220> FEATURE:
<223> OTHER INFORMATION: luciferase gene
<220> FEATURE:
<221> NAME/KEY: misc_feature
<222> LOCATION: (1)..(21)
<223> OTHER INFORMATION: molecule is combined DNA/RNA

<400> SEQUENCE: 93
cguacgcggu auacuucgat t                                              21

<210> SEQ ID NO 94
<211> LENGTH: 21
<212> TYPE: DNA
<213> ORGANISM: Artificial sequence
<220> FEATURE:
<223> OTHER INFORMATION: luciferase gene
<220> FEATURE:
<221> NAME/KEY: misc_feature
<222> LOCATION: (1)..(21)
<223> OTHER INFORMATION: molecule is combined DNA/RNA

<400> SEQUENCE: 94
ucgaaguaua ccgcguacgt t                                              21

<210> SEQ ID NO 95
<211> LENGTH: 21
<212> TYPE: DNA
<213> ORGANISM: Artificial sequence
<220> FEATURE:
<223> OTHER INFORMATION: luciferase gene
<220> FEATURE:
<221> NAME/KEY: misc_feature
<222> LOCATION: (1)..(21)
<223> OTHER INFORMATION: molecule is combined DNA/RNA

<400> SEQUENCE: 95
cguacgcgga uuacuucgat t                                              21

<210> SEQ ID NO 96
<211> LENGTH: 21
<212> TYPE: DNA
<213> ORGANISM: Artificial sequence
```

```
<220> FEATURE:
<223> OTHER INFORMATION: luciferase gene
<220> FEATURE:
<221> NAME/KEY: misc_feature
<222> LOCATION: (1)..(21)
<223> OTHER INFORMATION: molecule is combined DNA/RNA

<400> SEQUENCE: 96
ucgaaguaau ccgcguacgt t                                               21

<210> SEQ ID NO 97
<211> LENGTH: 39
<212> TYPE: RNA
<213> ORGANISM: Artificial sequence
<220> FEATURE:
<223> OTHER INFORMATION: luciferase gene

<400> SEQUENCE: 97
gaaguauucc gcguacguga uguucaccuc gauaugugc                            39

<210> SEQ ID NO 98
<211> LENGTH: 52
<212> TYPE: RNA
<213> ORGANISM: Artificial sequence
<220> FEATURE:
<223> OTHER INFORMATION: luciferase gene

<400> SEQUENCE: 98
gaacggacau uucgaaguau uccgcguacg ugauguucac cucgauaugu gc             52

<210> SEQ ID NO 99
<211> LENGTH: 111
<212> TYPE: RNA
<213> ORGANISM: Artificial sequence
<220> FEATURE:
<223> OTHER INFORMATION: luciferase gene

<400> SEQUENCE: 99
gcauacgacg auucugugau uuguauucag cccauaucgu uucauagcuu cugccaaccg     60
aacggacauu ucgaaguauu ccgcguacgu gauguucacc ucgauaugug c              111

<210> SEQ ID NO 100
<211> LENGTH: 18
<212> TYPE: DNA
<213> ORGANISM: Artificial sequence
<220> FEATURE:
<223> OTHER INFORMATION: adapter nucleotide for cloning RNAs
<220> FEATURE:
<221> NAME/KEY: misc_feature
<222> LOCATION: (1)..(1)
<223> OTHER INFORMATION: phosphorylated
<220> FEATURE:
<221> NAME/KEY: misc_feature
<222> LOCATION: (1)..(3)
<223> OTHER INFORMATION: RNA
<220> FEATURE:
<221> NAME/KEY: misc_feature
<222> LOCATION: (1)..(18)
<223> OTHER INFORMATION: molecule is combined DNA/RNA
<220> FEATURE:
<221> NAME/KEY: misc_feature
<222> LOCATION: (4)..(18)
<223> OTHER INFORMATION: DNA
<220> FEATURE:
<221> NAME/KEY: misc_feature
<222> LOCATION: (18)..(18)
<223> OTHER INFORMATION: base modified with 4-hydroxymethylbenzyl

<400> SEQUENCE: 100
```

```
uuuaaccgca tccttctc                                          18

<210> SEQ ID NO 101
<211> LENGTH: 20
<212> TYPE: DNA
<213> ORGANISM: Artificial sequence
<220> FEATURE:
<223> OTHER INFORMATION: adapter nucleotide for cloning RNAs
<220> FEATURE:
<221> NAME/KEY: misc_feature
<222> LOCATION: (1)..(17)
<223> OTHER INFORMATION: DNA
<220> FEATURE:
<221> NAME/KEY: misc_feature
<222> LOCATION: (18)..(20)
<223> OTHER INFORMATION: RNA

<400> SEQUENCE: 101
tactaatacg actcactaaa                                        20
```